(12) United States Patent
Smrzka et al.

(10) Patent No.: US 10,406,197 B2
(45) Date of Patent: Sep. 10, 2019

(54) SUBSTANCES AND METHODS FOR THE USE IN PREVENTION AND/OR TREATMENT IN HUNTINGTON'S DISEASE

(71) Applicant: AFFIRIS AG, Vienna (AT)

(72) Inventors: Oskar Smrzka, Vienna (AT); Stefan Bartl, Vienna (AT); Michela Parth, Vienna (AT)

(73) Assignee: AFFIRIS AG, Vienna (AT)

( * ) Notice: Subject to any disclaimer, the term of this patent is extended or adjusted under 35 U.S.C. 154(b) by 1 day.

(21) Appl. No.: 15/324,962

(22) PCT Filed: Jul. 10, 2015

(86) PCT No.: PCT/EP2015/065792
§ 371 (c)(1),
(2) Date: Jan. 9, 2017

(87) PCT Pub. No.: WO2016/005545
PCT Pub. Date: Jan. 14, 2016

(65) Prior Publication Data
US 2017/0304384 A1    Oct. 26, 2017

(30) Foreign Application Priority Data

Jul. 10, 2014    (EP) .................................... 14176531

(51) Int. Cl.
| | |
|---|---|
| *A61K 38/02* | (2006.01) |
| *A61K 39/00* | (2006.01) |
| *A61K 39/42* | (2006.01) |
| *A61K 47/42* | (2017.01) |
| *A61K 47/51* | (2017.01) |
| *A61K 48/00* | (2006.01) |
| *C07K 14/47* | (2006.01) |
| *C07K 16/18* | (2006.01) |
| *C07K 16/28* | (2006.01) |
| *C07K 14/705* | (2006.01) |

(52) U.S. Cl.
CPC .......... *A61K 38/02* (2013.01); *A61K 39/0007* (2013.01); *A61K 39/42* (2013.01); *A61K 47/42* (2013.01); *A61K 47/51* (2017.08); *C07K 14/47* (2013.01); *C07K 14/705* (2013.01); *C07K 16/18* (2013.01); *C07K 16/286* (2013.01); *A61K 48/00* (2013.01); *A61K 2039/505* (2013.01); *A61K 2039/55505* (2013.01); *A61K 2039/6081* (2013.01); *C07K 2317/24* (2013.01); *C07K 2317/34* (2013.01); *C07K 2317/76* (2013.01); *G01N 2800/2835* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,731,168 A | 3/1998 | Carter et al. |
| 5,750,373 A | 5/1998 | Garrard et al. |
| 5,770,429 A | 6/1998 | Lonberg et al. |
| 6,075,181 A | 6/2000 | Kucherlapati et al. |
| 6,150,584 A | 11/2000 | Kucherlapati et al. |
| 7,041,870 B2 | 5/2006 | Tomizuka et al. |
| 7,189,826 B2 | 3/2007 | Rodman |
| 8,546,532 B2 | 10/2013 | Bonnin et al. |
| 2003/0166558 A1* | 9/2003 | Frangione .............. C07K 14/47 424/130.1 |
| 2005/0079574 A1 | 4/2005 | Bond |
| 2005/0119455 A1 | 6/2005 | Fuh et al. |
| 2005/0255113 A1* | 11/2005 | Huston .................. C07K 14/47 424/145.1 |
| 2005/0266000 A1 | 12/2005 | Bond et al. |
| 2006/0025576 A1 | 2/2006 | Miller et al. |
| 2007/0026029 A1 | 2/2007 | Mattner et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2009/0098150 A1* | 4/2009 | Krainc .................. C07K 14/47 424/185.1 |
| 2010/0158933 A1 | 6/2010 | Brown et al. |
| 2010/0233180 A1 | 9/2010 | Khoshnan et al. |
| 2011/0045603 A1 | 2/2011 | Guo et al. |
| 2011/0136146 A1 | 6/2011 | Paganetti |
| 2013/0287838 A1* | 10/2013 | Hickman ............ A61K 39/0007 424/450 |

(Continued)

FOREIGN PATENT DOCUMENTS

| | | |
|---|---|---|
| WO | WO 93/08829 A1 | 5/1993 |
| WO | WO 2004/006955 A1 | 1/2004 |

(Continued)

OTHER PUBLICATIONS

Uniprot "P42858" accessed from uniprot.org (Year: 2010).*

(Continued)

*Primary Examiner* — Adam Weidner

(74) *Attorney, Agent, or Firm* — Oblon, McClelland, Maier & Neustadt, L.L.P.

(57) ABSTRACT

Disclosed are immunogenic peptides of the HTT protein and HTT specific antibodies for use in the prevention and/or treatment of Huntington's disease.

6 Claims, 29 Drawing Sheets

Specification includes a Sequence Listing.

(56) References Cited

U.S. PATENT DOCUMENTS

2014/0121167 A1      5/2014    Maschat et al.

FOREIGN PATENT DOCUMENTS

| | | |
|---|---|---|
| WO | WO 2009/080251 A1 | 7/2009 |
| WO | WO 2009/080252 A1 | 7/2009 |
| WO | WO 2009/080253 A1 | 7/2009 |
| WO | WO 2009/080254 A1 | 7/2009 |
| WO | WO 2009/089004 A1 | 7/2009 |
| WO | WO 2010/015592 A2 | 2/2010 |
| WO | WO 2010/112193 A1 | 10/2010 |
| WO | WO 2010/115589 A1 | 10/2010 |
| WO | WO 2010/136172 A1 | 12/2010 |
| WO | WO 2010/145792 A1 | 12/2010 |
| WO | WO 2010/145793 A1 | 12/2010 |
| WO | WO 2012/140376 A1 | 10/2012 |
| WO | WO 2014/193632 A2 | 12/2014 |

OTHER PUBLICATIONS

International Search Report and Written Opinion of the International Searching Authority dated Dec. 18, 2015 in PCT/EP2015/065792.

Written Opinion of the International Searching Authority dated Jun. 3, 2016 in PCT/EP2015/065792 filed Jul. 10, 2015.

Written Opinion of the International Searching Authority dated Sep. 19, 2016 in PCT/EP2015/065792 filed Jul. 10, 2015.

International Preliminary Report on Patentability dated Oct. 31, 2016 in PCT/EP2015/065792 filed Jul. 10, 2015.

Extended European Search Report dated May 4, 2015 in Patent Application No. 14176531.3.

Francesca Persichetti, et al., "Normal and Expanded Huntington's Disease Gene Alleles Produce Distinguishable Proteins Due to Translation Across the CAG Repeat" Molecular Medicine, vol. 1, No. 4, XP000997528, May 1, 1995, pp. 374-383.

Jan Ko, et al., "New Anti-Huntingtin Monoclonal Antibodies: Implications for Huntingtin Conformation and its Binding Proteins" vol. 56, Nos. 3-4 XP002509144, Oct. 1, 2001, pp. 319-329.

Beverly L. Davidson, "Taking a Break from Huntingtin" Molecular Therapy, www.moleculartherapy.org, vol. 20, No. 10, Oct. 2012, p. 1838.

Marianne J.U. Novak, et al., "Huntington's Disease: Clinical Presentation and Treatment" International Review Of Neurobiology, vol. 98, 2011, pp. 297-323.

Andreas Weiss, "Mutant Huntingtin Quantification in Human Body Fluids" Speaker Abstract, 2014, 1 Page.

Bibiana K.Y. Wong, et al. "Group B: Animal Models of HD, Delineation of Caspase-6 Dependent Phenotypes in the YAC128 Mouse Model of Huntington Disease" Poster Abstract, 2014, p. 91.

Rona K. Graham, et al., "Cleavage at the Caspase-6 Site is Required for Neuronal Dysfunction and Degeneration Due to Mutant Huntingtin" vol. 125, 2006, pp. 1179-1191.

Yaghoub Safdari et al., "Antibody Humanization Methods—a Review and Update" Biotechnology and Genetic Engineering Reviews, vol. 29, No. 2, 2013, pp. 175-186 and cover pages.

Xuesong Chen. et al., "Expanded Polyglutamine-Binding Peptoid as a Novel Therapeutic Agent for Treatment of Huntington's Disease" Chemistry & Biology, vol. 18, XP28298159, Sep. 23, 2011, pp. 1113-1125.

David C. Butler, et al., "Engineered Antibody Therapies to Counteract Mutant Huntingtin and Related Toxic Intracellular Proteins" Progress in Neurobiology, vol. 97, XP28917039, 2012, pp. 190-204.

Andreas Weiss, et al., "Single-Step Detection of Mutant Huntingtin in Animal and Human Tissues: A Bioassay for Huntington's Disease" Analytical Biochemistry, vol. 395, XP26626766. 2009, pp. 8-15.

Cary Queen, et al., "A Humanized Antibody that Binds to the Interleukin 2 Receptor" Proc. Natl. Acad. Sci., vol. 86, 1989, pp. 10029-10033.

Peter Rice, et al., "EMBOSS: The European Molecular Biology Open Software Suite" vol. 16, No. 6. Jun. 2000, pp. 276-277.

"Antibodies" Kabat E.A. Sequences of Proteins of Immunoiogical Interest. http://www.bioinf.org.uk/abs/, 1991, pp. 1-10.

Jin Hong Kim. et al., "Humanization by CDR Grafting and Specificity—Determining Residue Grafting" Methods in Molecular Biology. vol. 907, 2012, pp. 237-245.

Thibaut Pelat, et al., "Obtention and Engineering of Non-Human Primate (NHP) Antibodies for Therapeutics" Mini-Reviews in Medicinal Chemistry, vol. 9, No. 14, 2009, pp. 1633-1638.

Manmohan Singh, et al., "Advances in Vaccine Adjuvants" Nature Biotechnology, vol. 17, Nov. 1999, pp. 1075-1081.

Zhiqiang Zheng. et al., "Huntington Disease and the Huntingtin Protein" Progress in Molecular Biology and Translational Science, vol. 107, 2012, pp. 189-214.

Nicholas Whitelegg, et al., "Antibody Variable Regions" Methods in Molecular Biology, vol. 248, 2004, pp. 51-91.

Sherie L. Morrison, et al., "Chimeric Human Antibody Molecules: Mouse Antigen-Binding Domains with Human Constant Region Domains" Proc Natl. Acad. Sci., vol. 81, 1984. pp. 6851-6855.

David C. Butler, et al., "Engineered Antibody Therapies to Counteract Mutant Huntingtin and Related Toxic Intracellular Proteins" Progress in Neurobiology, 2011, pp. 1-15.

Jonathan Bard, et al., "Advances in Huntington Disease Drug Discovery: Novel Approaches to Model Disease Phenotypes" Journal of Biomolecular Screening, vol. 19, No. 2, 2014. pp. 191-204 and cover page.

Anne Messer, et al., "Intrabodies as Neuroprotective Therapeutics" Neurotherapeutics, vol. 10, 2013, pp. 447-458.

Simon C. Warby, et al., "Activated Caspase-6 and Caspase-6-Cleaved Fragments of Huntingtin Specifically Colocalize in the Nucleus" Human Molecular Genetics, vol. 17, No. 15, 2008, pp. 2390-2404.

Amber L. Southwell, et al., "Perturbation with Intrabodies Reveals that Calpain Cleavage is Required for Degradation of Huntingtin Exon 1" Plos One, vol. 6, 2011, pp. 1-10.

Shenliang Yu, et al., "Drugging Unconventional Targets: Insights from Huntington's Disease" Trends in Pharmacological Sciences, vol. 35, No. 2, Feb. 2014, pp. 53-62.

Andreas Weiss, et al., "Mutant Huntingtin Fragmentation in Immune Cells Tracks Huntington's Disease Progression" The Journal of Clinical Investigation, http://www.jci.org, vol. 122, No. 10, Oct. 2012, pp. 3731-3736.

Markus Mandler, et al., "Next-Generation Active Immunization Approach for Synucleinopathies: Implications for Parkinson's Disease Clinical Trials" Acta Neuropathol, 2014, 19 Pages.

Volker Stadler, et al., "Combinatorial Synthesis of Peptide Arrays with a Laser Printer" Angewandte Chemie International Edition, vol. 47, 2008, pp. 7132-7135.

Xia Zhang, et al., "The Isolation and Characterization of Murine Macrophages" Current Protocols in Immunology, 2008, pp. 1-18.

Gisa Ellrichmann, et al., "The Role of the Immune System in Huntington's Disease" Clinical and Developmental Immunology, vol. 2013, 2013, pp. 1-11.

Ulrike Träger, et al., "HTT-Lowering Reverses Huntington's Disease Immune Dysfunction Caused by NFkB Pathway Dysregulation" BRAIN A Journal of Neurology, vol. 137, 2014, pp. 819-833.

A. Mader, et al., "Humanization Strategies for an Anti-Idiotypic Antibody Mimicking HIV-1 gp41" Protein Engineering, Design & Selection, vol. 23, No. 12, 2010, pp. 947-954.

Todd W. Miller, et al., DNA Vaccination against Mutant Huntingtin Ameliorates the HDR6/2 Diabetic Phenotype Molecular Therapy, vol. 7, No. 5, May 2003, pp. 572-579.

Philipp Holliger, et al., ""Diabodies": Small Bivalent and Bispecific Antibody Fragments" Proc. Natl. Acad. Sci. vol. 90, Jul. 1993, pp. 6444-6448.

Frederic A. Fellouse, et al., "Synthetic Antibodies from a Four-Amino-Acid Code: A Dominant Role for Tyrosine in Antigen Recognition" PNAS, www.pnas.org/doi/10.1073/pnas.0401786101, vol. 101, No. 34, 2004, pp. 12467-12472.

Rona K. Graham, et al., "Cleavage at the 586aa Caspase-6 Site in Mutant Huntingtin Influences Caspase-6 Activation in Vivo" J. Neurosci. vol. 30, 2010, pp. 1-22.

(56) References Cited

OTHER PUBLICATIONS

Xiaoyun Liu, et al., "Protein Expression in the Striatum and Cortex Regions of the Brain for a Mouse Model of Huntington's Disease" J. Proteome Res., 2007, pp. 1-21.

Xiaoyun Liu, et al., "Mapping the Human Plasma Proteome by SCX-LC-IMS-MS" Journal of the American Society Mass Spectrometry, vol. 18, 2007, pp. 1-29.

Jan Modregger, et al., "PACSIN 1 Interacts with Huntingtin and is Absent from Synaptic Varicosities in Presymptomatic Huntington's Disease Brains" Human Molecular Genetics, vol. 11, No. 21, 2002, pp. 2547-2558.

Gülgün Tezel, et al., "Immunoproteomic Analysis of Potential Serum Biomarker Candidates in Human Glaucoma" Investigative Ophthalmology & Visual Science, vol. 53, No. 13, Dec. 2012, pp. 8222-8231.

Remko Van Vught, et al., "Site-Specific Functionalization of Proteins and their Applications to Therapeutic Antibodies" Computational and Structural Biotechnology Journal, vol. 9, 2014, pp. 1-13.

Derek T.O'Hagan, et al., "Recent Advances in the Discovery and Delivery of Vaccine Adjuvants" Nature Reviews Drug Discovery, vol. 2, Sep. 2003, pp. 727-735.

Office Action dated Feb. 4, 2019 in Australian Patent Application No. 2015286604, 8 pages.

Dehay, B. et al. "Mapping of the epitope of monoclonal antibody 2B4 to the proline-rich region of human Huntingtin, a region critical for aggregation and toxicity" Biotechnology Journal, 2007, pp. 1-6 and cover page.

Examination Report has cited references during the examination of a parallel patent application in the Russian Federation, dated Feb. 27, 2019 w/English translation and Search Report.

David W. Colby, et al., "Potent Inhibition of huntingtin aggregation and cytotoxicity by a disulfide bond-free single-domain intracellular antibody", PNAS, Dec. 21, 2004, vol. 101, No. 51, pp. 17616-17621.

Volker Heiser, et al., "Inhibition of huntingtin fibrillogenesis by specific antibodies and small molecules: Implications for Huntington's disease therapy", PNAS, Jun. 6, 2000, vol. 97, No. 12, pp. 6739-6744.

Ruth Luthi-Carter, "Progress towards a Vaccine for Huntington's Disease", Molecular Therapy, vol. 7, No. 5, May 2003, pp. 569-570.

Andrew C.R. Martin, "Chapter 3 Protein Sequence and Structure Analysis of Antibody Variable Domains", Antibody Engineering, vol. 2, DOI 10.1007/978-3-642-01147-4_3, Springer-Verlag Berline Heidelberg, 2010.

Michael Sela, et al., "Therapeutic vaccines: realities of today and hopes for the future", Reviews/ Therapeutic focus, vol. 7, No. 12, Jun. 2002.

Office Action as received in the corresponding European Patent Application No. 15 736 494.4—116 dated May 21, 2019.

Rona K. Graham. et al., "Cleavage At the 586 Amino Acid Caspase-6 Site in Mutant huntingtin Influences Caspase-6 Activation *in Vivo*", The Journal of Neuroscience, Nov. 10, 2010, 30(45):pp. 15019-5029.

Office Action as received in the corresponding AU Patent Application No. 2015286604 dated May 15, 2019.

Israel Aharony, et al., "A Huntingtin-based peptide inhibitor of caspase-6 provides protection from mutant Huntingtin-induced motor and behavioral deficits", Human Molecular Genetics, 2015, vol. 24, No. 9, pp. 2604-2614.

* cited by examiner

Figure 27

| Name | Framework H | Framework L |
|---|---|---|
| hPRR13-1 | wt | wt |
| hPRR13-2 | H73 (T=>K) | wt |
| hPRR13-3 | H76 (G=>S) | wt |
| hPRR13-4 | H73 + H76 | wt |
| hPRR13-5 | wt | L47 (L=>W) |
| hPRR13-6 | H73 (T=>K) | L47 (L=>W) |
| hPRR13-7 | H76 (G=>S) | L47 (L=>W) |
| hPRR13-8 | H73 + H76 | L47 (L=>W) |
| hPRR13-9 | wt | L70 (D=>S) |
| hPRR13-10 | H73 (T=>K) | L70 (D=>S) |
| hPRR13-11 | H76 (G=>S) | L70 (D=>S) |
| hPRR13-12 | H73 + H76 | L70 (D=>S) |
| hPRR13-13 | wt | L47 + L70 |
| hPRR13-14 | H73 (T=>K) | L47 + L70 |
| hPRR13-15 | H76 (G=>S) | L47 + L70 |
| hPRR13-16 | H73 + H76 | L47 + L70 |

| Name | Framework Mutation H | Framework Mutation L |
|---|---|---|
| hC6-17-1 | wt | wt |
| hC6-17-2 | wt | L87 (Y=>S) |
| hC6-17-3 | H71 (R=>V) | wt |
| hC6-17-4 | H71 (R=>V) | L87 (Y=>S) |
| hC6-17-5 | H73 (T=>R) | wt |
| hC6-17-6 | H73 (T=>R) | L87 (Y=>S) |
| hC6-17-7 | H76 (=>R-S) | wt |
| hC6-17-8 | H76 (=>R-S) | L87 (Y=>S) |
| hC6-17-9 | H71 +H73 | wt |
| hC6-17-10 | H71 +H73 | L87 (Y=>S) |
| hC6-17-11 | H71 + H76 | wt |
| hC6-17-12 | H71 + H76 | L87 (Y=>S) |
| hC6-17-13 | H73 + H76 | wt |
| hC6-17-14 | H73 + H76 | L87 (Y=>S) |
| hC6-17-15 | H71 + H73 + H76 | wt |
| hC6-17-16 | H71 + H73 + H76 | L87 (Y=>S) |

SEQUENCE LISTING

<160> NUMBER OF SEQ ID NOS: 101

<210> SEQ ID NO 1
<211> LENGTH: 18
<212> TYPE: PRT
<213> ORGANISM: Artificial Sequence
<220> FEATURE:
<223> OTHER INFORMATION: Huntingtin peptide -continued

<400> SEQUENCE: 1

Leu Pro Gln Pro Pro Pro Gln Ala Gln Pro Leu Pro Gln Pro Gln
1               5                   10                  15

Pro Cys

<210> SEQ ID NO 2
<211> LENGTH: 11
<212> TYPE: PRT
<213> ORGANISM: Artificial Sequence
<220> FEATURE:
<223> OTHER INFORMATION: Huntingtin peptide

<400> SEQUENCE: 2

Cys Pro Ser Asp Ser Ser Glu Ile Val Leu Asp
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 3

Gly Thr Asp Asn Gln Tyr Leu Gly Leu Gln Ile Gly Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 4

Leu Pro Gln Pro Pro Pro Gln Ala Gln Pro Leu Leu Pro Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 5

Cys Gly Pro Ala Val Ala Glu Glu Pro Leu His Arg Pro
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 6

Ser Asp Ser Ser Glu Ile Val Leu Asp Gly Thr Asp Cys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 7

Glu Ile Val Leu Asp Gly Thr Asp Asn Gln Tyr Leu Cys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 8

Ile Val Leu Asp Gly Thr Asp Asn Gln Tyr Leu Gly Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 9

Val Leu Asp Gly Thr Asp Asn Gln Tyr Leu Gly Leu Cys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 10

Leu Asp Gly Thr Asp Asn Gln Tyr Leu Gly Leu Gln Cys
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 11

Asp Gly Thr Asp Asn Gln Tyr Leu Gly Leu Gln Ile Gly Cys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 12

Cys Thr Asp Asn Gln Tyr Leu Gly Leu Gln Ile Gly Gln
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 13

Cys Gly Thr Asp Asn Gln Tyr Leu Gly Leu Gln Ile Gly
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 14

Cys Asp Asn Gln Tyr Leu Gly Leu Gln Ile Gly Gln Pro
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 15

Cys Asn Gln Tyr Leu Gly Leu Gln Ile Gly Gln Pro Gln
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Huntingtin peptide

<400> SEQUENCE: 16

Cys Pro Gln Leu Pro Gln Pro Pro Pro Gln Ala Gln Pro Leu Leu Pro
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 17

Thr Asp Asn Gln Tyr Leu Gly Leu Gln Ile Gly Gln Cys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 18

Asp Asn Gln Tyr Leu Gly Leu Gln Ile Gly Gln Pro Cys
1               5                   10

<210> SEQ ID NO 19
<211> LENGTH: 23
<212> TYPE: PRT
<213> ORGANISM: Artificial Sequence
<220> FEATURE:
<223> OTHER INFORMATION: Huntingtin peptide
<220> FEATURE:
<221> NAME/KEY: misc_feature

```
<222> LOCATION: (22)..(22)
<223> OTHER INFORMATION: Xaa can be any naturally occurring amino acid

<400> SEQUENCE: 19

Pro Pro Pro Gln Leu Pro Gln Pro Pro Gln Ala Gln Pro Leu Leu
1               5                   10                  15

Pro Gln Pro Gln Pro Xaa Cys
            20

<210> SEQ ID NO 20
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 20

Pro Ser Asp Ser Ser Glu Ile Val Leu Asp Gly Thr Cys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 21

Asp Ser Ser Glu Ile Val Leu Asp Gly Thr Asp Asn Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 22

Ser Glu Ile Val Leu Asp Gly Thr Asp Asn Gln Tyr Cys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 23

Asn Gln Tyr Leu Gly Leu Gln Ile Gly Gln Pro Gln Cys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 24

Gln Tyr Leu Gly Leu Gln Ile Gly Gln Pro Gln Asp Cys
1               5                   10

<210> SEQ ID NO 25
<211> LENGTH: 20
```

```
<212> TYPE: PRT
<213> ORGANISM: Artificial Sequence
<220> FEATURE:
<223> OTHER INFORMATION: Huntingtin peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 25

Cys Xaa Met Ala Thr Leu Glu Lys Leu Met Lys Ala Phe Glu Ser Leu
1               5                   10                  15

Lys Ser Phe Gln
            20

<210> SEQ ID NO 26
<211> LENGTH: 15
<212> TYPE: PRT
<213> ORGANISM: Artificial Sequence
<220> FEATURE:
<223> OTHER INFORMATION: Huntingtin peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 26

Cys Xaa Lys Leu Met Lys Ala Phe Glu Ser Leu Lys Ser Phe Gln
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 27

Cys Glu Glu Gln Gln Arg Gln Gln Gln Gln Gln Gln Gln
1               5                   10

<210> SEQ ID NO 28
<211> LENGTH: 19
<212> TYPE: PRT
<213> ORGANISM: Artificial Sequence
<220> FEATURE:
<223> OTHER INFORMATION: Huntingtin peptide
<220> FEATURE:
<221> NAME/KEY: MOD_RES
<222> LOCATION: (15)..(15)
<223> OTHER INFORMATION: bAla

<400> SEQUENCE: 28

Gln Gln Gln Gln Gln Gln Pro Pro Pro Pro Pro Pro Pro Xaa Lys
1               5                   10                  15

Lys Lys Cys

<210> SEQ ID NO 29
<211> LENGTH: 7
<212> TYPE: PRT
<213> ORGANISM: Artificial Sequence
<220> FEATURE:
<223> OTHER INFORMATION: Huntingtin peptide

<400> SEQUENCE: 29

Cys Ser Glu Ile Val Leu Asp
1               5
```

```
<210> SEQ ID NO 30
<211> LENGTH: 8
<212> TYPE: PRT
<213> ORGANISM: Artificial Sequence
<220> FEATURE:
<223> OTHER INFORMATION: Huntingtin peptide

<400> SEQUENCE: 30

Cys Ser Ser Glu Ile Val Leu Asp
1               5

<210> SEQ ID NO 31
<211> LENGTH: 9
<212> TYPE: PRT
<213> ORGANISM: Artificial Sequence
<220> FEATURE:
<223> OTHER INFORMATION: Huntingtin peptide

<400> SEQUENCE: 31

Cys Asp Ser Ser Glu Ile Val Leu Asp
1               5

<210> SEQ ID NO 32
<211> LENGTH: 10
<212> TYPE: PRT
<213> ORGANISM: Artificial Sequence
<220> FEATURE:
<223> OTHER INFORMATION: Huntingtin peptide

<400> SEQUENCE: 32

Cys Ser Asp Ser Ser Glu Ile Val Leu Asp
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Huntingtin peptide

<400> SEQUENCE: 33

Cys Glu Ile Val Leu Asp
1               5

<210> SEQ ID NO 34
<211> LENGTH: 5
<212> TYPE: PRT
<213> ORGANISM: Artificial Sequence
<220> FEATURE:
<223> OTHER INFORMATION: Huntingtin peptide

<400> SEQUENCE: 34

Cys Ile Val Leu Asp
1               5

<210> SEQ ID NO 35
<211> LENGTH: 6
<212> TYPE: PRT
<213> ORGANISM: Artificial Sequence
<220> FEATURE:
<223> OTHER INFORMATION: Huntingtin peptide

<400> SEQUENCE: 35

Cys Ser Glu Ile Val Leu
1               5
```

```
<210> SEQ ID NO 36
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 36

Cys Ser Glu Ile Val Leu Asp Gly Thr Asp Asn Gln Tyr Leu
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 37

Cys Ser Asp Ser Ser Glu Ile Val Leu Asp Gly Thr Asp Asn
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 38

Ser Glu Ile Val Leu Asp Gly Thr Asp Asn Gln Tyr Leu Cys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 39

Cys Ala Glu Ile Val Leu Asp Gly Thr Asp Asn Gln Tyr Leu
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 40

Cys Ser Ala Ile Val Leu Asp Gly Thr Asp Asn Gln Tyr Leu
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 41

Cys Ser Glu Ala Val Leu Asp Gly Thr Asp Asn Gln Tyr Leu
1               5                   10

<210> SEQ ID NO 42
```

```
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 42

Cys Ser Glu Ile Ala Leu Asp Gly Thr Asp Asn Gln Tyr Leu
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 43

Cys Ser Glu Ile Val Ala Asp Gly Thr Asp Asn Gln Tyr Leu
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 44

Cys Ser Glu Ile Val Leu Ala Gly Thr Asp Asn Gln Tyr Leu
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 45

Cys Ser Glu Ile Val Leu Asp Ala Thr Asp Asn Gln Tyr Leu
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 46

Cys Ser Glu Ile Val Leu Asp Gly Ala Asp Asn Gln Tyr Leu
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 47

Cys Ser Glu Ile Val Leu Asp Gly Thr Ala Asn Gln Tyr Leu
1               5                   10

<210> SEQ ID NO 48
<211> LENGTH: 14
```

```
<212> TYPE: PRT
<213> ORGANISM: Artificial Sequence
<220> FEATURE:
<223> OTHER INFORMATION: Huntingtin peptide

<400> SEQUENCE: 48

Cys Ser Glu Ile Val Leu Asp Gly Thr Asp Ala Gln Tyr Leu
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 49

Cys Ser Glu Ile Val Leu Asp Gly Thr Asp Asn Ala Tyr Leu
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 50

Cys Ser Glu Ile Val Leu Asp Gly Thr Asp Asn Gln Ala Leu
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 51

Cys Ser Glu Ile Val Leu Asp Gly Thr Asp Asn Gln Tyr Ala
1               5                   10

<210> SEQ ID NO 52
<211> LENGTH: 43
<212> TYPE: PRT
<213> ORGANISM: Artificial Sequence
<220> FEATURE:
<223> OTHER INFORMATION: Huntingtin peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 52

Xaa Gly Gly Gly Asp Tyr Lys Asp Asp Asp Lys Gly Ala Val Thr
1               5                   10                  15

Pro Ser Asp Ser Ser Glu Ile Val Leu Asp Gly Thr Asp Asn Gln Tyr
            20                  25                  30

Leu Gly Leu Gln Ile Gly Gln Pro Gln Asp Gly
        35                  40

<210> SEQ ID NO 53
<211> LENGTH: 35
<212> TYPE: PRT
<213> ORGANISM: Artificial Sequence
<220> FEATURE:
<223> OTHER INFORMATION: Huntingtin peptide
```

```
<220> FEATURE:
<221> NAME/KEY: misc_feature
<222> LOCATION: (1)..(1)
<223> OTHER INFORMATION: Xaa can be any naturally occurring amino acid

<400> SEQUENCE: 53

Xaa Gly Gly Gly Asp Tyr Lys Asp Asp Asp Lys Gly Pro Pro Pro
1               5                   10                  15

Gln Leu Pro Gln Pro Pro Pro Gln Ala Gln Pro Leu Leu Pro Gln Pro
            20                  25                  30

Gln Pro Gly
        35

<210> SEQ ID NO 54
<211> LENGTH: 8
<212> TYPE: PRT
<213> ORGANISM: Artificial Sequence
<220> FEATURE:
<223> OTHER INFORMATION: antibody sequence

<400> SEQUENCE: 54

Gly Tyr Ser Phe Thr Asp Phe Tyr
1               5

<210> SEQ ID NO 55
<211> LENGTH: 8
<212> TYPE: PRT
<213> ORGANISM: Artificial Sequence
<220> FEATURE:
<223> OTHER INFORMATION: antibody sequence

<400> SEQUENCE: 55

Ile Asp Pro Lys Asn Gly Asp Thr
1               5

<210> SEQ ID NO 56
<211> LENGTH: 10
<212> TYPE: PRT
<213> ORGANISM: Artificial Sequence
<220> FEATURE:
<223> OTHER INFORMATION: antibody sequence

<400> SEQUENCE: 56

Ala Thr Tyr Tyr Gly Tyr Thr Met Asp Tyr
1               5                   10

<210> SEQ ID NO 57
<211> LENGTH: 7
<212> TYPE: PRT
<213> ORGANISM: Artificial Sequence
<220> FEATURE:
<223> OTHER INFORMATION: antibody sequence

<400> SEQUENCE: 57

Ser Ser Val Thr Ser Ser Tyr
1               5

<210> SEQ ID NO 58
<211> LENGTH: 3
<212> TYPE: PRT
<213> ORGANISM: Artificial Sequence
<220> FEATURE:
<223> OTHER INFORMATION: antibody sequence

<400> SEQUENCE: 58

Ser Thr Ser
1
```

<210> SEQ ID NO 59
<211> LENGTH: 9
<212> TYPE: PRT
<213> ORGANISM: Artificial Sequence
<220> FEATURE:
<223> OTHER INFORMATION: antibody sequence

<400> SEQUENCE: 59

His Gln Tyr Arg Arg Pro Pro Arg Thr
1               5

<210> SEQ ID NO 60
<211> LENGTH: 146
<212> TYPE: PRT
<213> ORGANISM: Artificial Sequence
<220> FEATURE:
<223> OTHER INFORMATION: antibody sequence

<400> SEQUENCE: 60

Met Gly Trp Ser Cys Ile Met Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Thr Phe
        35                  40                  45

Thr Glu Tyr Thr Met His Trp Val Lys Gln Ser His Gly Lys Ser Leu
    50                  55                  60

Glu Trp Ile Gly Gly Ile Asn Pro Asn Asn Gly Gly Thr Arg Tyr Asn
65                  70                  75                  80

Gln Lys Phe Lys Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Ser Leu Asp Gly Arg Asp Tyr Trp Gly Gln Gly Thr
        115                 120                 125

Thr Leu Thr Val Ser Ser Ala Lys Thr Thr Ala Pro Ser Val Phe Pro
    130                 135                 140

Leu Ala
145

<210> SEQ ID NO 61
<211> LENGTH: 162
<212> TYPE: PRT
<213> ORGANISM: Artificial Sequence
<220> FEATURE:
<223> OTHER INFORMATION: antibody sequence

<400> SEQUENCE: 61

Met Val Leu Met Leu Leu Leu Trp Val Ser Gly Thr Cys Gly Asp
1               5                   10                  15

Ile Val Met Ser Gln Ser Pro Ser Ser Leu Ala Val Ser Ala Gly Glu
            20                  25                  30

Lys Val Thr Met Ser Cys Lys Ser Ser Gln Ser Leu Leu Asn Ser Arg
        35                  40                  45

Thr Arg Lys Asn Tyr Leu Ala Trp Tyr Gln Gln Lys Pro Gly Gln Ser
    50                  55                  60

Pro Lys Leu Leu Ile Tyr Trp Ala Ser Thr Arg Glu Ser Gly Val Pro
65                  70                  75                  80

```
Asp Arg Phe Thr Gly Ser Gly Ser Gly Thr Asp Phe Thr Leu Thr Ile
                85                  90                  95

Ser Ser Val Gln Ala Glu Asp Leu Ala Val Tyr Ser Cys Lys Gln Ser
            100                 105                 110

Tyr Asn Leu Leu Thr Phe Gly Ala Gly Thr Lys Leu Glu Leu Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys

<210> SEQ ID NO 62
<211> LENGTH: 169
<212> TYPE: PRT
<213> ORGANISM: Artificial Sequence
<220> FEATURE:
<223> OTHER INFORMATION: antibody sequence

<400> SEQUENCE: 62

Met Gly Trp Ser Trp Val Met Leu Phe Leu Leu Ser Gly Thr Gly Gly
1               5                   10                  15

Val Leu Ser Glu Val Gln Leu Gln Gln Ser Ala Pro Glu Leu Val Lys
            20                  25                  30

Pro Gly Ala Ser Val Lys Met Ser Cys Lys Ala Ser Gly Tyr Ser Phe
        35                  40                  45

Thr Asp Phe Tyr Met Lys Trp Val Lys Gln Ser His Gly Lys Gly Leu
    50                  55                  60

Glu Trp Ile Gly Asp Ile Asp Pro Lys Asn Gly Asp Thr Phe Tyr Asn
65                  70                  75                  80

Gln Lys Phe Lys Gly Arg Ala Thr Leu Thr Val Asp Lys Ser Ser Ser
                85                  90                  95

Thr Ala Tyr Met Gln Leu Asn Ser Leu Thr Glu Asp Ser Ala Val
            100                 105                 110

Tyr Tyr Cys Ala Thr Tyr Tyr Gly Tyr Thr Met Asp Tyr Trp Gly Gln
            115                 120                 125

Gly Thr Ser Val Thr Val Ser Ser Ala Lys Thr Thr Ala Pro Ser Val
        130                 135                 140

Tyr Pro Leu Ala Pro Val Cys Gly Asp Thr Thr Gly Ser Ser Val Thr
145                 150                 155                 160

Leu Gly Cys Leu Val Lys Gly Tyr Phe
                165

<210> SEQ ID NO 63
<211> LENGTH: 165
<212> TYPE: PRT
<213> ORGANISM: Artificial Sequence
<220> FEATURE:
<223> OTHER INFORMATION: antibody sequence

<400> SEQUENCE: 63

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45
```

```
Ser Ser Val Thr Ser Ser Tyr Leu His Trp Tyr Gln Gln Lys Pro Gly
 50                  55                  60

Ser Ser Pro Lys Leu Trp Ile Tyr Ser Thr Ser Asn Leu Ala Ser Gly
 65                  70                  75                  80

Val Pro Ala Arg Phe Ser Gly Ser Gly Ser Gly Thr Ser Tyr Ser Leu
                 85                  90                  95

Thr Ile Ser Ser Met Glu Ala Glu Asp Ala Ala Thr Tyr Tyr Cys His
             100                 105                 110

Gln Tyr Arg Arg Pro Pro Arg Thr Phe Gly Gly Gly Thr Lys Leu Glu
         115                 120                 125

Ile Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Arg
                165

<210> SEQ ID NO 64
<211> LENGTH: 152
<212> TYPE: PRT
<213> ORGANISM: Artificial Sequence
<220> FEATURE:
<223> OTHER INFORMATION: antibody sequence

<400> SEQUENCE: 64

Met Asp Phe Gly Leu Ser Trp Val Phe Phe Val Val Phe Tyr Gln Gly
  1               5                  10                  15

Val His Cys Glu Val Gln Leu Val Glu Ser Gly Gly Gly Leu Val Gln
             20                  25                  30

Pro Lys Gly Ser Leu Lys Leu Ser Cys Ala Ala Ser Gly Phe Thr Phe
         35                  40                  45

Asn Thr Tyr Ala Met Asn Trp Val Arg Gln Ala Pro Gly Lys Gly Leu
     50                  55                  60

Glu Trp Val Ala Arg Ile Arg Ser Lys Ser Asn Asn Tyr Ala Thr Tyr
 65                  70                  75                  80

Tyr Ala Asp Ser Val Lys Asp Arg Phe Thr Ile Ser Arg Asp Asp Ser
                 85                  90                  95

Gln Ser Met Leu Tyr Leu Gln Met Asn Asn Leu Lys Thr Glu Asp Thr
             100                 105                 110

Ala Met Tyr Tyr Cys Val Arg His Gly Glu Tyr Gly Asn Pro Trp Phe
         115                 120                 125

Ala Tyr Trp Gly Gln Gly Thr Leu Val Thr Val Ser Ala Glu Ser Gln
130                 135                 140

Ser Phe Pro Asn Val Phe Pro Leu
145                 150

<210> SEQ ID NO 65
<211> LENGTH: 166
<212> TYPE: PRT
<213> ORGANISM: Artificial Sequence
<220> FEATURE:
<223> OTHER INFORMATION: antibody sequence

<400> SEQUENCE: 65

Met Lys Leu Pro Val Arg Leu Leu Val Leu Met Phe Trp Ile Pro Ala
  1               5                  10                  15

Ser Ser Ser Asp Val Val Met Thr Gln Thr Pro Leu Ser Leu Pro Val
```

```
                20                  25                  30
Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165

<210> SEQ ID NO 66
<211> LENGTH: 8
<212> TYPE: PRT
<213> ORGANISM: Artificial Sequence
<220> FEATURE:
<223> OTHER INFORMATION: antibody sequence

<400> SEQUENCE: 66

Gly Tyr Thr Phe Thr Glu Tyr Thr
1               5

<210> SEQ ID NO 67
<211> LENGTH: 8
<212> TYPE: PRT
<213> ORGANISM: Artificial Sequence
<220> FEATURE:
<223> OTHER INFORMATION: antibody sequence

<400> SEQUENCE: 67

Ile Asn Pro Asn Asn Gly Gly Thr
1               5

<210> SEQ ID NO 68
<211> LENGTH: 8
<212> TYPE: PRT
<213> ORGANISM: Artificial Sequence
<220> FEATURE:
<223> OTHER INFORMATION: antibody sequence

<400> SEQUENCE: 68

Ala Ser Leu Asp Gly Arg Asp Tyr
1               5

<210> SEQ ID NO 69
<211> LENGTH: 12
<212> TYPE: PRT
<213> ORGANISM: Artificial Sequence
<220> FEATURE:
<223> OTHER INFORMATION: antibody sequence

<400> SEQUENCE: 69

Gln Ser Leu Leu Asn Ser Arg Thr Arg Lys Asn Tyr
```

```
<210> SEQ ID NO 70
<211> LENGTH: 4
<212> TYPE: PRT
<213> ORGANISM: Artificial Sequence
<220> FEATURE:
<223> OTHER INFORMATION: antibody sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 70

Trp Ala Ser Xaa
1

<210> SEQ ID NO 71
<211> LENGTH: 8
<212> TYPE: PRT
<213> ORGANISM: Artificial Sequence
<220> FEATURE:
<223> OTHER INFORMATION: antibody sequence

<400> SEQUENCE: 71

Lys Gln Ser Tyr Asn Leu Leu Thr
1               5

<210> SEQ ID NO 72
<211> LENGTH: 8
<212> TYPE: PRT
<213> ORGANISM: Artificial Sequence
<220> FEATURE:
<223> OTHER INFORMATION: antibody sequence

<400> SEQUENCE: 72

Gly Phe Thr Phe Asn Thr Tyr Ala
1               5

<210> SEQ ID NO 73
<211> LENGTH: 10
<212> TYPE: PRT
<213> ORGANISM: Artificial Sequence
<220> FEATURE:
<223> OTHER INFORMATION: antibody sequence

<400> SEQUENCE: 73

Ile Arg Ser Lys Ser Asn Asn Tyr Ala Thr
1               5                   10

<210> SEQ ID NO 74
<211> LENGTH: 13
<212> TYPE: PRT
<213> ORGANISM: Artificial Sequence
<220> FEATURE:
<223> OTHER INFORMATION: antibody sequence

<400> SEQUENCE: 74

Val Arg His Gly Glu Tyr Gly Asn Pro Trp Phe Ala Tyr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: antibody sequence
```

```
<400> SEQUENCE: 75

Gln Ser Leu Val His Ser Asn Gly Asn Thr Tyr
1               5                   10

<210> SEQ ID NO 76
<211> LENGTH: 4
<212> TYPE: PRT
<213> ORGANISM: Artificial Sequence
<220> FEATURE:
<223> OTHER INFORMATION: antibody sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 76

Lys Val Ser Xaa
1

<210> SEQ ID NO 77
<211> LENGTH: 9
<212> TYPE: PRT
<213> ORGANISM: Artificial Sequence
<220> FEATURE:
<223> OTHER INFORMATION: antibody sequence

<400> SEQUENCE: 77

Ser Gln Ser Thr His Val Pro Tyr Thr
1               5

<210> SEQ ID NO 78
<211> LENGTH: 5
<212> TYPE: PRT
<213> ORGANISM: Artificial Sequence
<220> FEATURE:
<223> OTHER INFORMATION: core epitope

<400> SEQUENCE: 78

Leu Leu Pro Gln Pro
1               5

<210> SEQ ID NO 79
<211> LENGTH: 7
<212> TYPE: PRT
<213> ORGANISM: Artificial Sequence
<220> FEATURE:
<223> OTHER INFORMATION: core epitope

<400> SEQUENCE: 79

Pro Pro Gln Ala Gln Pro Leu
1               5

<210> SEQ ID NO 80
<211> LENGTH: 6
<212> TYPE: PRT
<213> ORGANISM: Artificial Sequence
<220> FEATURE:
<223> OTHER INFORMATION: core epitope

<400> SEQUENCE: 80

Pro Pro Gln Ala Gln Pro
1               5

<210> SEQ ID NO 81
<211> LENGTH: 4
<212> TYPE: PRT
<213> ORGANISM: Artificial Sequence
```

```
<220> FEATURE:
<223> OTHER INFORMATION: core epitope

<400> SEQUENCE: 81

Gln Pro Leu Leu
1

<210> SEQ ID NO 82
<211> LENGTH: 7
<212> TYPE: PRT
<213> ORGANISM: Artificial Sequence
<220> FEATURE:
<223> OTHER INFORMATION: core epitope

<400> SEQUENCE: 82

Pro Gln Ala Gln Pro Leu Leu
1               5

<210> SEQ ID NO 83
<211> LENGTH: 8
<212> TYPE: PRT
<213> ORGANISM: Artificial Sequence
<220> FEATURE:
<223> OTHER INFORMATION: core epitope

<400> SEQUENCE: 83

Gln Tyr Leu Gly Leu Gln Ile Gly
1               5

<210> SEQ ID NO 84
<211> LENGTH: 7
<212> TYPE: PRT
<213> ORGANISM: Artificial Sequence
<220> FEATURE:
<223> OTHER INFORMATION: core epitope

<400> SEQUENCE: 84

Tyr Leu Gly Leu Gln Ile Gly
1               5

<210> SEQ ID NO 85
<211> LENGTH: 10
<212> TYPE: PRT
<213> ORGANISM: Artificial Sequence
<220> FEATURE:
<223> OTHER INFORMATION: core epitope

<400> SEQUENCE: 85

Asp Asn Gln Tyr Leu Gly Leu Gln Ile Gly
1               5                   10

<210> SEQ ID NO 86
<211> LENGTH: 7
<212> TYPE: PRT
<213> ORGANISM: Artificial Sequence
<220> FEATURE:
<223> OTHER INFORMATION: core epitope

<400> SEQUENCE: 86

Asp Asn Gln Tyr Leu Gly Leu
1               5

<210> SEQ ID NO 87
<211> LENGTH: 7
<212> TYPE: PRT
<213> ORGANISM: Artificial Sequence
<220> FEATURE:
```

<223> OTHER INFORMATION: core epitope

<400> SEQUENCE: 87

Tyr Leu Gly Leu Gln Ile Gly
1               5

<210> SEQ ID NO 88
<211> LENGTH: 10
<212> TYPE: PRT
<213> ORGANISM: Artificial Sequence
<220> FEATURE:
<223> OTHER INFORMATION: immunogenic peptide

<400> SEQUENCE: 88

Asp Asn Gln Tyr Leu Gly Leu Gln Ile Cys
1               5                   10

<210> SEQ ID NO 89
<211> LENGTH: 11
<212> TYPE: PRT
<213> ORGANISM: Artificial Sequence
<220> FEATURE:
<223> OTHER INFORMATION: immunogenic peptide

<400> SEQUENCE: 89

Thr Asp Asn Gln Tyr Leu Gly Leu Gln Ile Cys
1               5                   10

<210> SEQ ID NO 90
<211> LENGTH: 12
<212> TYPE: PRT
<213> ORGANISM: Artificial Sequence
<220> FEATURE:
<223> OTHER INFORMATION: immunogenic peptide

<400> SEQUENCE: 90

Thr Asp Asn Gln Tyr Leu Gly Leu Gln Ile Gly Cys
1               5                   10

<210> SEQ ID NO 91
<211> LENGTH: 14
<212> TYPE: PRT
<213> ORGANISM: Artificial Sequence
<220> FEATURE:
<223> OTHER INFORMATION: immunogenic peptide

<400> SEQUENCE: 91

Lys Thr Asp Asn Gln Tyr Leu Gly Leu Gln Ile Gly Lys Cys
1               5                   10

<210> SEQ ID NO 92
<211> LENGTH: 15
<212> TYPE: PRT
<213> ORGANISM: Artificial Sequence
<220> FEATURE:
<223> OTHER INFORMATION: immunogenic peptide

<400> SEQUENCE: 92

Gly Thr Asp Asn Gln Tyr Leu Gly Leu Gln Ile Gly Lys Lys Cys
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: immunogenic peptide

```
<400> SEQUENCE: 93

Lys Thr Asp Asn Gln Tyr Leu Gly Leu Gln Ile Lys Lys Gly Cys
 1               5                  10                  15

<210> SEQ ID NO 94
<211> LENGTH: 14
<212> TYPE: PRT
<213> ORGANISM: Artificial Sequence
<220> FEATURE:
<223> OTHER INFORMATION: immunogenic peptide

<400> SEQUENCE: 94

Lys Asp Asn Gln Tyr Leu Gly Leu Gln Ile Lys Lys Gly Cys
 1               5                  10

<210> SEQ ID NO 95
<211> LENGTH: 109
<212> TYPE: PRT
<213> ORGANISM: Artificial Sequence
<220> FEATURE:
<223> OTHER INFORMATION: humanised antibody sequence

<400> SEQUENCE: 95

Glu Ile Val Leu Thr Gln Ser Pro Ser Ser Leu Ser Ala Ser Val Gly
 1               5                  10                  15

Asp Arg Val Thr Ile Thr Cys Thr Ala Ser Ser Val Thr Ser Ser
                20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys His Gln Tyr Arg Arg Pro Pro
                85                  90                  95

Arg Thr Phe Gly Gly Gly Thr Lys Leu Glu Ile Lys Arg
                100                 105

<210> SEQ ID NO 96
<211> LENGTH: 117
<212> TYPE: PRT
<213> ORGANISM: Artificial Sequence
<220> FEATURE:
<223> OTHER INFORMATION: humanised antibody sequence

<400> SEQUENCE: 96

Glu Val Gln Leu Val Glu Ser Gly Pro Glu Val Lys Lys Pro Gly Ala
 1               5                  10                  15

Thr Val Lys Ile Ser Cys Lys Val Ser Gly Tyr Thr Phe Thr Asp Phe
                20                  25                  30

Tyr Met Lys Trp Val Gln Ala Pro Gly Arg Gly Leu Glu Trp Met
            35                  40                  45

Gly Asp Ile Asp Pro Lys Asn Gly Asp Thr Phe Tyr Asn Gln Lys Phe
        50                  55                  60

Lys Gly Arg Val Thr Met Thr Ala Asp Thr Ser Thr Gly Thr Ala Tyr
65                  70                  75                  80

Met Gln Leu Ser Ser Leu Thr Ser Glu Asp Thr Ala Val Tyr Phe Cys
                85                  90                  95

Ala Ser Tyr Tyr Gly Tyr Thr Met Asp Tyr Trp Gly Gln Gly Thr Thr
```

Val Thr Val Ala Ser
        115

<210> SEQ ID NO 97
<211> LENGTH: 112
<212> TYPE: PRT
<213> ORGANISM: Artificial Sequence
<220> FEATURE:
<223> OTHER INFORMATION: humanised antibody sequence

<400> SEQUENCE: 97

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gly Gly Thr Lys Leu Glu Ile Lys
            100                 105                 110

<210> SEQ ID NO 98
<211> LENGTH: 115
<212> TYPE: PRT
<213> ORGANISM: Artificial Sequence
<220> FEATURE:
<223> OTHER INFORMATION: humanised antibody sequence

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Arg Gly Leu Glu Trp Met
        35                  40                  45

Gly Gly Ile Asn Pro Asn Asn Gly Gly Thr Arg Tyr Asn Gln Lys Phe
    50                  55                  60

Lys Gly Arg Val Thr Met Thr Arg Asp Thr Ser Ile Arg Thr Ala Tyr
65                  70                  75                  80

Val Glu Leu Ser Arg Leu Thr Ser Asp Asp Thr Ala Val Tyr Tyr Cys
                85                  90                  95

Ala Ser Leu Asp Gly Arg Asp Tyr Trp Gly Gln Gly Thr Leu Val Thr
            100                 105                 110

Val Ser Ser
        115

<210> SEQ ID NO 99
<211> LENGTH: 9
<212> TYPE: PRT
<213> ORGANISM: Artificial Sequence
<220> FEATURE:
<223> OTHER INFORMATION: Huntingtin peptide

<400> SEQUENCE: 99

```
Cys Ser Glu Ile Val Leu Asp Gly Thr
1               5

<210> SEQ ID NO 100
<211> LENGTH: 4
<212> TYPE: PRT
<213> ORGANISM: Artificial Sequence
<220> FEATURE:
<223> OTHER INFORMATION: synthetic linker

<400> SEQUENCE: 100

Lys Lys Cys Gly
1

<210> SEQ ID NO 101
<211> LENGTH: 4
<212> TYPE: PRT
<213> ORGANISM: Artificial Sequence
<220> FEATURE:
<223> OTHER INFORMATION: synthetic linker

<400> SEQUENCE: 101

Lys Lys Gly Cys
1
```

SUBSTANCES AND METHODS FOR THE USE IN PREVENTION AND/OR TREATMENT IN HUNTINGTON'S DISEASE

The present invention relates to providing substances and methods for use in the treatment and prevention of Huntington's disease.

Huntington's disease is a rare monogenetic disorder with an autosomal dominant mode of inheritance. It is caused by a CAG trinucleotide repeat expansion within the coding region of the Huntingtin (HTT) gene on human chromosome 4 (Novak & Tabrizi, 2011). The causative CAG repeat expansion is associated with genetic instability during replication and changes in RNA splicing. Most importantly however, the encoded protein is changed in structure due to an expanded polyglutamine (polyQ) tract in the N-terminal portion of the protein leading to accumulation of structurally changed and modified Huntingtin protein and protein fragments in the brain and other organs or cells over time. This process resembles other neurodegenerative proteinopathies such as e.g. Alzheimer's- or Parkinson's disease or Multiple System Atrophy where the common denominator is the formation of aggregates or protein fibrils combined with protein degradation products. In Huntington's disease, the pathological hallmark is progressive neurodegeneration mainly of the striatum and cortex with accumulation of aggregated and degraded Huntingtin protein.

The clinical symptoms of Huntington's disease progress in a predictable manner starting subtly with mood changes or cognition problems followed by unsteady gait and motoric problems. With time, physical abilities deteriorate with manifest movement coordination problems combined with a decline in mental abilities and psychiatric and behavioral problems. Average life expectancy is around twenty years after first clinical manifestation. Symptoms can vary significantly and it has been well documented that the age of onset inversely correlates with the number of CAG repeats in the mutant Huntingtin gene corroborating the causative role of mutated Huntingtin.

There is no cure or prevention for Huntington's disease. To control the symptoms, full-time patient care is required in the later stages of the disease and the burden for the patient and his social environment is substantial. Symptomatic treatments such as pharmaceutical and non-drug treatments can relieve some of the symptoms.

With the current understanding of Huntington's disease etiology and genetic cause, mutant Huntingtin is regarded as prime target for disease modifying targeting strategies although not in the conventional way (Yu et al., 2014). Based on clinical genetics and functional evidence from animal models (Bard et al., 2014), Huntingtin lowering strategies are regarded as approaches of paramount importance despite molecular challenges associated with such a concept (Zheng & Diamond, 2012). Current strategies are typically hampered by the lack of delivery of the therapeutic agent to the targeting site within affected neurons in the brain. This counts for DNA or mRNA targeting approaches currently under development (Davidson, 2012) including antisense oligonucleotides, siRNAs, and gene therapy using viral delivery of miRNAs, shRNAs or ZFPs (to target at the gene level) or indirect, small molecule-based approaches such as SirT1 or mTOR inhibition. An alternative approach consists of using intrabodies provided by viral vectors targeting intracellular Huntingtin in the brain (Butler et al., 2012). Despite their proven functionality in preclinical models, most of these approaches are facing major delivery challenges to the targeting site. In addition, "foreign" large molecule structures such as scFv-based intrabodies (Messer & Joshi, 2013) carry the risk of potentially constituting new epitopes to the host thereby inducing undesired humoral immune responses against the therapeutic agent or undesired autoreactive T-cell responses against the cells expressing and presenting "foreign" protein.

WO 2012/140376 A1 discloses therapeutic peptides pep4 and pep42, both peptides do not extend to the c6 cleavage site of HTT. These peptides were suggested for use as HTT aggregation inhibitors and not related to any vaccination or immunological application. WO 2010/015592 A2 discloses the generation of monoclonal antibodies for the purpose of diagnostic quantification. One of these monoclonal antibodies (4C9) was generated for the purpose of detection/quantification assays for mutated polyQ protein but not for any therapeutic application. The antibody was generated using a peptide with amino acids 65 to 84 derived from the HTT protein sequence. Ko et al. (Brain Res. Bull. 56 (2001): 319-329) disclose anti-HTT monoclonal antibodies, most binding to the polyQ domain of HTT. Persichetti et al. (Mol. Med. 1 (1995): 374-383) disclose antibody-eliciting peptides HP1 and HP12. Miller et al. (Mol. Ther. 7(2003), 572-579) discloses DNA vaccination with DNA encoding for the first 17 AA plus 103 Glutamine residues fused to a GFP protein.

US 2007/0026029 A1 discloses an apheresis device to treat and prevent Alzheimer's disease. Weiss et al. (Anal. Biochem. 395(2009): 8-15) disclose detection methods for mutant HTT in animal and human tissue. Butler et al. (Prog. Neurobiol. 97(2011): 190-204) disclose intrabody therapies for HD in animal models based on scFv's. US 2010/0233180 A1 discloses antibodies that bind to a polyP region of HTT. Chen et al. (Chem. Biol. 18(2011): 1113-1125) suggest an expanded polyQ peptoid for HD treatment by directly binding to polyQ but not for vaccination.

In order to provide an alternative treatment approach for Huntington's disease, active and passive vaccines (e.g. antigens and antibodies) that are capable of targeting Huntingtin by simpler means are provided by the present invention. In Huntington's disease, there is increasing awareness that the condition is accompanied by generalized changes including the immune system, peripheral tissues, peripheral blood lymphocytes (PBL) and metabolism, underlining the systemic nature of this disease. As an example, pathological Huntingtin accumulation is not solely restricted to the CNS but can also be detected in peripheral blood cells (Weiss et al., 2012). By lowering Huntingtin expression in primary human macrophages/monocytes, disturbance of the innate immune system could be partially reversed by Huntingtin-targeted RNA interference (Träger et al. 2014).

Beside detection of Huntingtin within blood cells, soluble Huntingtin or Huntingtin fragments were serendipitously detected in the human plasma proteome of healthy donors (Liu et al 2007) or detected by ELISA in plasma of Glaucoma patients so far not related to Huntington's disease (Tezel et al 2012). Although the important role of the immune system in Huntington's disease has been recognized (Ellrichmann et al., 2013), a possible causative role for extracellular Huntingtin has been largely neglected. More recently, plasma and CSF Huntingtin, was merely suggested as potential biomarker for monitoring disease progression (Weiss et al., 2014). Targeting possibly pathogenic, disease promoting extracellular Huntingtin protein was not previously considered as a therapeutic target nor was it shown whether actively induced or passively administered antibodies could provide a therapeutic benefit.

It is an object of the present invention to provide new therapeutic strategies for Huntington's disease, especially strategies that are beyond the mere control of symptoms. It is another object to provide means for preventing or delaying the onset of symptoms associated with Huntington's disease.

Therefore the present invention provides peptide-based vaccines and antibodies for the treatment of Huntington's disease or delaying the onset of its clinical symptoms. The present invention therefore provides a completely new therapy concept based on the HTT protein as therapeutical target. The present invention provides an "antibody-based HTT lowering strategy" with two strategic variants that can either be applied alone or be combined: a HTT peptide-based active immunisation and/or an antibody-based passive immunisation. Both strategies can be regarded as being equivalent with regard to the therapeutic target, the HTT protein. Both strategies also apply the same (i.e. without fundamental differences) therapeutic principle and mode of action, because the active principle that combats the pathogenic HTT is finally always the antibody (either the actively created anti-HTT antibody or the passively administered antibody). This was already shown in the example section according to the present invention below by the active immunization experiments and the phagocytosis experiments with monoclonal and polyclonal antibodies clearly evidencing the same final mode of action. Both therapeutical strategies according to the present invention have not been disclosed in the prior art. HTT antibodies have—for the time being—only been used for scientific purposes and for detecting HTT in samples.

Vaccination and passive immunisation according to the present invention is a completely new approach in the treatment of Huntington's disease and is shown to be highly effective by the present invention. Immunsera and monoclonal antibodies provided with the present invention specifically recognize portions of the Huntingtin protein that have previously been shown to have different roles in the function and pathology of the protein. In particular, active vaccines induce antibodies that target defined epitopes around a previously described protease cleavage site at amino acid position 586 of the Huntingtin protein. In the following, this etiologically/functionally important cleavage region will be referred to as "caspase region 586". Graham et al., 2006 have shown that preventing protease cleavage by genetic means inhibited the phenotype in mice carrying a mutant human Huntingtin transgene. It has also been shown that other proteases might be involved in cleaving at this site in vivo (Wong et al. 2014). Since caspase cleavage is an intracellular process, a vaccination strategy targeting this region has not yet been considered or demonstrated. In addition, active vaccines induce antibodies that target defined epitopes within the so called proline rich region of the target protein.

With the present invention it is the first time proposed to target plasma Huntingtin by active or passive vaccination to combat Huntington's disease. So far, (extracellular) plasma HTT has not been considered as target for treating this disease. Moreover, mode of action mechanisms are plausibly provided by the present invention (yet, without limiting the invention to such mechanisms) by in vitro phagocytosis assay and by in vivo lowering of HTT levels in vaccinated animals and phenotypic effects in animal models providing convincing P.O.C. (proof of concept) showing that plasma HTT targeting is also beneficial in human patients.

Moreover, specific targeting regions and -derived peptides that provide a target-specific immune response are provided with the present invention which are formulated into immune response eliciting pharmaceutical compositions according to the present invention, especially for eliciting suitable antibody responses in human individuals. In the course of the present invention, core epitopes of the most relevant peptides for eliciting such immune responses are defined. The use of these core epitopes (corresponding to subfragments of the corresponding vaccination peptides) are at the centre of the immunogenic compositions and vaccines according to the present invention. The peptides used in the present invention for eliciting specific immune responses (especially as vaccines) are therefore consisting of or comprising these core epitopes and may be administered in vivo alone or in combination. In the example section, such peptides according to the present invention were already shown to be beneficial in reliable and accepted transgenic mouse models. Further, also peptides derived from the caspase region 586 of HTT are provided that are used as immunogenic compositions as well and are also used for providing and inducing antibodies (AB's) that inhibit protease cleavage such as e.g. by caspase 6 or other proteases (Wong et al. 2014). The peptides according to the present invention were also used to generate various monoclonal antibodies (mABs) that are also useful in the diagnostic and therapy of Huntington's disease, especially for passive vaccination (alone or in combination in analogy to active vaccination), as a tool for HTT level determination in biomarker evaluation/discovery and (companion-) diagnostics, as a probe for caspase 6 inhibition assay (those that inhibit caspase cleavage at caspase region 586), etc.

"Huntingtin", "Huntingtin protein" or "HTT" as used herein refers to the expression product of the Huntingtin gene. The protein details are available (and relied upon herein) under P42858 (HD_HUMAN) in the UniProtKB/Swiss-Prot database (Version 148, last modified 14 May 2014). Due to variations in the polyQ region starting at amino acid position 18 of HTT, the caspase cleavage site is referred to in the UniProt database entry as between amino acid 584 and 585. In the scientific literature and also herein, the caspase cleavage site is referred to as being between amino acid residues 586 and 587 (i.e. after "VLD" and before "GTD", i.e. between D and G). Accordingly, the "C6 cleavage region" or "C6 cleavage region 586" according to the present invention corresponds to amino acid 584 in the P42858 (HD_HUMAN) UniProtKB/Swiss-Prot database entry.

The present vaccines further target a second functionally defined region of Huntingtin, called the PRR domain (standing for Proline-Rich Region). This region has previously been shown to be implicated in intracellular protein interactions such as e.g. with PACSIN1 (Modregger et al., 2002) and evaluated as a potential intrabody targeting region using single chain Fv fragments that resisting the reducing conditions of the intracelullar milieu (Southwell et al., 2011).

In one embodiment of the invention, peptide vaccines of the invention induce a specific anti Huntingtin immune response, e.g. as shown in Example 1, in the recipient capable of mediating phagocytosis of (aggregated) Huntingtin or fragments thereof thereby providing a therapeutic effect, e.g. as shown in Example 3, FIG. 9 and Example 8, which has not been shown in the treatment of Huntington's disease in prior art by any antibody or vaccine-related approach. In another embodiment of the invention, antibodies of the invention can be used for passive immunization against Huntingtin protein in analogy to the active immunization approach based on the fact that monoclonal antibodies generated were derived from the same peptides and recognize the same targets, e.g. as shown in Example 1, 4 and 5.

Moreover, the present invention also discloses use of its antibodies for drug selection as well as in a method to diagnose and monitor the development of Huntington's disease.

The present invention relates to an immunogenic composition containing a Huntingtin-derived peptide wherein the peptide is provided in an immunogenic form, i.e. so as to elicit an immune response in a human individual to whom the composition is administered (in the form that antibodies directed to the peptide are produced in the human individual). Preferably the peptide is coupled to a carrier, preferably a protein carrier, or provided in a suspension, especially an oil-in-water suspension, so as to provide the peptide in an immunogenic form. The "vaccine" composition according to the present invention may therefore also be regarded as an "immunogenic composition", i.e. a composition that is eliciting an immune response in a human individual to whom the composition is applied. It is, however, known that the power to elicit immune response in a human individual may vary significantly within a population, for the purpose of the present invention it is therefore referred to an "immunogenic composition" if in at least 10%, preferably in at least 20%, more preferred in at least 30%, especially at least 50%, of the individuals of a given population, an immune reaction after delivery of the immunogenic compositions according to the present invention is detectable, e.g. antibodies specific for the peptides delivered are formed by the individual's immune system.

The present invention discloses immunogenic peptides of the HTT protein, comprising p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94); p7543b (TDNQYLGLQIC; SEQ ID No. 89), p7543c (TDNQYLGLQIGC; SEQ ID No. 90), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), and p8346 (CGPAVAEEPLHRP, SEQ ID No. 5), preferably for use in vaccination against symptoms caused by Huntington's disease or for delaying the onset of the disease. The "C" residue in these sequences is always used (and has been introduced) as a linker; this cysteine linker at the N- or C-terminus can (as any other linker, such as -GC, -GGC, -KC, -KCC, -KKC, -KKG, -KGC, -KCG, -KKCG, SEQ ID No: 100), -KKGC (SEQ ID No. 101)(and the N-terminal variants thereof, such as CG-, CGG-, etc.) or similar combinations of cysteine with amino acids such as e.g. beta-alanine or lysine as a spacer as e.g. used in peptides p6775 or p6768, p9394, p9395, p9396 or p9397 respectively, or as other chemical moieties that provide linker or spacer function or improved peptide solubility without impeding immunological properties) be present or not or provided alternatively at C- or N-terminus of the peptide (i.e. at the alternative end of the peptide chain). Such combinations of linker peptides with solubility improvers are provided e.g. in the lysine derivatives p9394-p9397. In other embodiments, a linker can also be provided in at other amino acid positions than the N- or C-terminus, e.g. at an amino acid with a functional group, such as serine, lysine, arginine, tyrosine, threonine, aspartic or glutamic acid, asparagine or glutamine, histidine, methionine, etc. (especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94) with significantly improved practical functional properties); however, in such embodiments, care must be taken that the immunological properties of the peptides are not severely impeded by such linking (for the possibility of defined size variations: see e.g. US 2010/0158933 A1).

The present invention discloses peptides derived from the PRR and the c6 region. The peptides according to the present invention have a significant beneficial technical relationship which is reflected by several common features: (1) All PRR- and C6-derived peptides according to the present invention share particular immunogenicity; their epitopes are particularly accessible (in contrast to e.g. peptides from the very N-terminus or the polyQ region as shown in example 1); in particular, targeting their epitopes is highly relevant for achieving a therapeutic effect in HTT targeting as shown in the functional in vivo examples in the example section below. (2) The peptides according to the present invention are mapping to regions of HTT for which structural/functional relevance such as protease accessibility or protein-protein interaction has been demonstrated. (3) Most importantly, the combinatorial targeting of these two epitopes provides efficient therapeutic effect (in contrast to using one single epitope.

In this connection, it has to be noted that not any HTT derived peptide can be used for the treatment of HTT. This is also shown in the example section below. In fact, certain peptides are more immunogenic than others. Moreover, the combination of certain peptides shows stronger effectivity (for example the combination of PRR- and C6-region peptides with respect to HTT plasma clearance ad motoric effects) most likely due to enhanced phagocytosis due to specific recognition of one or more Huntingtin epitopes. The present invention also provides advantageous combinations of peptides for the treatment of HTT. As already mentioned, with the present invention, therapeutic vaccines are provided which target (as the therapeutic principle) extracelullar HTT. This alone is already a completely novel strategy, since HTT has always been known as intracellullarly aggregating protein.

The peptides according to the present invention and the present vaccine targeting regions were defined (1) according to the accessibility and (2) immunogenicity of the regions/peptides. In addition, certain combinations of peptides (as shown in the in vivo examples below) provide enhanced HTT clearance and phenotypic (motoric and histologic) changes. These changes can be explained by anti-Huntingtin antibody and Fc receptor-mediated phagocytosis as shown in the examples. Fc-receptor mediated phagocytosis requires polyvalency of antigen-antibody complexes explaining the higher effectivity of targeting HTT on two or more rather than one single epitope: An antigen/antibody complex presenting multiple Fc portions is more likely to be cleared by phagocytosis than a single HTT molecule bound by one single antibody.

This was neither disclosed nor suggested by the prior art. For example, the therapeutic peptides pep4 and pep42 disclosed in WO 2012/140376 A1 or the peptides derived from the N-terminus of HTT reported by Miller et al. (2003) are derived from different regions of HTT than the peptides according to the present invention. Even more important, these peptides described e.g. in WO 2012/140376 A1 were never intended or used for any therapeutic purpose such as e.g. vaccines (i.e. for the induction of B-cell immune responses in a living organism). Instead, WO 2012/140376 A1 discloses peptides that can be used for aggregation inhibition (i.e. by direct interference with HTT or its fragments), which does not relate to inducing immune responses such as needed for a vaccine. The antibodies in WO 2010/015592 A2 were generated as probes for the detection of HTT (or its aggregates or fragments) by a FRET assay or other in vitro analytical means. The purpose for providing these antibodies was—again—experimental/analytical or diagnostic but not therapeutic. In general, it has never previously been proposed nor demonstrated that anti HTT antibodies could be used for therapeutic purposes for the treatment of Huntington's disease. Moreover, not any of the antibodies from WO 2010/015592 A2 has an overlap with the vaccination peptides according to the present invention. Finally, peptides "HP1" and "HP12" cited in Persichetti et al. (1995) were used for the generation of polyclonal antisera in order to provide analytical probes for HTT detection under experimental conditions (e.g. such as HTT detection by Western Blot or IHC) but not for the use in vaccine therapy. The same counts for monoclonal antibodies such as e.g. described in Ko et al. (2001) (e.g. MW1-8) that were generated by a polyQ-HTT-GST fusion protein but not by peptide immunization.

It is therefore important to note that the peptides according to the present invention are suitable for the generation of therapeutic vaccines, whereas the prior art peptides for generating polyclonal or monoclonal antibodies were designed to provide probes for analytical or diagnostic use.

Accordingly, the peptides according to the present invention derived from the PRR and the C6 region are specifically advantageous. Both groups are highly immunogenic, especially SEQ ID Nos. 1, 4, 16, 19 and 28; and 2, 3, 6-18 and 20-50; with SEQ ID Nos. 1-4 being highly preferred due to their functional performance in the in vivo experiments.

Further preferred immunogenic peptides are selected from the group consisting of p8855 (SDSSEIVLDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869 (CTDNQYLGLQIGQ, SEQ ID No. 12), p8868 (CGTDNQYLGLQIG, SEQ ID No. 13), p8870 (CDNQYLGLQIGQP, SEQ ID No. 14), p8871 (CNQYLGLQIGQPQ, SEQ ID No. 15), p6772 (CPQLPQP-PPQAQPLLP, SEQ ID No. 16), p8864 (TDNQYLGLQI-GQC, SEQ ID No. 17), p8865 (DNQYLGLQIGQPC, SEQ ID No. 18), p6775 (PPPQLPQPPPQAQPLLPQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYL-GLQIGQPQC, SEQ ID No. 23), and p8867 (QYLGLQI-GQPQDC, SEQ ID No. 24), wherein the N- or C-terminal cysteine residue (C) may be present or not or provided alternatively at the C- or N-terminus; preferably for use in vaccination against symptoms caused by Huntington's disease or for delaying the onset of the disease.

Other suitable immunogenic peptides are selected from the group consisting of p6763 (CaMATLEKLMKAF-ESLKSFQ, SEQ ID No. 25), p6764 (CaKLMKAF-ESLKSFQ, SEQ ID No. 26), p6765 (CEEQQRQQQQQQQ, SEQ ID No. 27), p6768 (QQQQQQPPPPPPPaKKKC, SEQ ID No. 28), p7541 (CSEIVLD, SEQ ID No. 29), p7552 (CSSEIVLD, SEQ ID No. 30), p7562 (CDSSEIVLD, SEQ ID No. 31), p7563 (CSDSSEIVLD, SEQ ID No. 32), p7567 (CEIVLD, SEQ ID No. 33), p7568 (CIVLD, SEQ ID No. 34), p7605 (CSEIVL, SEQ ID No. 35), p6776 (CSEIV-LDGTDNQYL, SEQ ID No. 36), p6777 (CSDSSEIV-LDGTDN, SEQ ID No. 37), p6776b (SEIVLDGTDN-QYLC, SEQ ID No. 38), p7752 (CSEIVLDGTDNQYL, SEQ ID No. 39), p7753 (CSEIVLDGTDNQYL, SEQ ID No. 40), p7754 (CSEAVLDGTDNQYL, SEQ ID No. 41), p7755 (CSEIVLDGTDNQYL, SEQ ID No. 42), p7756 (CSEIVLDGTDNQYL, SEQ ID No. 43), p7757 (CSEIV-LDGTDNQYL, SEQ ID No. 44), p7758 (CSEIVLDATD-NQYL, SEQ ID No. 45), p7745 (CSEIVLDGADNQYL, SEQ ID No. 46), p7746 (CSEIVLDGTANQYL, SEQ ID No. 47), p7747 (CSEIVLDGTDAQYL, SEQ ID No. 48), p7748 (CSEIVLDGTDNAYL, SEQ ID No. 49), p7749 (CSEIVLDGTDNQAL, SEQ ID No. 50), and p7750 (CSEIVLDGTDNQYA, SEQ ID No. 51), wherein the N- or C-terminal cysteine residue (C) may be present or not or provided alternatively at the C- or N-terminus.

According to the present invention, immunogenicity is the ability of a particular substance, such as an antigen or an epitope, to provoke an immune response, e.g. to elicit antibodies to the given peptide.

Preferably, these peptides are at least 7 amino acids long, and preferred lengths may be up to 16, preferably up to 14 or 20 amino acids residues (e.g. 7 or 8 to 20, 7 or 8 to 16 etc.). The "C" at the N- or the C-terminus of the peptides of SEQ ID NOs 1 to 51 has been provided as a linker which may or may not be present or replaced by another amino acid or chemical linker allowing for immobilization to a carrier. Further linking amino acids may be provided at this end of the peptide, either immediately before the "C" (cysteine residue) or immediately after the "C". The "C" may also be omitted, if it is not needed for coupling and/or if immunogenicity is safeguarded by other means than "C"-binding to a carrier. Alternatively, also fragments of these peptides may be used according to the present invention, preferably with a minimum length of 7 amino acid residues, wherein one or more amino acids before the cysteine residue are omitted. Alternatively, polar or charged amino acids not affecting immunogenicity and specificity of the immunogenic peptide can be used to increase peptide solubility. Thus, the peptide of the present invention comprises 7 to 30, preferably 7 to 20, more preferably 7 to 16, most preferably 8, amino acid residues. According to the invention, however, also longer peptides may very well be employed as anti-HTT-antibody-inducing antigens, e.g. as shown in Example 1.

In another embodiment, the present invention provides peptide-based vaccines for use in the treatment and/or prevention of Huntington's disease, comprising at least one immunogenic peptide of the HTT protein and optionally also one or more adjuvants. According to the present invention a vaccine is a biological preparation that improves immunity to a particular disease. According to the present invention, an adjuvant is a pharmacological agent that modifies the effect of other agents, e.g. to enhance the immune response to the supplied peptide epitope.

It is preferred according to the present invention that said at least one immunogenic peptide is coupled to a pharmaceutically acceptable carrier, which is preferably KLH. In general, any formulation that is able to promote a Th1 response thereby preferentially inducing IgG1 and IgG3 in humans is preferred according to the present invention. The immunogenic peptide may be provided in the vaccine in isolated (peptide) form or may be coupled or complexed (covalently or non-covalently) to other molecules, such as pharmaceutical carrier substances or polypeptides, lipid or carbohydrate structures, especially peptide linkers or protein carriers. Furthermore, the peptide linkers or protein carriers might consist of or contain T-cell helper epitopes, e.g. as shown in Example 2 and 3.

Preferably, the pharmaceutically acceptable carrier is KLH (Keyhole Limpet Hemocyanin), tetanus toxoid, albumin binding protein, bovine serum albumin, a dendrimer (MAP; Biol.Chem. 358:581) alone or combined with adjuvant substances described in Singh & O'Hagan, 1999 (specifically those in table 1 of this document) and O'Hagan & Valiante, 2003 (specifically the innate immune potentiating compounds and the delivery systems described therein, or mixtures thereof, such as low soluble aluminium compositions (e.g. aluminium hydroxide) MF59 aluminium phosphate, calcium phosphate, cytokines (e.g. IL-2, IL-12, GM-CSF), saponins (e.g. QS21), MDP derivatives, CpG oligos, IC31, LPS, MPL, squalene, D,L-alpha-tocopherol (e.g. mixed in an oil-in-water system with phosphate buffered saline), polyphosphazenes, emulsions (e.g. Freund's, SAF), liposomes, virosomes, iscoms, cochleates, PLG microparticles, poloxamer particles, virus-like particles, heat-labile enterotoxin (LT), cholera toxin (CT), mutant toxins (e.g. LTK63 and LTR72), microparticles and/or polymerized liposomes may be used). In a preferred embodiment of the invention the HTT peptide-vaccine composition contains aluminium hydroxide.

A vaccine comprising the present peptide and the pharmaceutically acceptable carrier may be administered by any suitable application mode, e.g. i.v., i.p., i.m., intranasal, oral, subcutaneous, etc. and in any suitable delivery device (O'Hagan & Valiente, 2003).

Typically, the vaccine contains the HTT-peptide according to the present invention in an amount of 0.1 ng to 10 mg, preferably 10 ng to 1 mg, especially 100 ng to 100 µg or, alternatively e.g. 100 fmole to 10 µmole, preferably 10 pmole to 1 µmole, especially 100 pmole to 100 nmole.

The vaccine may also comprise typical auxiliary substances, e.g. buffers, stabilizers, etc.

Prevention of Huntington's disease according to the present invention is defined as preventing or delaying the outbreak and/or onset of Huntington's disease associated symptoms such as motoric and psychiatric symptoms or immunologic and metabolic changes in individuals with a propensity to develop Huntington's disease symptoms based on their elevated number of CAG repeats in at least one HTT allele.

Treatment of Huntington's disease according to the present invention is defined as ameliorating Huntington's disease associated motoric symptoms such as chorea and psychiatric, or immunologic and metabolic changes in individuals, which were genetically identified to carry the mutated HTT (i.e. individuals who carry more than 26 CAG repeats in at least one HTT allele) and have been diagnosed positive for Huntington's disease based on their symptoms and genotype such as shown by inducing phenotypic changes in animal models for Huntington's disease, e.g. as in Example 2 and 3.

Active immunisation, i.e. vaccination, with the immunogenic HTT-derived peptides of the invention, leads to opsonisation of the HTT protein target and thereby induce specific phagocytosis thereof. Opsonisation is a process by which antibodies bind to an antigen such as Huntingtin and therefore mark it for an immune response. Phagocytic cells bind to the Fc portion of immunoglobulins and then internalise the marked antigen, e.g. as demonstrated for anti-Huntingtin antibodies PRR13 and C6-17 in Example 8.

Especially preferred according to the present invention are peptide-based vaccines containing at least one immunogenic peptide eliciting an immune response against HTT or a naturally occurring fragment thereof, especially a fragment of relevance for Huntington's disease, for use in the prevention and/or treatment of Huntington's disease, wherein said at least one immunogenic peptides of the HTT proteins are selected from the group consisting of p6773 (LPQPP-PQAQPLLPQPQPC, SEQ ID No. 1), p7564 (CPSDS-SEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94); p7543b (TDNQYLGLQIC; SEQ ID No. 89), p7543c (TDNQYL-GLQIGC; SEQ ID No. 90), p6771 (LPQPPPQAQPLLPC, SEQ ID No. 4), p8346 (CGPAVAEEPLHRP, SEQ ID No. 5), p8855 (SDSSEIVLDGTDC, SEQ ID No. 6), p8858 (EIV-LDGTDNQYLC, SEQ ID No. 7), p8859 (IVLDGTDN-QYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869 (CTDNQYLGLQIGQ, SEQ ID No. 12), p8868 (CGTDN-QYLGLQIG, SEQ ID No. 13), p8870 (CDNQYLGLQI-GQP, SEQ ID No. 14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PP-PQLPQPPPQAQPLLPQPQPaC, SEQ ID No. 19), p8854 (PSDSSEIVLDGTC, SEQ ID No. 20), p8856 (DSSEIV-LDGTDNC, SEQ ID No. 21), p8857 (SEIVLDGTDNQYC, SEQ ID No. 22), p8866 (NQYLGLQIGQPQC, SEQ ID No. 23), p8867 (QYLGLQIGQPQDC, SEQ ID No. 24), p6763 (CaMATLEKLMKAFESLKSFQ, SEQ ID No. 25), p6764 (CaKLMKAFESLKSFQ, SEQ ID No. 26), p6765 (CE-EQQRQQQQQQQ, SEQ ID No. 27), p6768 (QQQQQQP-PPPPPPaKKKC, SEQ ID No. 28), p7541 (CSEIVLD, SEQ ID No. 29), p7552 (CSSEIVLD, SEQ ID No. 30), p7562 (CDSSEIVLD, SEQ ID No. 31), p7563 (CSDS-SEIVLD, SEQ ID No. 32), p7567 (CEIVLD, SEQ ID No. 33), p7568 (CIVLD, SEQ ID No. 34), p7605 (CSEIVL, SEQ ID No. 35), p6776 (CSEIVLDGTDNQYL, SEQ ID No. 36), p6777 (CSDSSEIVLDGTDN, SEQ ID No. 37), p6776b (SEIVLDGTDNQYLC, SEQ ID No. 38), p7752 (CAEIV-LDGTDNQYL, SEQ ID No. 39), p7753 (CSAIVLDGTD-NQYL, SEQ ID No. 40), p7754 (CSEAVLDGTDNQYL, SEQ ID No. 41), p7755 (CSEIALDGTDNQYL, SEQ ID No. 42), p7756 (CSEIVADGTDNQYL, SEQ ID No. 43), p7757 (CSEIVLAGTDNQYL, SEQ ID No. 44), p7758 (CSEIVLDATDNQYL, SEQ ID No. 45), p7745 (CSEIV-LDGADNQYL, SEQ ID No. 46), p7746 (CSEIVLDGTAN-QYL, SEQ ID No. 47), p7747 (CSEIVLDGTDAQYL, SEQ ID No. 48), p7748 (CSEIVLDGTDNAYL, SEQ ID No. 49), p7749 (CSEIVLDGTDNQAL, SEQ ID No. 50), and p7750 (CSEIVLDGTDNQYA, SEQ ID No. 51), preferably p6773 (LPQPPPQAQPLLPQPQPC, SEQ ID No. 1), p7564 (CPSDSSEIVLD, SEQ ID No. 2), p7543 (GTDNQYL-GLQIGC, SEQ ID No. 3), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), p8346 (CGPAVAEEPLHRP, SEQ ID No. 5), p8855 (SDSSEIV-LDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDN-QYLGLQIGC, SEQ ID No. 11), p8869 (CTDNQYL-GLQIGQ, SEQ ID No. 12), p8868 (CGTDNQYLGLQIG, SEQ ID No. 13), p8870 (CDNQYLGLQIGQP, SEQ ID No.

14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PPPQLPQPPPQAQPLLPQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), and p8867 (QYLGLQIGQPQDC, SEQ ID No. 24), especially p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94); p7543b (TDNQYLGLQIC; SEQ ID No. 89), p7543c (TDNQYLGLQIGC; SEQ ID No. 90), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), and p8346 (CGPAVAEEPLHRP, SEQ ID No. 5), or peptides comprising at least one of these peptides, preferably in a total length of maximally 50 amino acid residues, more preferred of maximally 30 amino acid residues, further preferred of maximally 20 amino acid residues, especially of maximally 16 amino acid residues. Specifically preferred peptides according to the present invention may have a length from 6 to 10 amino acid residues, for example 7, 8 or 9 amino acids, especially 9 amino acids.

The present invention also refers to fragments of the immunogenic peptides of SEQ ID Nos. 1 to 51 which contain a core epitope. The core epitope of peptides p6771, p6773 and p7543 have been identified in the example section of the present invention. The core epitope of peptide p6771 or p6773 are PPQAQPL (SEQ ID No. 78), PPQAQP (SEQ ID No. 79), QPLL (SEQ ID No. 80) and PQAQPLL (SEQ ID No. 81) and especially LLPQP (SEQ ID No. 77), respectively. The core epitope of peptide p7543 are QYLGLQIG (SEQ ID No. 82), YLGLQIG (SEQ ID No. 83), DNQYLGLQIG (SEQ ID No. 84), DNQYLGL (SEQ ID No. 85) and YLGLQIG (SEQ ID No. 86), especially QYLGLQIG. Accordingly, preferred immunogenic peptides according to the present invention comprise at least one of these core epitopes, and preferably have a maximum length of 30, preferably 20, especially 16 amino acid residues, wherein said peptides are preferably used for the generation or identification of specific Huntingtin C6-cleavage inhibitors and wherein said specific Huntingtin C6-cleavage inhibitors are preferably defined as monoclonal antibodies, polyclonal antisera, monoclonal antibody-derived fragments such as Fv's, scFv's, F(ab), F(ab)2.

According to a preferred aspect, the present invention provides an immunogenic composition which may be used as an active vaccine and which comprises at least two of the immunogenic peptides disclosed with the present invention. Preferably, the composition contains at least three of these peptides, more preferred at least four of these peptides, especially at least five of these peptides. Preferably at least one of such two or more peptides is selected from the group consisting of p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94); p7543b (TDNQYLGLQIC; SEQ ID No. 89), p7543c (TDNQYLGLQIGC; SEQ ID No. 90), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), and p8346 (CGPAVAEEPLHRP, SEQ ID No. 5). It is also preferred to combine at least one peptide from the "C6" region with at least one peptide from the "PRR" region (as e.g. disclosed in table 2). A specifically preferred combination is the combination of p7543 (GTDNQYLGLQIGC, SEQ ID No. 3) with any of the other peptides, specifically with SEQ ID NOs 1, 2, 4 and 5. Especially preferred is the combination of p7543 (GTDNQYLGLQIGC, SEQ ID No. 3) (or p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94); p7543b (TDNQYLGLQIC; SEQ ID No. 89), p7543c (TDNQYLGLQIGC; SEQ ID No. 90)) with p6771 (LPQPPPQAQPLLPC, SEQ ID No. 4) and p7543 (GTDNQYLGLQIGC, SEQ ID No. 3) with p7564 (CPSDSSEIVLD, SEQ ID No. 2).

In another aspect, the present invention provides a pharmacological composition comprising a polyclonal antibody serum specifically recognising at least one peptide of the HTT protein for use as a vaccine in the treatment and/or prevention of Huntington's disease.

For the present invention the terms "pharmaceutical preparation" and "pharmacological composition" are used interchangeably and refers to a composition that is intended and suitable for delivery to human individuals. Such preparations or compositions have been manufactured according to GMP (good manufacturing practices) and are sufficiently sterile and packaged to comply with the prerequisites necessitated by the EMA and FDA, especially by the EMA.

According to the present invention the antibodies of the polyclonal antibody serum may be purified according to techniques known to a person skilled in the art, such as affinity chromatography.

The pharmacological composition may additionally contain a pharmaceutically acceptable carrier or excipient to which the polyclonal antibodies can be coupled or complexed (covalently or non-covalently). The pharmaceutical composition comprising the polyclonal antibodies may additionally contain at least one additional therapeutic agent.

According to the present invention, it is preferred that the antibodies of the polyclonal antibody serum lead to Immunoglobulin-mediated effector functions such as e.g. opsonisation and phagocytosis of HTT protein, aggregated HTT or fragments thereof as shown in Example 8. This requires immunoglobulin carrying appropriate pro-opsonophagocytic activity in its Fc portion encoded by particular sugar residues as allowing for opsonization, phagocytosis, complement lysis or NK cell killing effector functions combined with the blocking/sequestering function for wild type and mutant Huntingtin in soluble, aggregated or fragmented form. An example is provided showing phagocytic activity provided by p6773 or p7543 vaccine-derived monoclonal antibodies (Example 8).

In another preferred embodiment of the invention, the polyclonal antibody serum comprised in said pharmacological composition is raised against at least one peptide selected from the group consisting of p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94); p7543b (TDNQYLGLQIC; SEQ ID No. 89), p7543c (TDNQYLGLQIGC; SEQ ID No. 90), p6771 (LPQPPPQAQPLLPC, SEQ ID No. 4), p8346 (CGPAVAEEPLHRP, SEQ ID No. 5), p8855 (SDSSEIVLDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869 (CTDNQYLGLQIGQ, SEQ ID No. 12), p8868 (CGTDNQYLGLQIG, SEQ ID No. 13), p8870 (CDNQYLGLQIGQP, SEQ ID No. 14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PPPQLPQPPPQAQPLLPQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), p8867 (QYLGLQIGQPQDC, SEQ ID No. 24), p6763 (CaMATLEKLMKAFESLKSFQ, SEQ ID No. 25), p6764 (CaKLMKAFESLKSFQ, SEQ ID No. 26), p6765 (CEQQRQQQQQQQ, SEQ ID No. 27), p6768 (QQQQQQPPPPPPPPaKKKC, SEQ ID No. 28), p7541 (CSEIVLD, SEQ ID No. 29), p7552 (CSSEIVLD, SEQ ID No. 30), p7562 (CDSSEIVLD, SEQ ID No. 31), p7563 (CSDSSEIVLD, SEQ ID No. 32), p7567 (CEIVLD, SEQ ID No. 33), p7568 (CIVLD, SEQ ID No. 34), p7605 (CSEIVL, SEQ ID No. 35), p6776 (CSEIVLDGTDNQYL, SEQ ID No. 36), p6777 (CSDSSEIVLDGTDN, SEQ ID No. 37), p6776b (SEIVLDGTDNQYLC, SEQ ID No. 38), p7752 (CAEIVLDGTDNQYL, SEQ ID No. 39), p7753 (CSAIVLDGTDNQYL, SEQ ID No. 40), p7754 (CSEAVLDGTDNQYL, SEQ ID No. 41), p7755 (CSEIALDGTDNQYL, SEQ ID No. 42), p7756 (CSEIVADGTDNQYL, SEQ ID No. 43), p7757 (CSEIVLAGTDNQYL, SEQ ID No. 44), p7758 (CSEIVLDATDNQYL, SEQ ID No. 45), p7745 (CSEIVLDGADNQYL, SEQ ID No. 46), p7746 (CSEIVLDGTANQYL, SEQ ID No. 47), p7747 (CSEIVLDGTDAQYL, SEQ ID No. 48), p7748 (CSEIVLDGTDNAYL, SEQ ID No. 49), p7749 (CSEIVLDGTDNQAL, SEQ ID No. 50), and p7750 (CSEIVLDGTDNQYA, SEQ ID No. 51), preferably p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), p8346 (CGPAVAEEPLHRP, SEQ ID No. 5), p8855 (SDSSEIVLDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869 (CTDNQYLGLQIGQ, SEQ ID No. 12), p8868 (CGTDNQYLGLQIG, SEQ ID No. 13), p8870 (CDNQYLGLQIGQP, SEQ ID No. 14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PPPQLPQPPPQAQPLLPQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), and p8867 (QYLGLQIGQPQDC, SEQ ID No. 24), especially p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), and p8346 (CGPAVAEEPLHRP, SEQ ID No. 5).

In another preferred embodiment of the invention, the polyclonal antibody serum comprised in said pharmacological composition that are raised against at least one peptide of p6773 (SEQ ID No. 1) and p6771 (SEQ ID No. 4) covers the core epitope region as exemplified by fine epitope analysis of immunsera, e.g. as shown in Example 4. Based on single amino acid substitution analysis, the core epitope covers amino acid positions that cannot be exchanged by alanine or most other amino acids without losing binding by the antibody tested, e.g. as explained in Example 4.

Alternatively or in combination, the polyclonal antibody serum comprised in said pharmacological composition is raised against peptide p7543 (SEQ ID No. 3) covering the core epitope regions provided in Example 4 as shown by fine epitope analysis of sera generated by peptide p7543. Based on amino acid substitution analysis, peptide positions cannot be exchanged without modifying the epitope recognition (at least within the core epitope regions) by the corresponding antibodies, e.g. as explained in Example 4.

Alternatively or in combination, the polyclonal antibody serum comprised in said pharmacological composition is raised against peptide p7564 (SEQ ID No. 2) covering the core epitope region of p7564 derived mAB M1D1, e.g. as provided in Example 5 FIG. 17.

Alternatively or in combination, the polyclonal antibody serum comprised in said pharmacological composition is raised against peptide p6776 (SEQ ID No. 36) covering the core epitope region, e.g. as provided in Example 4 FIG. 11.

According to another aspect, the present invention relates to monoclonal antibodies against HTT or naturally occurring fragments thereof, preferably for use in the treatment of Huntington's disease or for delaying the onset of the symptoms of this disease. The monoclonal (as well as the polyclonal) antibodies according to the present invention are provided as "isolated antibodies". An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For a monoclonal antibody, also the nucleic acid encoding the antibody is available; the present invention therefore also encompasses the isolated nucleic acids encoding such antibodies. An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. "Isolated nucleic acid encoding an anti-HTT antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-, yeast- or mammalian cell-display methods, and methods utilizing transgenic animals containing all or part of the human immunoglobulin loci, such methods and other exemplary methods for making monoclonal antibodies being described herein.

In another aspect, the present invention also provides a monoclonal antibody "PRR13" having a binding domain capable of binding to an epitope of the HTT protein having the sequence "LLPQP" contained within peptide p6773 (SEQ ID No. 1), especially to the core epitope LLPQP (SEQ ID No. 77). With the present invention, mABs against this minimal core epitope that has been provided with the experiments according to the present invention are provided, i.e. against the core epitope LLPQP (SEQ ID No. 77). In a preferred embodiment, said monoclonal antibody is characterised as being a monoclonal antibody (e.g. preferably PRR13), which comprises a heavy chain variable region CDR1 comprising the peptide sequence GYSFTDFY (SEQ ID No. 54), a heavy chain variable region CDR2 comprising IDPKNGDT (SEQ ID No. 55), a heavy chain variable region CDR3 comprising ATYYGYTMDY (SEQ ID No. 56), a light chain variable region CDR1 comprising SSVTSSY (SEQ ID No. 57), a light chain variable region CDR2 comprising STS (SEQ ID No. 58) and a light chain variable region comprising HQYRRPPRT (SEQ ID No. 59), e.g. as shown in Example 5.

CDR are complementarity determining regions and represent variable regions of antibodies, with which the antibody binds to its specific epitope. The type and number of heavy chain determines the class of antibody, i.e. IgA, IgD, IgE, IgG and IgM antibodies, respectively. Antibodies contain also two identical light chains, which can be of lambda or kappa type.

According to the present invention monoclonal antibodies are preferably engineered antibodies where CDRs of non-human antibodies were transferred into a human antibody framework and thereby adapted in sequence such that affinity and specificity of the original hybridoma-derived mouse antibody is at least maintained and T-cell and B-cell immunogenicity to humans is minimized (humanized monoclonal antibodies), bispecific or chimeric monoclonal antibodies, antibodies with enhanced effector or stabilization functions involving Fc receptors or antibodies carrying a cargo for effector functions or diagnostic marker functions. The antibodies according to the present invention are preferably human anti HTT antibodies.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al, Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al, supra. In one embodiment, for the VH, the subgroup is subgroup III as in Kabat et al, supra.

A "humanized" antibody refers to a chimeric antibody comprising amino acid residues from non-human HVRs and amino acid residues from human FRs. "Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized variant" of an antibody, e.g., a non-human antibody, refers to an antibody that has undergone humanization. In one preferred embodiment, a murine HVR is grafted into the framework region of a human antibody to prepare the "humanized antibody". The murine variable region amino acid sequence is aligned to a collection of human germline antibody V-genes, and sorted according to sequence identity and homology. The acceptor sequence is selected based on high overall sequence homology and optionally also the presence of the right canonical residues already in the acceptor sequence. The germline V-gene encodes only the region up to the beginning of HVR3 for the heavy chain, and till the middle of HVR3 of the light chain. Therefore, the genes of the germline V-genes are not aligned over the whole V-domain. The humanized construct comprises the human frameworks 1 to 3, the murine HVRs, and the human framework 4 sequence derived from the human JK4, and the JH4 sequences for light and heavy chain, respectively. Before selecting one particular acceptor sequence, the so-called canonical loop structures of the donor antibody can be determined. These canonical loop structures are determined by the type of residues present at the so-called canonical positions. These positions lie (partially) outside of the HVR regions, and should be kept functionally equivalent in the final construct in order to retain the HVR conformation of the parental (donor) antibody. In WO 2004/006955 A1 a method for humanizing antibodies is reported that comprises the steps of identifying the canonical HVR structure types of the HVRs in a non-human mature antibody; obtaining a library of peptide sequence for human antibody variable regions; determining the canonical HVR structure types of the variable regions in the library; and selecting the human sequences in which the canonical HVR structure is the same as the non-human antibody canonical HVR structure type at corresponding locations within the non-human and human variable regions. Summarizing, the potential acceptor sequence is selected based on high overall homology and optionally in addition the presence of the right canonical residues already in the acceptor sequence. In some cases simple HVR grafting only result in partial retention of the binding specificity of the non-human antibody. It has been found that at least some specific non-human framework residues are required for reconstituting the binding specificity and have also to be grafted into the human framework, i.e. so called "back mutations" have to be made in addition to the introduction of the non-human HVRs (see e.g. Queen et al., PNAS 86 (1989), 10029-10033). These specific framework amino acid residues participate in FR-HVR interactions and stabilized the conformation (loop) of the HVRs. In some cases also forward-mutations are introduced in order to adopt more closely the human germline sequence. Thus "humanized variant of an antibody according to the invention" (which is e.g. of mouse origin) refers to an antibody, which is based on the mouse antibody sequences in which the VH and VL are humanized by above described standard techniques (including HVR grafting and optionally subsequent mutagenesis of certain amino acids in the framework region and the HVR-H1, HVR-H2, HVR-L1 or HVR-L2, whereas HVR-H3 and HVR-L3 remain unmodified).

In general, techniques for developing antibodies suitable for use in treatment of human patients from murine or other primarily selected mABs are well established (reviewed in Safdari et al 2013). The antibodies disclosed herein may therefore be subjected to such development processes for providing improved antibodies by applying such validated techniques, especially CDR-grafting based methods (such as e.g. reviewed by Kim & Hong Methods Mol Biol. 2012; 907:237-45 or Whitelegg, N. & Rees, A R Antibody variable Regions: Towards a Unified modeling method. In: Methods in Molecular Biology, Biotechnology and Medicine, (Ed. Lo, B), 2004; 248:51-91.), germline humanization or "super-humanization" (such as reviewed by Pelat, T. Et al., Mini Rev Med Chem. 2009 December; 9(14):1633-8.) and resurfacing (such as described by Mader and Kunert et al., Prot.Eng.Des.Selec. 2010, 23, 947-954).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs are disclosed herein.

According to the present invention, also anti HTT antibodies that comprises a heavy chain variable domain (VH) sequence and/or light chain variable domain (VL) sequence having at least 90%, 91%, 92%, 93%, 94%, 95%, 96%, 97%), 98%), 99%), or 100% sequence identity to the amino acid sequence of SEQ ID NOs: 60 to 65 are provided. In certain embodiments, a VH sequence having at least 90%>, 91%>, 92%, 93%, 94%, 95%, 96%, 97%, 98%, or 99% identity contains substitutions (e.g. conservative substitutions), insertions, or deletions relative to the reference sequence, but an anti HTT antibody comprising that sequence retains the ability to bind to HTT, especially the epitope given. In certain embodiments, a total of 1 to 10 amino acids have been substituted, inserted and/or deleted in SEQ ID NO s: 60 to 65. In certain embodiments, substitutions, insertions, or deletions occur in regions outside the HVRs (i.e. in the FRs).

Preferred variants of the anti HTT antibodies according to the present invention are i.a. disclosed in FIG. 27 (i.e. variants hPRR13-2 to -16 and hC6-17-2 to -16). Accordingly, anti HTT antibodies with the amino acid exchanges in the H/L framework are specifically preferred according to the present invention. Moreover, all combinations of these variants are also specifically preferred. For example, for the heavy chain of the PRR antibody there are 1 wt+3 mutations, for the light chain there are also 1 wt+3 mutations. This provides a possible combination space of 4×4 variants as listed in the table of FIG. 27. For the mAB huC6-17, the following combinations are preferred: light chain: 1 wt+1 mut; heavy: 1 wt+7 mutations, making a total of 16 variants.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software or the "needle" pairwise sequence alignment application of the EMBOSS software package. Those skilled in the art can determine appropriate parameters for aligning sequences, including any algorithms needed to achieve maximal alignment over the full length of the sequences being compared. For purposes herein, however, % amino acid sequence identity values are calculated using the sequence alignment of the computer programme "needle" of the EMBOSS software package (publicly available from European Molecular Biology Laboratory; Rice et al., EMBOSS: the European Molecular Biology Open Software Suite, Trends Genet. 2000 June; 16(6):276-7, PMID: 10827456).

The needle programme can be accessed under the web site http://www.ebi.ac.uk/Tools/psa/emboss needle/ or downloaded for local installation as part of the EMBOSS package from http://emboss.sourceforge.net/. It runs on many widely-used UNIX operating systems, such as Linux.

To align two protein sequences, the needle programme is preferably run with the following parameters: Command-line: needle-auto-stdout-asequence SEQUENCE_FILE_A-bsequence SEQUENCE_FILE_B-datafile EBLOSUM62-gapopen 10.0-gapextend 0.5-endopen 10.0-endextend 0.5-aformat3 pair-sprotein1-sprotein2 (Align_format: pair Report_file: stdout).

The % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program needle in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, an antibody provided herein is a chimeric antibody. Certain chimeric antibodies are described, e.g., in U.S. Pat. No. 4,816,567 A; and Morrison et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity. Humanized antibodies and methods of making them are reviewed, e.g., in WO 2004/006955 A1 (approach via canonical structures).

In certain embodiments, an antibody provided herein is a human antibody. Human antibodies can be produced using various techniques known in the art. Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23 (2005) 1117-1125, U.S. Pat. Nos. 6,075,181 and 6,150,584 describing XENOMOUSE™ technology; U.S. Pat. No. 5,770,429 A describing HuMab® technology; U.S. Pat. No. 7,041,870 A describing K-M MOUSE® technology, and US 2007/0061900 A1, describing Veloci-Mouse® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. Human antibodies generated via human B-cell hybridoma technology are also described in Li et al, PNAS 103 (2006) 3557-3562. Additional methods include those described, for example, in U.S. Pat. No. 7,189,826 (describing production of monoclonal human IgM antibodies from hybridoma cell lines) or made by the Trioma technology. Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies according to the present invention may also be isolated by screening combinatorial libraries for antibodies with the desired activity or activities. For example, a variety of methods are known in the art for generating phage display libraries and screening such libraries for antibodies possessing the desired binding characteristics. Such methods are further described, e.g., in Fellouse, PNAS (2004) 12467-12472.

In certain phage display methods, repertoires of VH and VL genes are separately cloned by polymerase chain reaction (PCR) and recombined randomly in phage libraries, which can then be screened for antigen-binding phage. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization. Finally, naive libraries can also be made synthetically by cloning non-rearranged V-gene segments from stem cells, and using PCR primers containing random sequence to encode the highly variable CDR3 regions and to accomplish rearrangement in vitro. Further publications describing human antibody phage libraries include, for example: U.S. Pat. No. 5,750,373 A, US 2005/0079574 A1, US 2005/0119455 A1, US 2005/0266000 A1, US 2007/0117126 A1, US 2007/0160598 A1, US 2007/0237764 A1, US 2007/0292936 A1, and US 2009/0002360 A1. Antibodies or antibody fragments isolated from human antibody libraries are considered human antibodies or human antibody fragments herein.

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for HTT and the other is for any other antigen. Bispecific antibodies may also be used to localize cytotoxic agents to cells which express HTT. Bispecific antibodies can be prepared as full length antibodies or antibody fragments. Techniques for making multispecific antibodies include, but are not limited to, recombinant coexpression of two immunoglobulin heavy chain-light chain pairs having different specificities (WO 93/08829 A, U.S. Pat. No. 5,731,168 A). Multi-specific antibodies may also be made by engineering electrostatic steering effects for making antibody Fc-heterodimeric molecules (WO 2009/089004 A); cross-linking two or more antibodies or fragments (e.g. U.S. Pat. No. 4,676,980 A); using leucine zippers to produce bi-specific antibodies; using "diabody" technology for making bispecific antibody fragments (e.g., Holliger et al, PNAS (1993) 6444-6448); and using single-chain Fv (sFv) dimers; and preparing trispecific antibodies. Engineered antibodies with three or more functional antigen binding sites, including "Octopus antibodies" are also included herein (e.g. US 2006/0025576 A1). The antibody or fragment herein also includes a "Dual Acting Fab" or "DAF" comprising an antigen binding site that binds to HTT as well as another, different antigen (see US 2008/0069820 A1, for example). The antibody or fragment herein also includes multispecific antibodies described in WO 2009/080251 A, WO 2009/080252 A, WO 2009/080253 A, WO 2009/080254 A, WO 2010/112193 A, WO 2010/115589 A, WO 2010/136172 A, WO 2010/145792 A, and WO 2010/145793 A.

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the HVRs and FRs. Conservative substitutions are shown in the following table under the heading of "preferred substitutions". More substantial changes are provided below in reference to amino acid side chain classes. Amino acid substitutions may be introduced into an antibody of interest and the products screened for a desired activity, e.g., retained/improved antigen binding, decreased immunogenicity, or improved ADCC or CDC.

| Original Residue | Exemplary Substitution | Preferred Substitution |
|---|---|---|
| Ala (A) | Val, Leu, Ile, | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process, and/or SDRs (a-CDRs), with the resulting variant VH or VL being tested for binding affinity. Affinity maturation is effected by constructing and reselecting from secondary libraries. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modelling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g. conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions. A useful method for identification of residues or regions of an antibody that may be targeted for mutagenesis is called "alanine scanning mutagenesis". In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighbouring residues may be targeted or eliminated as candidates for substitution. Variants may be screened to determine whether they contain the desired properties. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the Nor C-terminus of the antibody to an enzyme (e.g. for ADEPT) or a polypeptide which increases the serum half-life of the antibody.

The PRR (proline-rich-region) site of Huntingtin is located close to the poly-Q sequence of the protein. It is known from the literature that the PRR region is functionally relevant to the Huntingtin protein (Modregger et al 2002). An intrabody derived from a recombinant scFv library targeting the PRR region of Huntingtin inside the cell was shown to be beneficial in an animal model for Huntington's disease (Southwell et al., 2011) by selectively increasing the intracellular turnover of the mutant form of HTT protein. Monoclonal antibodies recognizing the polyproline stretches flanking the PRR region, have previously been published as probes (mAB MW7 by Ko et al. 2001) however no therapeutic use in Huntington's disease had been considered or could be demonstrated because of the low complexity of its epitope consisting of a polyproline stretch not unique for Huntingtin within the human proteome. More generally, active or passive targeting of Huntingtin by antibodies or vaccines has not previously been considered because Huntingtin had always been regarded as intracellular target suited only for intracellular targeting. In contrast to monoclonal antibody MW7, that binds epitopes with more than 5 consecutive prolines (Ko et al., 2001), mAB PRR13 from the present invention has a complex epitope and specifically and selectively binds to its core epitope contained on p6773, e.g. as demonstrated in Example 5.

According to the present invention it is especially preferred to use monoclonal antibodies in a pharmaceutical composition used in the prevention and/or treatment of Huntington's disease. According to the present invention, a pharmaceutical composition comprising monoclonal antibodies may additionally contain pharmaceutically acceptable carriers or excipients. Moreover, a pharmaceutical composition comprising the monoclonal antibodies of the present invention may additionally contain a therapeutic agent or may be physically associated with a therapeutic agent. Such a pharmaceutical composition may also be formulated with an adjuvant, preferably aluminium hydroxide.

In another embodiment, the present invention provides a monoclonal antibody having a binding domain capable of binding to a peptide of the HTT protein having the sequence of p7543 (SEQ ID No. 3) or preferably the core epitope of C6-17, e.g. as determined in Example 4. In a preferred embodiment said monoclonal antibody is characterised as being a monoclonal antibody (e.g. preferably C6-17), which comprises a heavy chain variable region CDR1 comprising GYTFTEYT (SEQ ID No. 66), a heavy chain variable region CDR2 comprising INPNNGGT (SEQ ID No. 67), a heavy chain variable region CDR3 comprising ASLDGRDY (SEQ ID No. 68), a light chain variable region CDR1 comprising QSLLNSRTRKNY (SEQ ID No. 69), a light chain variable region CDR2 comprising WAS (SEQ ID No. 7β) and a light chain variable region comprising KQSYN-LLT (SEQ ID No. 71), e.g. as shown in Example 5.

According to the present invention, caspase region 586 is referred to a region on the HTT protein surrounding a previously defined caspase cleavage site at Position 586 of the Huntingtin protein that is susceptible to protease cleavage by caspase 6 and other proteases such as caspase 2, 8, or 10 (Wong et al. 2014). The etiological role of protease cleavage within this region was previously established by Graham et al. 2006 and prevention or reduction of the resulting Huntingtin fragment has been recognized as beneficial. In the present invention, it is demonstrated that particular peptides derived from this region can effectively induce antibodies with unexpectedly stronger accessibility to Huntingtin than neighbour peptides from the same region, e.g. as shown in Example 1 and 7. Antibodies generated by these peptides are capable of masking yet unidentified epitopes thereby preventing protease cleavage. Thus caspase region 586-derived, cleavage inhibiting antibodies according to Example 7 can also be defined as site-specific protease cleavage inhibitors.

In yet another embodiment, the present invention provides a monoclonal antibody having a binding domain capable of binding to a peptide of the HTT protein having a sequence of p7564 (SEQ ID No. 2) or preferably the epitope of M1D1, e.g. according to Example 5, FIG. 17; preferably for use for the treatment of Huntington' disease. In a preferred embodiment said monoclonal antibody is characterised as being a monoclonal antibody (e.g. preferably M1D1), which comprises a heavy chain variable region CDR1 comprising GFTFNTYA (SEQ ID No. 72), a heavy chain variable region CDR2 comprising IRSKSNNYAT (SEQ ID No. 73), a heavy chain variable region CDR3 comprising VRHGEYGNPWFAY (SEQ ID No. 74), a light chain variable region CDR1 comprising QSLVHSNGNTY (SEQ ID No. 75), a light chain variable region CDR2 comprising KVS (SEQ ID No. 76) and a light chain variable region comprising SQSTHVPYT (SEQ ID No. 77), e.g. as described in Example 5.

In contrast to prior art monoclonal and polyclonal antibodies derived from a peptide $^{583}$IVLD$^{586}$ occurring at high frequency within the human proteome (Warby et al., 2008), antibody M1D1 recognizes a core epitope consisting of the Huntingtin-derived sequence SSEIVLD containing a free C-terminal aspartic acid that is unique within the human RefSeq protein database thereby providing high specificity towards caspase cleaved Huntingtin protein, e.g. as shown in Example 4 FIG. 12 and Example 5 FIG. 17. In contrast to the antibody of Warby et al, the antibody according to the present invention is more specific. It also has a different core epitope than "IVLD" (see Example 1, FIG. 3). This higher specificity is also due to the fact that "IVLD" (according to Warby) occurs more than several 100 times within the human proteome, whereas the M1D1 epitope occurs only once according to BLAST-RefSeq analysis. M1D1 as provided with the present invention is a distinct clone with unique CDR's—isotype IgM.

According to a preferred embodiment, the antibody according to the present invention comprises the following VH and VL amino acid sequences:

>C6-17 VH Consensus Amino Acid Sequence:

(SEQ ID No. 60)

MGWSCIMLFLLSGTAGVLSEVQLQQSGPELVKPGASVKISCKTSGYTFTE

YTMHWVKQSH-

GKSLEWIGGINPNNGGTRYNQKFKGKATLTVDRSSSTAYMELRSLTSEDS

AVYYCASLD-

GRDYWGQGTTLTVSSAKTTAPSVFPLA

>C6-17 VL Consensus Amino Acid Sequence:

(SEQ ID No. 61)

MVLMLLLLWVSGTCGDIVMSQSPSSLAVSAGEKVTMSCKSSQSLLNSRTR

KNYL-

AWYQQKPGQSPKLLIYWASTRESGVPDRFTGSGSGTDFTLTISSVQAED-

LAVYSCKQSYNLLTFGAGTKLELKRADAAPTVSIFPPSSEQLTSGGASVV

CFLNNFYPK

According to a preferred embodiment, the antibody according to the present invention comprises the following VH and VL amino acid sequences:

>PRR13 VH Consensus Amino Acid Sequence:
(SEQ ID No. 62)
MGWSWVMLFLLSGTGGVLSEVQLQQSAPELVKPGASVKMSCKASGYSFTD

FYMKWVKQSH-

GKGLEWIGDIDPKNGDTFYNQKFKGRATLTVDKSSSTAYMQLNSLTTEDS

AVYY-

CATYYGYTMDYWGQGTSVTVSSAKTTAPSVYPLAPVCGDTTGSSVTLGCL

VKGYF

>PRR13 VL Consensus Amino AcidSequence:
(SEQ ID No. 63)
MDFQVQIFSFLLISASVIMSRGQIVLTQSPAIMSASLGERVTMTCTASSS

V-

TSSYLHWYQQKPGSSPKLWIYSTSNLASGVPARFSGSGSGTSYSLTISS-

MEAEDAATYYCHQYRRPPRTFGGGTKLEIKRADAAPTVSIFPPSSEQLTS

G-

GASVVCFLNNFYPR

According to a preferred embodiment, the antibody according to the present invention comprises the following VH and VL amino acid sequences:

>M1D1 VH Consensus Amino Acid Sequence:
(SEQ ID No. 64)
MDFGLSWVFFVVFYQGVHCEVQLVESGGGLVQPKGSLKLSCAASGFTFNT

YAMNWVR-

QAPGKGLEWVARIRSKSNNYATYYADSVKDRFTISRDDSQSMLYLQMNNL

KTEDTAMYYCVRH-

GEYGNPWFAYWGQGTLVTVSAESQSFPNVFPL

>M1D1 VL Consensus Amino Acid Sequence:
(SEQ ID No. 65)
MKLPVRLLVLMFWIPASSSDVVMTQTPLSLPVSLGDQASISCRSSQSLVH

SNGNTYLHW-

YLQKPGQSPKLLIYKVSNRFSGVPDRFSGSGSGTDFTLKISRVE-

AEDLGVYFCSQSTHVPYTFGGGTKLEIKRADAAPTVSIFPPSSEQLTSGG

ASVVCFLNNFYPK.

According to a preferred embodiment, the antibody according to the present invention is a humanised antibody, especially an antibody comprising the following VH and VL amino acid sequence:

>hPRR13 VL (heavy chain variable region):
(SEQ ID No. 95)
EIVLTQSPSSLSASVGDRVTITCTASSSVTSSYLHWYQQKPGKAPKLLIY

STSNLAS-

GVPSRFSGSGSGTDFTFTISSLQPEDIATYYCHQYRRPPRTFGGGTKLEI

KR

>hPRR13 VH (heavy chain variable region):
(SEQ ID No. 96)
EVQLVESGPEVKKPGATVKISCKVSGYTFTDFYMKWVQQAPGRGLEWMGD

IDPKNG-

DTFYNQKFKGRVTMTADTSTGTAYMQLSSLTSEDTAVYFCASYYGYTMDY

WGQGTTVTVAS

>hC6-17 VL (light chain variable region):
(SEQ ID No. 97)
DIVMTQSPDSLAVSLGERATINCKSSQSLLNSRTRKNYLAWYQQKPGQPP

KLLI-

YWASTRESGVPDRFSGSGSGTDFTLTISSLQAEDVAVYYCKQSYNLLTFG

GGTKLEIK

>hC6-17 VH (heavy chain variable region):
(SEQ ID No. 98)
QVQLVQSGAEVKKPGASVKVSCKASGYTFTEYTMHWVRQAPGRGLEWMGG

INPN-

NGGTRYNQKFKGRVTMTRDTSIRTAYVELSRLTSDDTAVYYCASLDGRDY

WGQGTLVTVSS].

The antibodies according to the present invention may also be provided as antibody drug conjugates (i.e. coupled to a molecule that provides activity, e.g. which enhances phagocytic properties of the mAB), e.g. suitable to provide improved opsonophagocytic activity such as e.g. by modification of glycosylation or other modifications etc. Accordingly, the term "antibody" as used herein refers to an antibody being specific to HTT, especially to a specific epitope of HTT (or its naturally occurring fragments). The present invention also relates to HTT binding proteins that have a binding capacity to HTT or the HTT epitopes disclosed herein, for example to a scaffold antigen binding protein. Scaffold antigen binding proteins are known in the art, for example, fibronectin and designed ankyrin-repeat proteins (DARPins) have been used as alternative scaffolds for antigen-binding domains. In one embodiment a scaffold HTT binding protein is selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (transbody); ankyrin repeat protein (DARPin); peptide aptamer; C-type lectin domain (Tetranectin); human gamma-crystallin and human ubiquitin (affilins); PDZ domains; scorpion toxinkunitz type domains of human protease inhibitors; and fibronectin (adnectin); which has been subjected to protein engineering in order to obtain binding to a ligand other than the natural ligand.

The antibodies according to the present invention can be administered in any suitable dosage known from other mAB dosage regimen or specifically evaluated and optimised for a given individual. For example, the mABs according to the present invention may be provided as dosage form (or applies as dosage of) in an amount from 1 mg to 10 g, preferably 50 mg to 2 g, in particular 100 mg to 1 g. Usual dosages can also be determined on the basis of kg body weight of the patient, for example preferred dosages are in the range of 0.1 mg to 100 mg/kg body weight, especially 1 to 10 mg/body weight (per administration session).

A specifically preferred bispecific antibody comprises binding regions to more than one HTT epitope, especially to both, the PRR- and caspase region 586 domain, as defined herein.

In another aspect, the present invention provides monoclonal antibodies for use as a probe for drug screening that are based on the detection of cleaved versus non-cleaved Huntingtin or fragments or peptides derived thereof. In principle, M1D1 is able to detect peptide p7564 in contrast to p7605 (as shown in Example 5 FIGS. 16 and 17, respectively) thereby providing a means for quantifying protease activity at the relevant aspartic acid site 586 of this region of the Huntingtin protein.

It is especially preferred to use mAB M1D1 as disclosed by the present invention as probes for drug screening allowing for the differential detection of cleaved versus non-cleaved HTT. Based on the caspase 6 cleavage assay according to the present invention and provided e.g. in Example 10, it is possible to screen for AB's or other inhibitory molecules that specifically bind to the caspase region 586 of Huntingtin (as exemplified in FIG. 18) and thereby inhibit the accession of a proteases in general to this site (i.e. protease accession surrounding this position (aa 586), i.e. proteases aiming at this site (and not other sites of the HTT protein). In this assay, M1D1 is used as a probe to distinguish between Huntingtin and fragments thereof that were enzymatically cleaved at aspartic acid (position 586) or that were protected from cleavage by a cleavage inhibitor such as exemplified. For example, in the caspase cleavage inhibition assay according to the examples of the present invention, C6-17 (and several polyclonal antibodies—as shown in FIG. 19) are prototypic inhibitors. The use of this functional inhibitory activity of C6-17 (or of a derivative thereof, especially an intracellular derivative) in such assays or screening methods is subject matter of the present invention. For example, in Caspase 6 inhibitor screenings, M1D1 may be the probe and C6-17 may be the prototypic inhibitor.

It is especially preferred to use mAB C6-17 as prototypic inhibitor for caspase cleavage inhibition in this region of the Huntingtin protein i.e. as positive control inhibitor for benchmarking purpose for inhibitor screening assays as shown in Example 7 or as a basis for derivatization of a cleavage inhibitor in an antibody-derived format, specific to the caspase cleavage 586 region of Huntingtin, e.g. as shown in Example 7.

In yet another embodiment, the present invention provides a method for diagnosing in vitro Huntington's disease in a mammal, comprising the steps of: determining the level of free, aggregated, complexed or fragmented HTT in a sample of a mammal using the antibodies according to the present invention, especially the antibody PRR13, M1D1 and C6-17, in order to diagnose Huntington's disease, monitor disease progression or otherwise use HTT as biomarker if the level of HTT or enzymatically cleaved HTT in said sample is increased in comparison to a reference sample of healthy or individuals, who are genetically unaffected by Huntington's disease. In the course of the present invention it was shown that the pathology of Huntington's disease also correlates with the (low) amount of HTT present in plasma and other body fluids and tissue material. Determination of changes in such (low) HTT levels turned out to be possible with the antibodies according to the present invention, but are, of course, enabled also for other techniques after the disclosure of the present invention that changes in the HTT level are correlating to the disease and the disease status. It is therefore not only possible to diagnose the disease with the present tools but also to monitor the treatment of the disease.

Accordingly, the present invention provides a method for diagnosing in vitro Huntington's disease in a mammal, comprising the steps of:

determining the level of wild type or mutated Huntingtin or fragments thereof in a sample of a mammal using antibodies PRR13, M1D1 or C6-17 alone or in combination;

diagnosing Huntington's disease if the level of wt or mutated Huntingtin in said sample is increased in comparison to a reference sample of healthy individuals, who are genetically unaffected by Huntington's disease;

and, optionally, monitoring the effect of Huntingtin-lowering therapeutic strategies in pre-manifest or manifest Huntington's disease patient samples, wherein the therapeutic strategies are preferably selected from active or passive vaccination, especially in the course of a Huntingtin lowering therapy.

According to the present invention the determination of the level of mutated HTT in a sample involves preferentially immunoprecipitation- or capture-based assays such as Enzyme-linked Immunosorbent Assay (ELISA), enzyme-linked Immunoassay (EIA), Immunoprecipitations on other surfaces and carriers such as resins and beads, mass spectrometry, Fluorescence Resonance Energy Transfer (FRET) based assays, Western Blot or immune-histochemistry and immunofluorescence-based analysis such as FRET-based assays or suitable imaging methods (e.g. PET, SPECT) and Flow cytometry or any other techniques known to a person skilled in the art. Besides the mAbs according to the present invention also other HTT antibodies (e.g. those already reported in the prior art) can be integrated into such diagnostic assays.

According to the present invention the sample is preferably obtained from cerebrospinal fluid (CSF), blood, plasma, serum, urine saliva, sweat, or lacrimal fluid, or other body fluids or tissue- and cell extracts, especially brain tissue, muscle tissue and blood-derived cells, where (mutant) Huntingtin expression and structure is changed.

According to the present invention the mammal is preferentially a human being.

Moreover, the present invention provides a method for determining in vitro the stage of Huntington's disease or the effect of a new Huntingtin targeting therapy such as the represent actine or passive vaccination approach in a mammal, comprising the steps of:

determining the level of wild type or mutated Huntingtin or fragments thereof in a sample of a mammal using antibodies PRR13, M1D1 or C6-17 alone or in combination (these antibodies can be used alone or in combination for capturing an detecting Huntingtin protein or fragments with subsequent detection by biochemical means, Mass spectrometry or other analytical methods); and determining the stage of Huntington's disease.

Such determination is also possible via the levels of HTT in the given patient: This can be used to monitor the development of disease by comparing the (change of) HTT levels of a given patient over time (relative determination in the same individual) but also for initial diagnosing of the disease stage (absolute determination in correlation to a cohort of patients with a cohort of patients with a known disease status). The "change of HTT levels" will—at least in the longer run of treatment"—be a reduction in HTT levels so that e.g. plasma HTT levels in patients treated according to the present invention will go down (as e.g. depicted in FIG. 9). However, it is also possible that in some patients or at some stage of the disease, at the beginning of the treatment an increase of HTT levels may occur. This, nevertheless, is also indicative of a successful treatment, because e.g. an antibody can paradoxically stabilize a protein in the plasma but at the same time it blocks its pathological activity. In this case, a paradoxic initial increase of the targeted plasma HTT may be observed, although ABs against HTT have been administered. This phenomenon was e.g. seen in paradoxic IgE increase after anti-IgE treatment. Another example are—antibodies against growth hormone which lead to unexpected increase or its growth promoting effect due to stabilization.

Additionally, the present invention provides a method to monitor the progress of Huntington's disease or to monitor the effectiveness of treatment of Huntington's disease in a mammal, comprising the steps of:
  determining the level of mutated HTT in a sample of a mammal using PRR13, M1D1 and C6-17 according to the present invention and
  determining the progress of Huntington's disease or the effectiveness of treatment of Huntington's disease by comparing the obtained level of mutated HTT with the level of mutated HTT obtained in the first measurement of mutated HTT levels, preferably in a measurement at the time of diagnosis of the disease associated symptoms, wherein a change (which "change" is usually a lowering of HTT levels, at least in the longer run, as explained above) of the HTT level is indicative of a successful therapy and is preferably used for prognostic purpose and adjustment of the therapy.

Again, this method is enabled by the present invention because in the present invention effectivity of anti HTT vaccines has been shown for the first time. Also in these in vitro staging/monitoring methods, besides the mAbs according to the present invention also other HTT antibodies (e.g. those already reported in the prior art) can be integrated into such assays.

In these methods according to the present invention it is not critical to distinguish between "healthy" and "pathological" HTT (i.e. "wild type" or "mutated" HTT). This means that antibodies that cannot distinguish between these two forms (but bind to both forms) can be used for determining the level of HTT and are generally preferred in these methods.

In another embodiment, the present invention provides the use of at least one immunogenic peptide of the caspase region 586 of Huntingtin or another HTT region selected from the group consisting of p6773 (LPQPPPQAQPLL-PQPQPC, SEQ ID No. 1), p7564 (CPSDSSEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94); p7543b (TDN-QYLGLQIC; SEQ ID No. 89), p7543c (TDNQYL-GLQIGC; SEQ ID No. 90), p6771 (LPQPPPQAQPLLPC, SEQ ID No. 4), p8346 (CGPAVAEEPLHRP, SEQ ID No. 5), p8855 (SDSSEIVLDGTDC, SEQ ID No. 6), p8858 (EIV-LDGTDNQYLC, SEQ ID No. 7), p8859 (IVLDGTDN-QYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869 (CTDNQYLGLQIGQ, SEQ ID No. 12), p8868 (CGTDN-QYLGLQIG, SEQ ID No. 13), p8870 (CDNQYLGLQI-GQP, SEQ ID No. 14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PP-PQLPQPPPQAQPLLPQPQPaC, SEQ ID No. 19), p8854 (PSDSSEIVLDGTC, SEQ ID No. 20), p8856 (DSSEIV-LDGTDNC, SEQ ID No. 21), p8857 (SEIVLDGTDNQYC, SEQ ID No. 22), p8866 (NQYLGLQIGQPQC, SEQ ID No. 23), p8867 (QYLGLQIGQPQDC, SEQ ID No. 24), p6763 (CaMATLEKLMKAFESLKSFQ, SEQ ID No. 25), p6764 (CaKLMKAFESLKSFQ, SEQ ID No. 26), p6765 (CE-EQQRQQQQQQQ, SEQ ID No. 27), p6768 (QQQQQQP-PPPPPPaKKKC, SEQ ID No. 28), p7541 (CSEIVLD, SEQ ID No. 29), p7552 (CSSEIVLD, SEQ ID No. 30), p7562 (CDSSEIVLD, SEQ ID No. 31), p7563 (CSDS-SEIVLD, SEQ ID No. 32), p7567 (CEIVLD, SEQ ID No. 33), p7568 (CIVLD, SEQ ID No. 34), p7605 (CSEIVL, SEQ ID No. 35), p6776 (CSEIVLDGTDNQYL, SEQ ID No. 36), p6777 (CSDSSEIVLDGTDN, SEQ ID No. 37), p6776b (SEIVLDGTDNQYLC, SEQ ID No. 38), p7752 (CAEIV-LDGTDNQYL, SEQ ID No. 39), p7753 (CSAIVLDGTD-NQYL, SEQ ID No. 40), p7754 (CSEAVLDGTDNQYL, SEQ ID No. 41), p7755 (CSEIALDGTDNQYL, SEQ ID No. 42), p7756 (CSEIVADGTDNQYL, SEQ ID No. 43), p7757 (CSEIVLAGTDNQYL, SEQ ID No. 44), p7758 (CSEIVLDATDNQYL, SEQ ID No. 45), p7745 (CSEIV-LDGADNQYL, SEQ ID No. 46), p7746 (CSEIVLDGTAN-QYL, SEQ ID No. 47), p7747 (CSEIVLDGTDAQYL, SEQ ID No. 48), p7748 (CSEIVLDGTDNAYL, SEQ ID No. 49), p7749 (CSEIVLDGTDNQAL, SEQ ID No. 50), p7750 (CSEIVLDGTDNQYA, SEQ ID No. 51), preferably p6773 (LPQPPPQAQPLLPQPQPC, SEQ ID No. 1), p7564 (CPSDSSEIVLD, SEQ ID No. 2), p7543 (GTDNQYL-GLQIGC, SEQ ID No. 3), p6771 (LPQPPPQAQPLLPC, SEQ ID No. 4), p8346 (CGPAVAEEPLHRP, SEQ ID No. 5), p6776 (CSEIVLDGTDNQYL, SEQ ID No. 36), p6777 (CSDSSEIVLDGTDN, SEQ ID No. 37), p8855 (SDSSEIV-LDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDN-QYLGLQIGC, SEQ ID No. 11), p8869 (CTDNQYL-GLQIGQ, SEQ ID No. 12), p8868 (CGTDNQYLGLQIG, SEQ ID No. 13), p8870 (CDNQYLGLQIGQP, SEQ ID No. 14), p8871 (CNQYLGLQIGQPQ, SEQ ID No. 15), p6772 (CPQLPQPPPQAQPLLP, SEQ ID No. 16), p8864 (TDN-QYLGLQIGQC, SEQ ID No. 17), p8865 (DNQYLGLQI-GQPC, SEQ ID No. 18), p6775 (PPPQLPQPPPQAQPLL-PQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), and p8867 (QYL-GLQIGQPQDC, SEQ ID No. 24), especially p6773 (LPQP-PPQAQPLLPQPQPC, SEQ ID No. 1), p7564 (CPSDS-SEIVLD, SEQ ID No. 2), p7543 (GTDNQYLGLQIGC, SEQ ID No. 3), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), and p8346 (CGPA-VAEEPLHRP, SEQ ID No. 5), for the manufacture of a medicament for the prevention or treatment of Huntington's disease.

Preferably, these peptides are at least 7 amino acids, and preferred lengths may be up to 16, preferably up to 14 or 20 amino acids residues (e.g. 7 or 8 to 20, 7 or 8 to 16 etc.). Thus, the peptide of the present invention comprises 7 to 30, preferably 7 to 20, more preferably 7 to 16, most preferably 8, amino acid residues. According to the invention, however, also longer peptides may very well be employed as anti-HTT-antibody-inducing antigens.

In a preferred embodiment, the present invention relates to peptide-based vaccines for use in the prevention and/or treatment of Huntington's disease comprising at least one immunogenic peptide of the caspase region 586 of Huntingtin as defined above.

The immunogenic peptides may be provided in the vaccine in isolated (peptide) form or may be coupled or complexed (covalently or non-covalently) to other molecules, such as pharmaceutical carrier substances or polypeptides, lipid or carbohydrate structures, especially peptide linkers or protein carriers. Furthermore, the peptide linkers or protein carriers might consist of or contain T-cell helper epitopes.

In another aspect, the present invention relates to immunogenic peptides of the caspase region 586 of Huntingtin as specified above, wherein said peptides are used for the generation or identification of specific Huntingtin caspase region 586-cleavage inhibitors, e.g. such as shown in Example 7. According to the present invention such specific Huntingtin caspase region 586-cleavage inhibitors are defined as antibodies and antisera and structures derived thereof such as scFv's, Fab, Fd, Fab', F(ab')2, scFAB, intrabodies or Fv, or any other format, especially any of the preferred formats disclosed herein.

In a specifically preferred embodiment of the present invention antibodies or antigen-binding molecules targeting caspase region 586 of Huntingtin (HTT) are generated by immunisation with the above specified peptide-based vaccines comprising at least one immunogenic peptide of the caspase region 586 of Huntingtin as specified above or in combination, e.g. as demonstrated in Examples 2 and 3.

According to the present invention such antibodies or antigen-binding molecules are preferentially used in a pharmacological composition used in the prevention and/or treatment of Huntington's disease.

The invention is further disclosed by the following examples and the figures, yet without being limited thereto.

Figure 3:
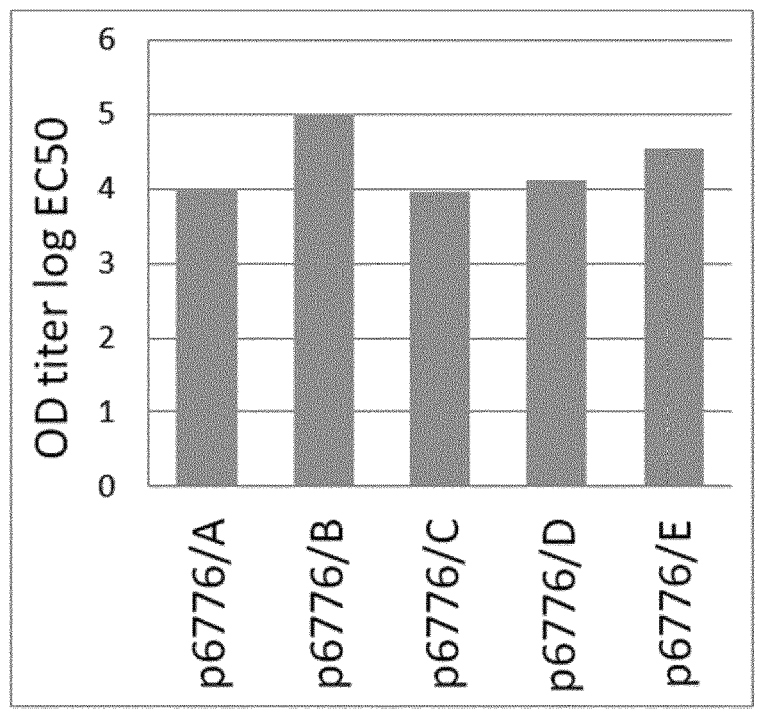
FIG. 3 shows that individual immunsera raised against immunization peptide p6776 provide comparable anti-peptide ELISA titers against the immunization peptide (indicated as log EC50).
Figure 4:
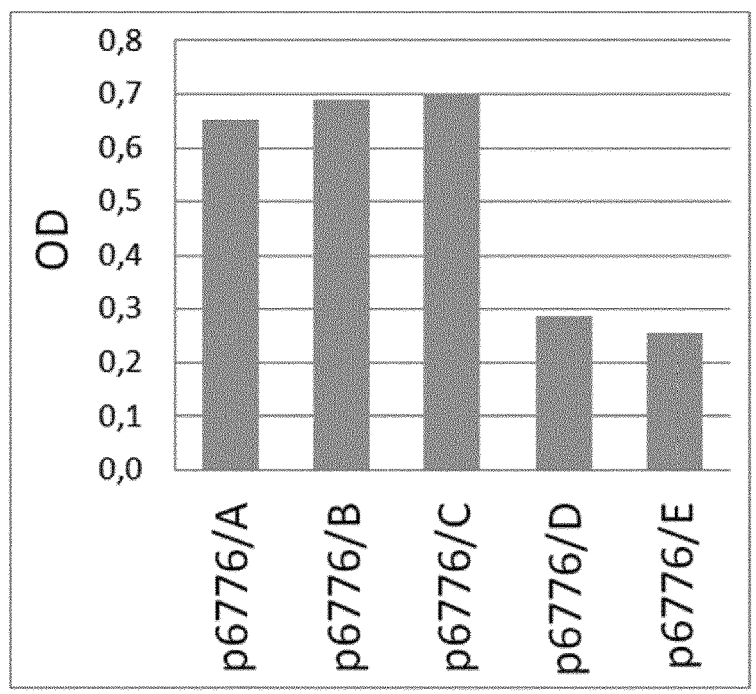

FIG. 4 shows that in contrast, the same immunsera of FIG. 3 show differences in anti recombinant Huntingtin signals as measured by protein capture ELISA (OD; anti recHTT610) thereby demonstrating individual variation of the immune response despite using the same immunogen. For a possible therapeutic application, the anti recHTT610 signal intensity and specificity is more relevant than the anti peptide titer.

Figure 5:
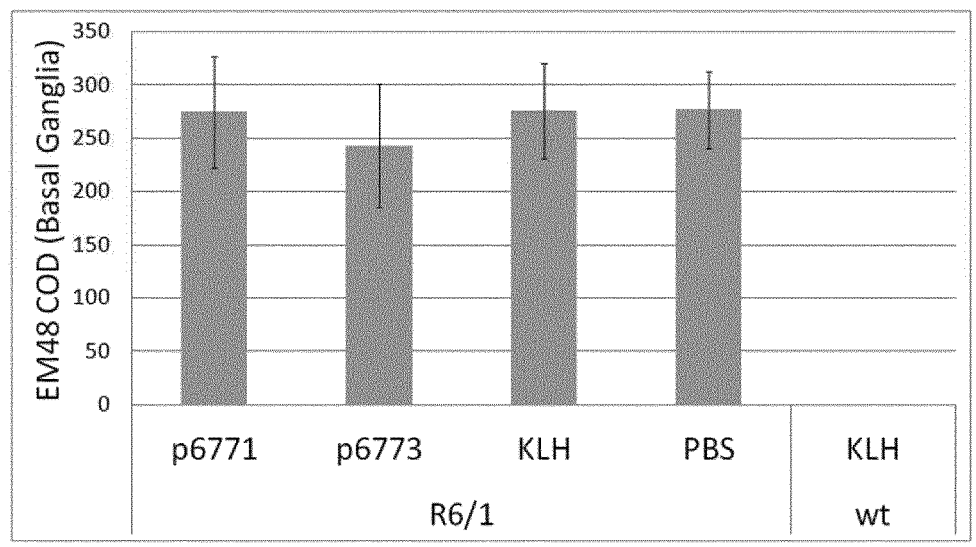

FIG. 5 shows no changes of Huntingtin signals (EM48) in peptide vaccine (p6771, p6773) treated R6/1 mice when comparing to KLH-carrier or PBS treated R6/1 mice or KLH-carrier-treated wild type mice (numbers indicate Corrected Optical Density [COD] using Huntingtin-specific mAB EM48; error bars=standard deviations; n=10).

Figure 6:
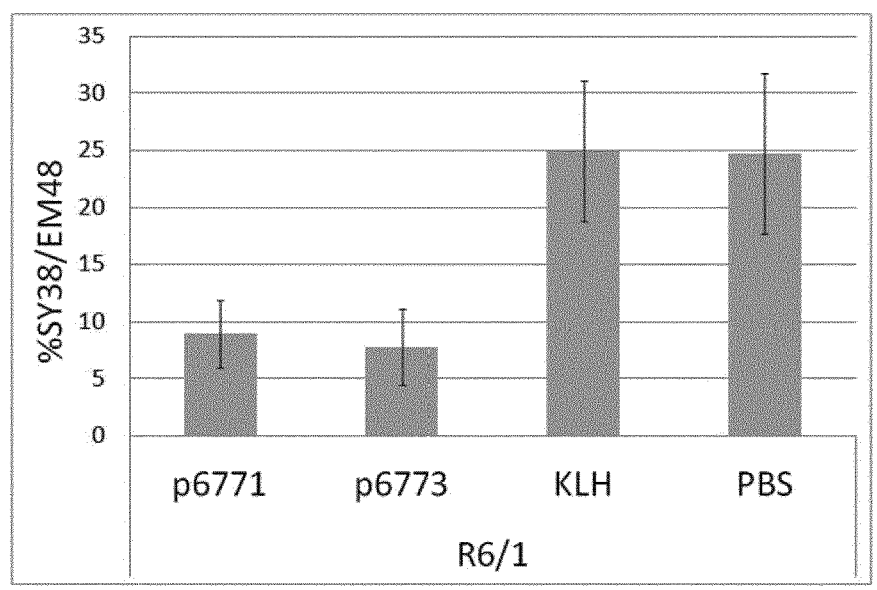

FIG. 6 shows that in contrast to the results from FIG. 5, the number of Synaptophysin-marked synapses (using mAB SY38) containing mutated human HTT (marked by EM48) is significantly reduced (p=0.001) in peptide vaccine-treated R6/1 mice (p6771, p6773) when compared to KLH treated R6/1 mice suggesting a beneficial effect of vaccine peptides.

Figure 7:
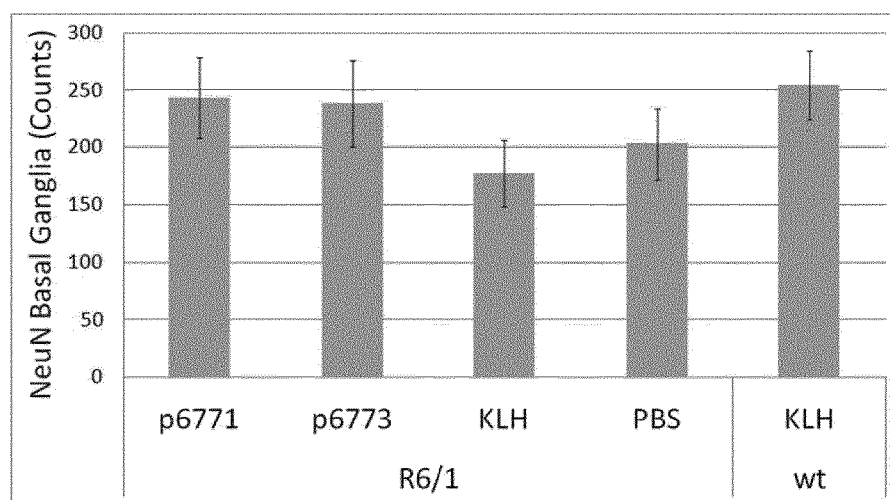

FIG. 7 shows that using neuron-specific marker NeuN, R6/1 mice display a significant neuroprotective effect in basal ganglia in the peptide vaccine-treated groups (p6771, p6773) when compared to control groups treated with KLH or PBS.

Figure 8:
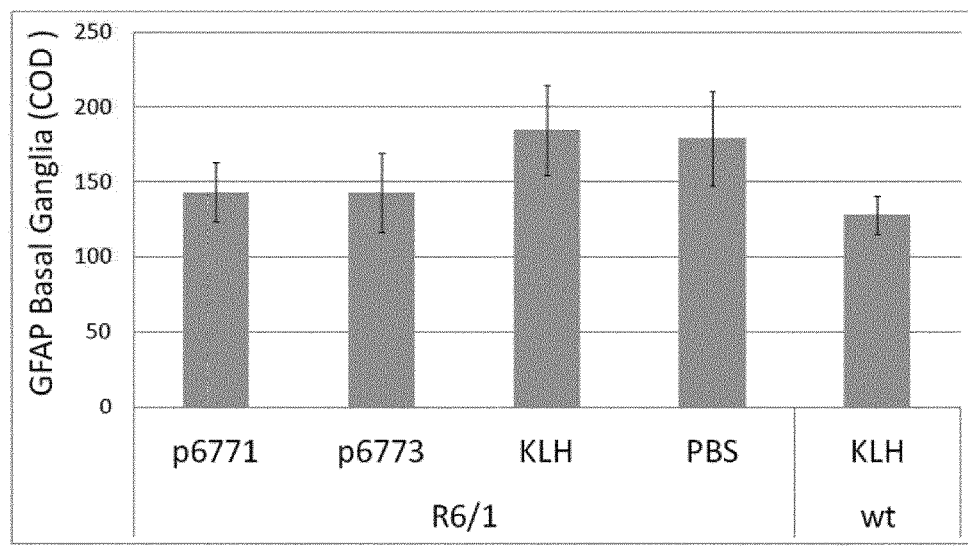

FIG. 8 shows that GFAP staining of basal ganglia shows nonsignificant reduction of astroglial activation in peptide vaccine treated R6/1 animals (p6771, p6773) when compared to KLH and PBS controls, respectively.

Figure 9:
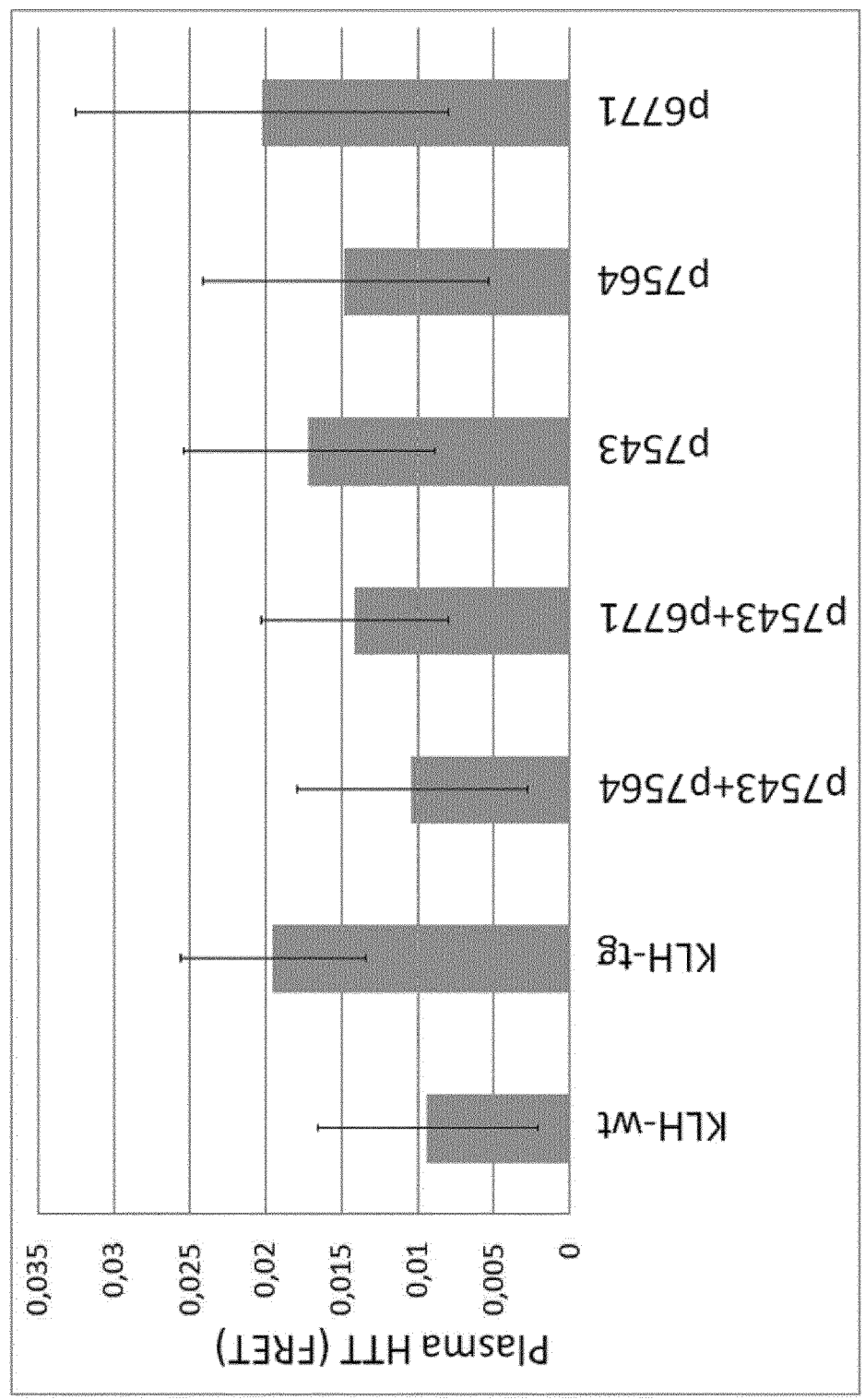

FIG. 9 shows plasma Huntingtin determination by FRET analysis in wt and YAC128 transgenic animals, respectively, at 12 months after single vaccine, combinatorial vaccine or carrier control (KLH) treatment.

Figure 10:
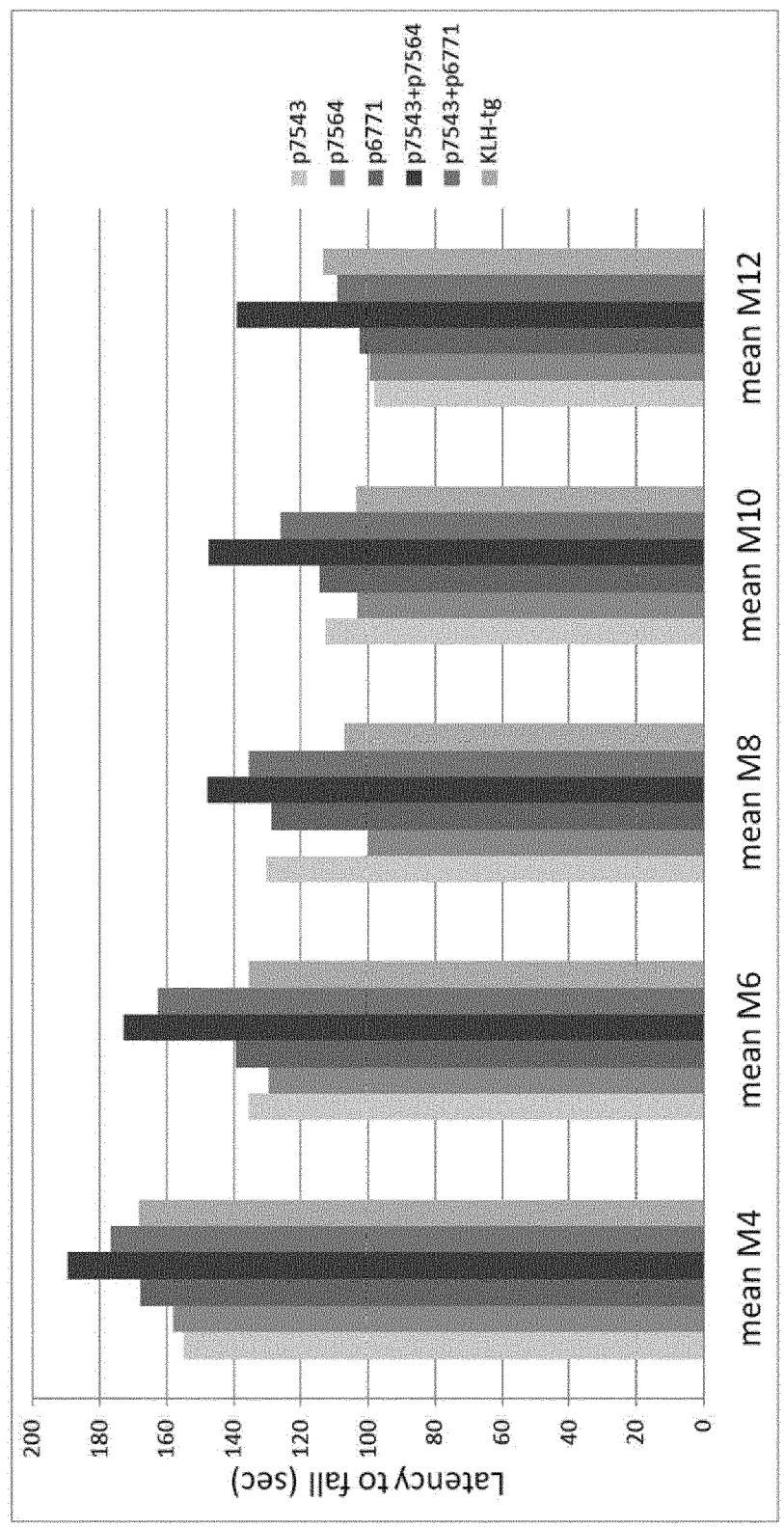

FIG. 10 shows Rotarod test in treated and control YAC128 mice measuring latency to fall (indicated as mean value in seconds; n=25 animals per group) performed at 4, 6, 8, 10 and 12 months (indicated as "mean M4"-"mean M12") in transgenic YAC128 mice treated with various single and combinatorial peptide vaccines as indicated.

Figure 11:
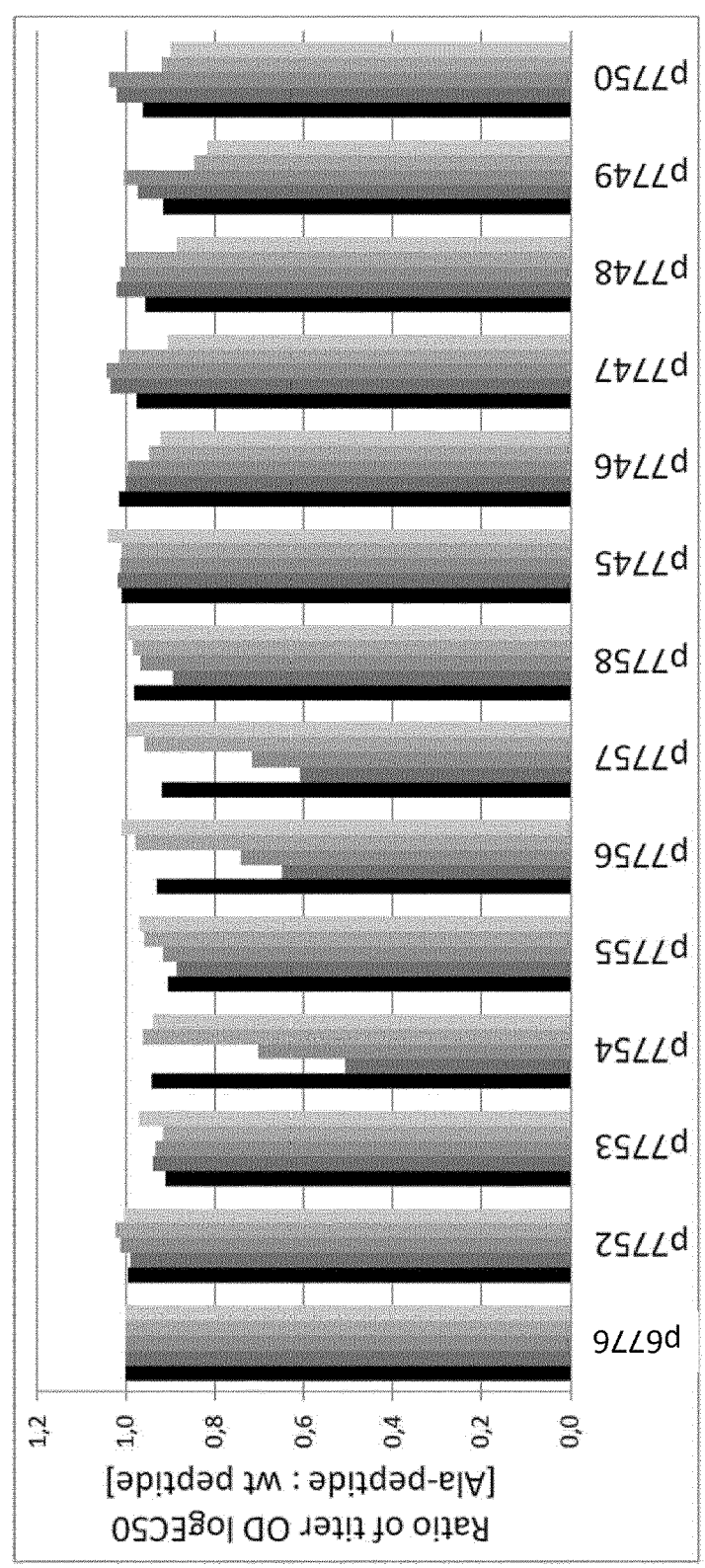

FIG. 11 shows the core epitope of 5 p6776 vaccine-induced immunsera determined by alanine substitution scanning by peptide ELISA using indicated peptides containing single amino acid alanine substitutions.

Figure 12:
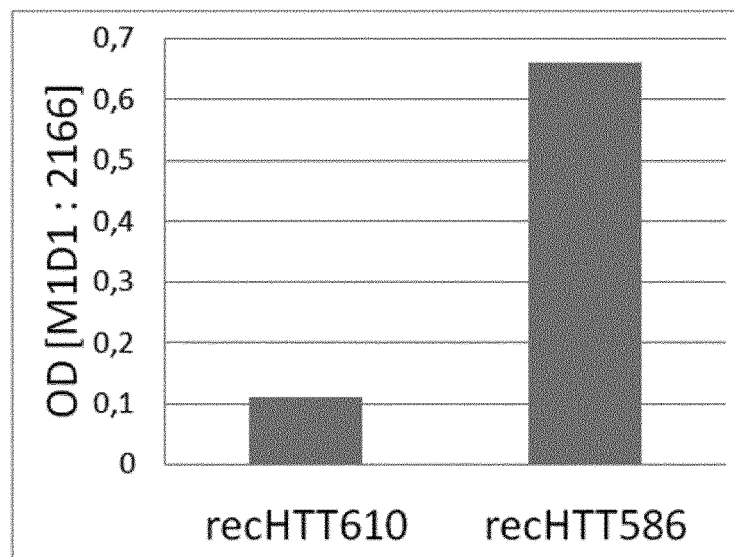

FIG. 12 shows that mAB M1D1 specifically recognizes recombinant Huntingtin fragment with free aspartic acid 586 at the C-terminus stronger than recHTT610.

Figure 13:
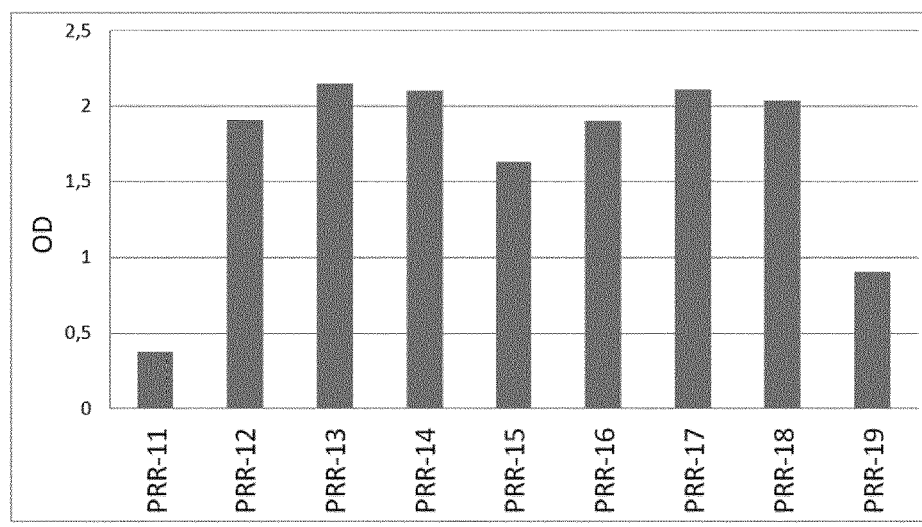

FIG. 13 shows that supernatants from hybridoma derived from mice immunized with peptide p6773 provide strong recognition of the immunization peptide in 7 out of 9 pre-screened candidate clones when tested by peptide ELISA.

Figure 14:
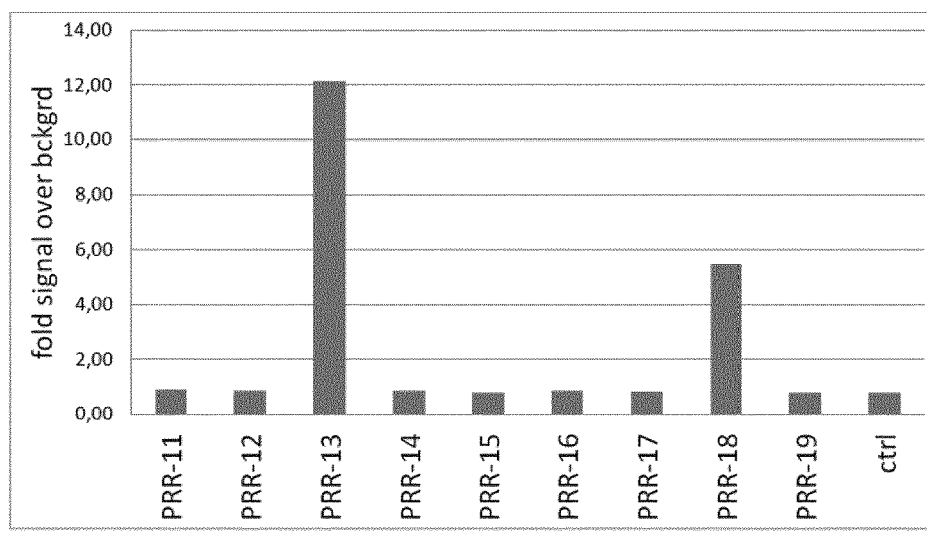

FIG. 14 shows that only 2 out of 9 mAB candidates shown in FIG. 13, namely PRR13 and PRR18, specifically recognize recombinant Huntingtin when tested by recHTT610 capture ELISA.

Figure 15:
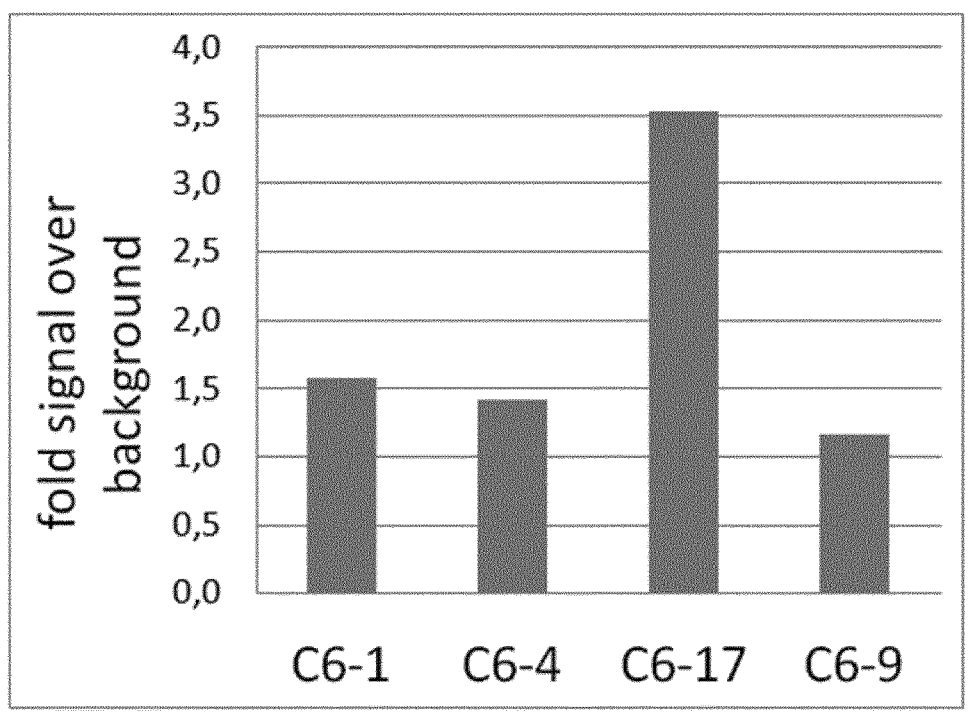

FIG. 15 shows the specificity analysis of 4 preselected anti Huntingtin mAB's derived from peptide p7543 immunized mice.

Figure 16:
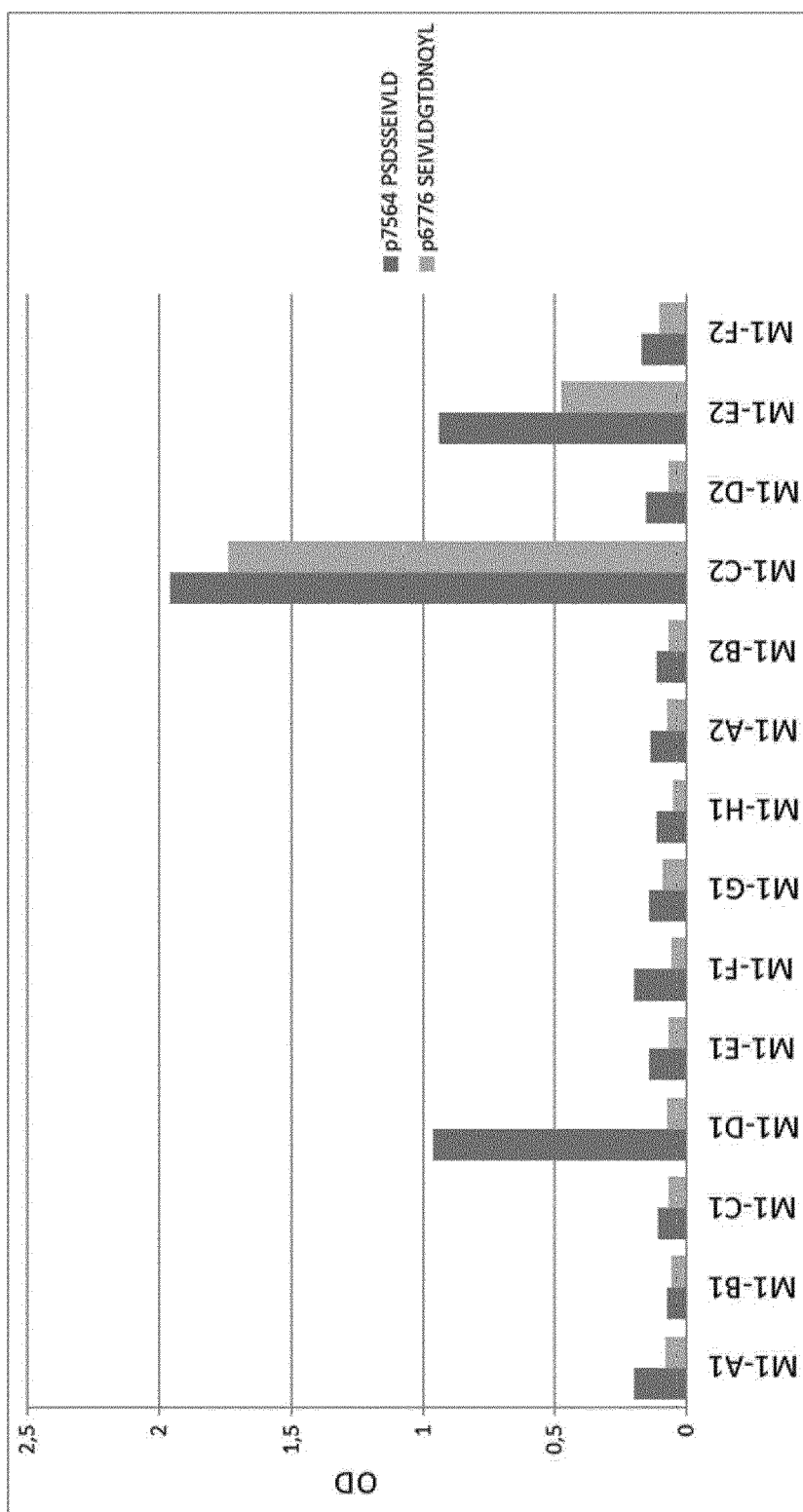
Figure 17:
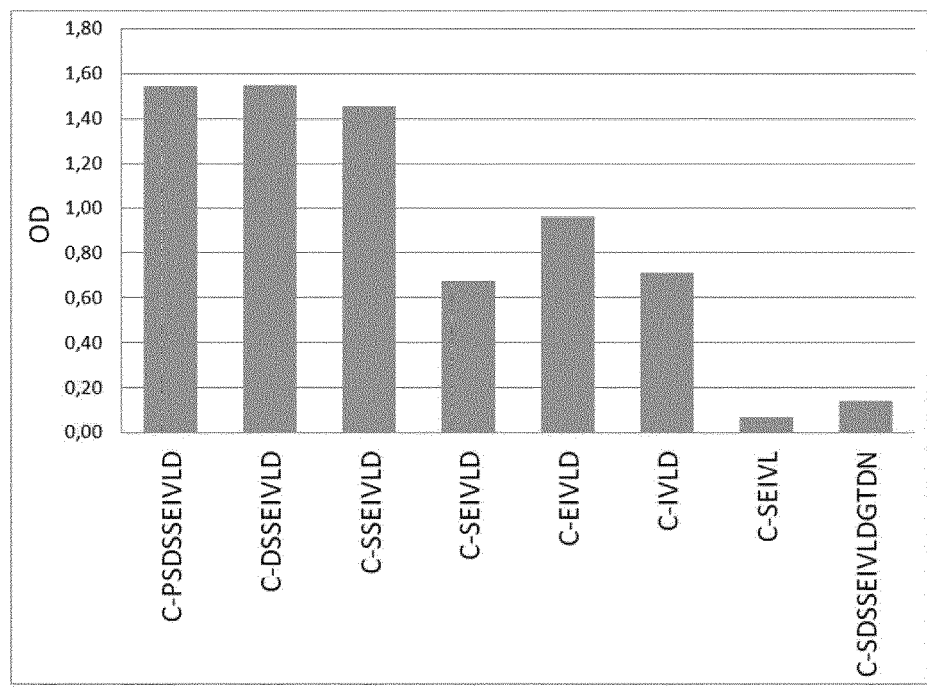

FIG. 16 shows screening of preselected mABs by determination of specificity against "cleaved" peptide p7564 by peptide ELISA FIG. 17 shows that mAB M1D1 recognizes Huntingtin peptides from the caspase region 586 of at least 7AA length containing free C-terminal Aspartic Acid.

Figure 18:
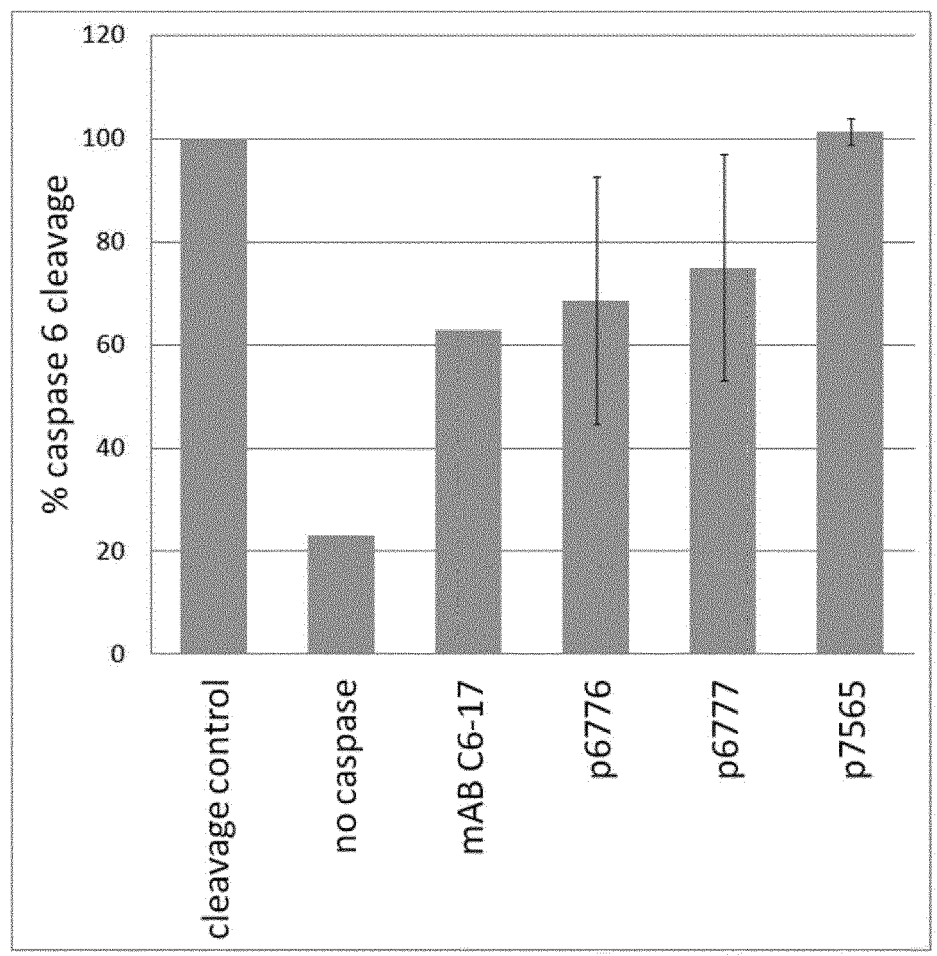

FIG. 18 shows in vitro caspase 6 cleavage inhibition assay for the purpose of screening Huntingtin sequence-specific protease inhibitors spanning caspase region 586.

Figure 19:
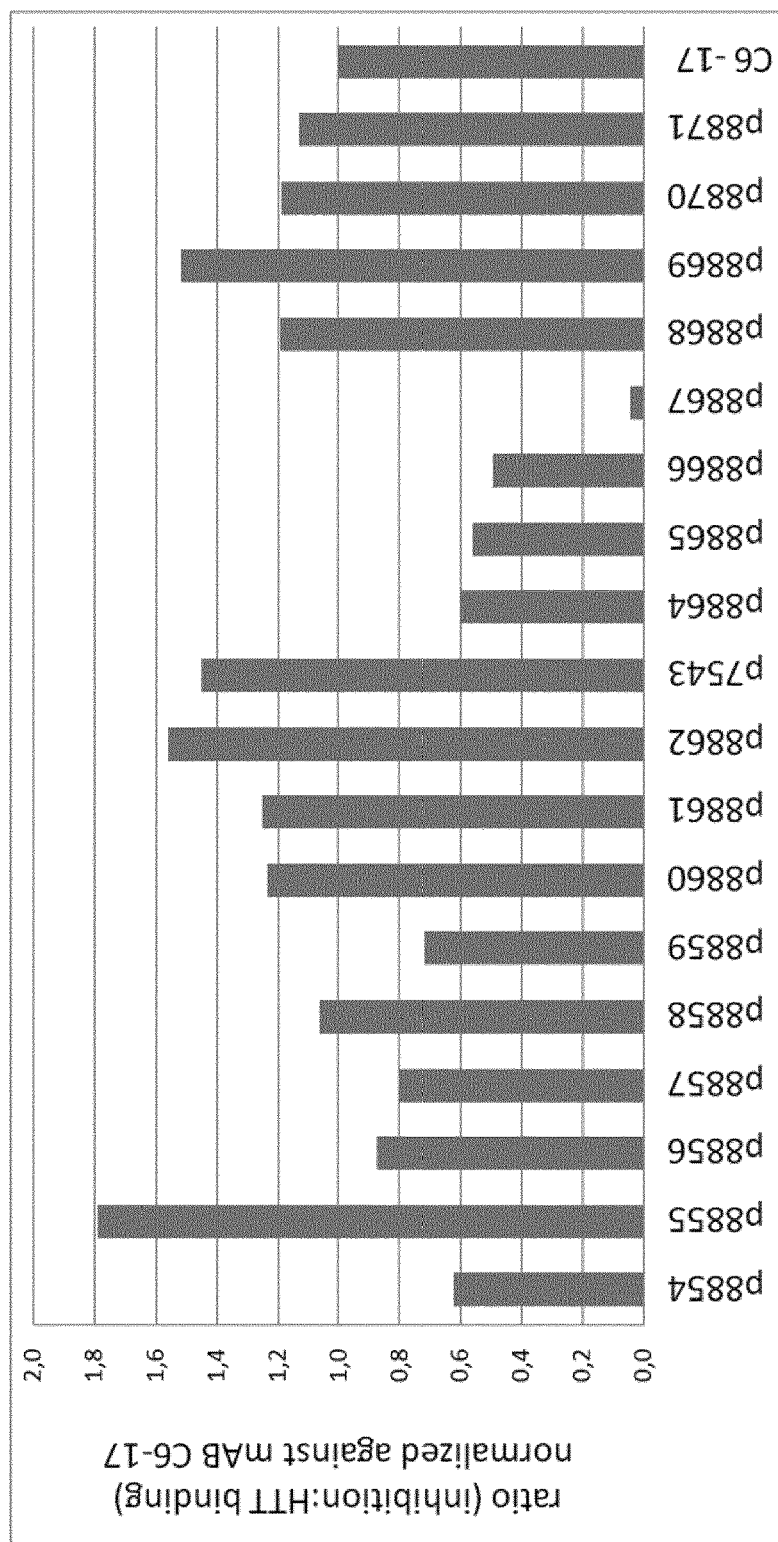

FIG. 19 shows in vitro caspase 6 cleavage inhibition assay of 18 polyclonal sera and mAB C6-17 as reference for the purpose of screening for the most efficient caspase site inhibitors.

Figure 20:
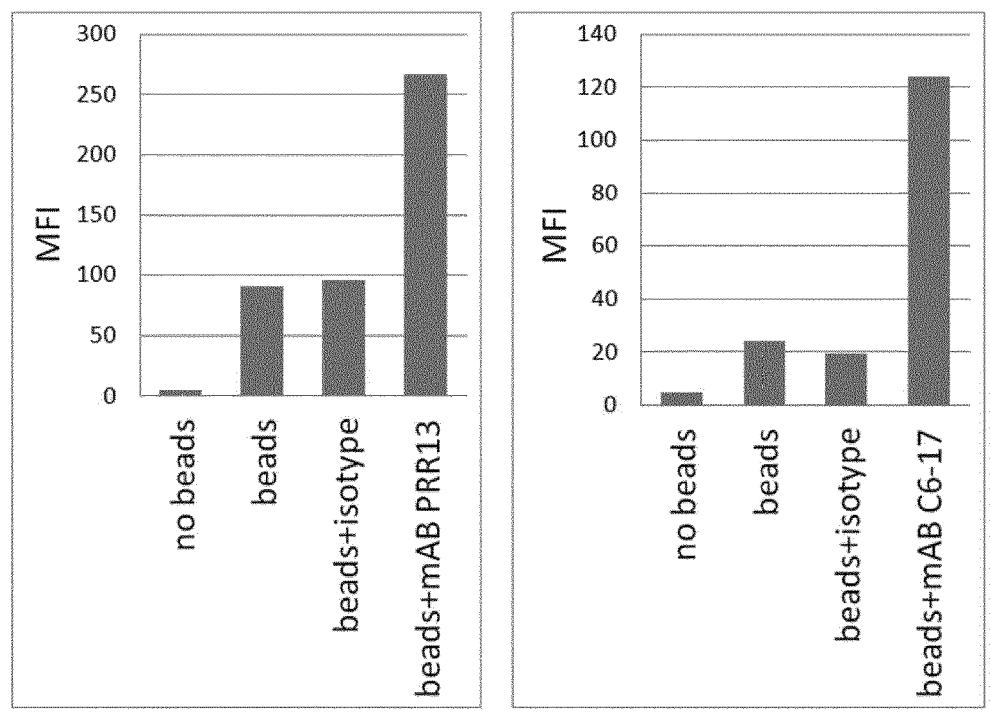

FIG. 20 shows in vitro phagocytosis assay showing phagocytic activity of PRR- and caspase cleavage 586 region derived monoclonal antibodies PRR13 and C6-17, respectively, recognizing human Huntingtin.

FIG. 21-26 show performance of modified versions of the peptides according to the present invention.

Figure 28:
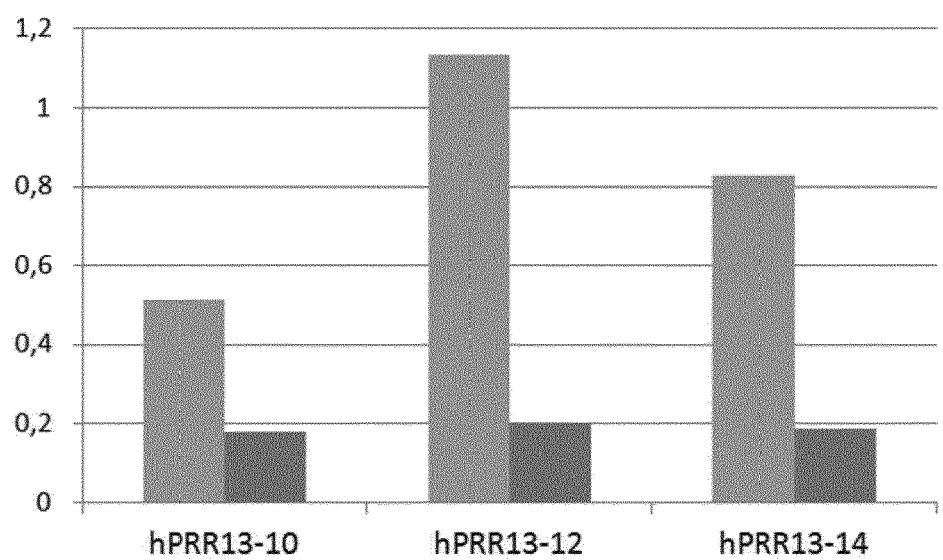
Figure 29:
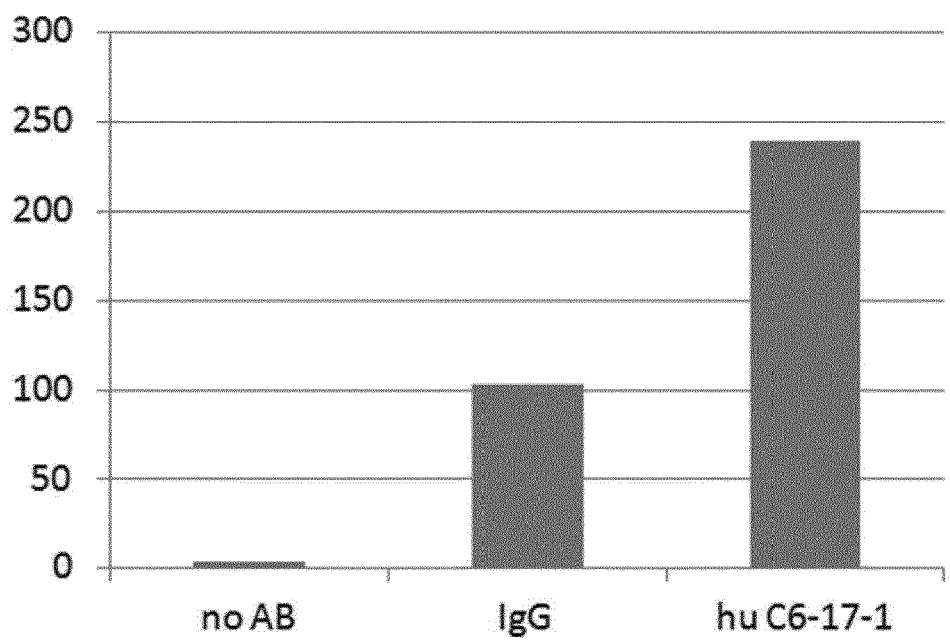

FIG. 27-29 show examples for antibody immunization.

EXAMPLES

Example 1

—Identification of Candidate Vaccine Peptides Targeting the Huntingtin N-Terminus Vaccines and Animal Immunizations Vaccine peptides were coupled to KLH carrier using GMBS as amine-sulfhydryl crosslinker (Thermo/Pierce, CatNr. 22309) according to standard recommended procedures for peptide coupling via Cystein. The conjugated peptide was formulated with Aluminium Hydroxide Gel adjuvant (1 µg/ml final concentration; Alhydro-gel; Brenntag, CatNr. 21645-51-2) using 30 µg coupled peptide in a volume of 200 µl per injection. Immunizations were typically performed in female BALB/c mice (typically 5 mice per group, aged 10 weeks) using above formulations. Control groups were immunized with non-conjugated KLH and/or PBS and adjuvant alone. Animals were vaccinated 3-6 times in regular intervals of 2 weeks and plasma or serum was collected one day before each boost and at final bleeding.

Peptide ELISA.

Vaccine-induced immune responses in mice were determined by ELISA using heparin as anticoagulant. ELISA plates (Nunc Maxisorb) were coated with maleimide activated BSA as carrier to which Cystein containing peptides were coupled via stable thioether bonds. For titrations, plasma dilutions were added and peptide-specific antibodies were quantified by biotinylated anti-mouse IgG (Southern Biotech, CatNr. 1034-08) as detection antibody combined with Streptavidin-POD (Roche, CatNr. 1089153) and subsequent color reaction using ABTS. EC50 values were determined using curve fitting with a 4-parameter logistic using GraphPad Prism (GraphPad Software).

Generation of Cell Extracts Containing N-Terminal Huntingtin Fragment recHTT610.

A DNA covering the coding region of the N-terminal 610 aminoacids of human Huntingtin protein extended by two C-terminal V5 tags were synthesized and cloned via XbaI and BamHI restriction sites into eukaryotic expression vector pCDH-EF1-MCS IRES Puro (SBI; CatNr. CD532A1) yielding plasmid precHTT610. Cloning procedures were performed according to standard molecular biology procedures essentially as indicated by manufacturers including restriction digestions and ligation reactions (NEB Quick ligase kit; CatNr. M2200L), bacterial transformation followed by clone selection and analysis. DNA fragment preparations from agarose gels were performed using standard DNA purification kits (Quiagen; CatNr. 27106). HEK293 freestyle cells (Invitrogen; CatNr. R790-07) were grown in medium as indicated by the manufacturer and transiently transfected with precHTT610 (or empty vector as control) using MAXreagent (Invitrogen; CatNr.16447-100) and Optimem (Gibco; CatNr.31985). 24-48 h after transfection, HEK cell lysates were obtained by cell lysis with NP-40 extraction buffer (150 mM NaCl, 1% NP-40, 50 mM Tris pH8), aliquoted and stored at −80° C. Protein concentrations were determined using Qubit (Invitrogen; CatNr.Q32866) according to the manufacturer's instructions.

Detection of Huntingtin by Protein Capture ELISA

Binding of antibodies to N-terminal fragment HTT610 was determined by a standard protein capture ELISA procedure using Maxisorb™ ELISA plates (Thermo; CatNr. 439454), coated with 50 µl of a 1:5000 rabbit anti V5 mAB (Sigma, CatNr. V8137), blocking with blocking buffer (PBS, 1% BSA, 0.1% Tween 20), capturing of recombinant Huntingtin from HEK cell extracts (100 ng/µl total protein) followed by incubation with several dilutions of mouse anti HTT sera (1:100; 1:300 and 1:900) or with mAB2166 as reference (diluted 1:2000; Millipore, Cat Nr. MAB2166) for 1 hour at RT. ELISA incubations, washing and detection procedures were performed according to standard procedures.

Affinity Purification of Antibodies from Plasma

Iodoacetyl-activated magnetic beads (BcMag™; Bioclone CatNr. FG-102) were conjugated with cysteine-containing peptides according to the manufacture's protocol. After plasma/mAB incubation for 2 h at RT, beads were washed with high salt buffer (PBS, 0.2% Triton X-100 supplemented to a final NaCl concentration of 350 mM), bound antibodies were recovered by acid elution (4 elution steps with 100 mM Glycine; pH2.8). After neutralization with a final concentration of 75 mM HEPES pH8, antibodies were concentrated to a volume of 100 µl using Spin-X UF500 tubes (Corning, CatNr. CLS431478), protein concentration was measured as described for protein extracts.

Figure 1:
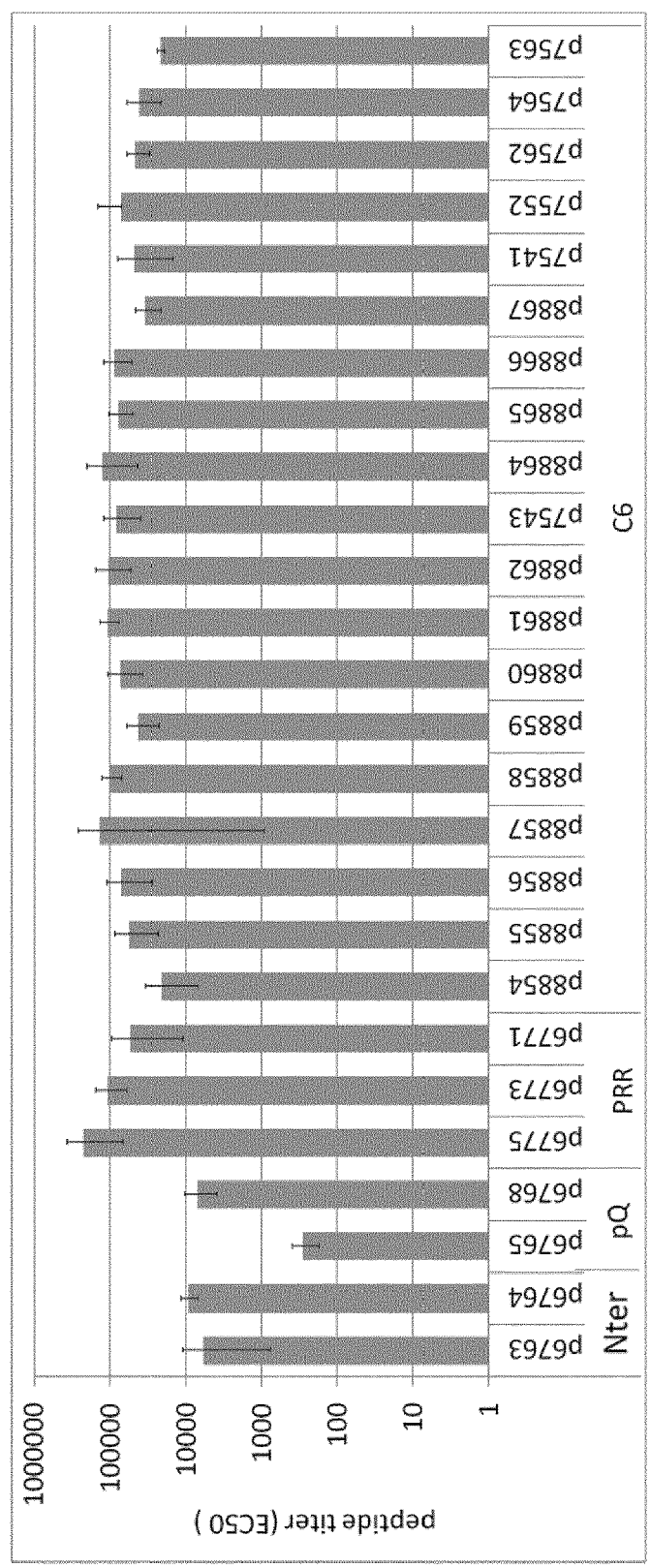
FIG. 1 shows immune-titer analysis by ELISA of candidate peptides derived from the PRR region and caspase region 586 of human Huntingtin (indicated as PRR and C6, respectively) in comparison to the less immunogenic N-terminal and poly-Q region of Huntingtin.

Results:

Immune sera from Huntingtin peptide-vaccinated mice show that peptides derived from the polyproline rich region (PRR) and caspase region 586 (C6) of the Huntingtin protein generally provide higher titers in peptide ELISA analysis (FIG. 1) than comparable peptide vaccines derived from the polyglutamine (polyQ) or N-terminal region (comprising the first 17 amino acids) of the protein, respectively. When analysed by protein ELISA (FIG. 2), PRR- and caspase region 586-derived immunsera, show differences in anti-Huntingtin protein signal intensity (FIG. 4) and protein specificity (FIG. 2) depending on the peptide sequences of the immunization peptides, allowing for the definition of specific and immunogenic vaccine peptide candidates. Peptide p7564 induces immunsera specifically recognizing Huntingtin sequences containing Aspartic Acid at the C-terminus (FIG. 3) thereby providing a means for addressing a diseasespecific Huntingtin neo-epitope generated by caspase cleavage of Huntingtin at position 586. FIG. 1: Immune-titer analysis by ELISA reveals that candidate peptides derived from the PRR region and caspase region 586 of human Huntingtin (indicated as PRR and C6, respectively), provide on average titers above 1:10000 in peptide-vaccine immunized mice, as opposed to animals immunized with polyglutamine region- or N-terminus-derived peptides (indicated as polyQ and Nter, respectively), where the average titers are below 1:10000. Titers are expressed as mean EC50 from 5 individual sera; error bars show standard deviations.

Figure 2:
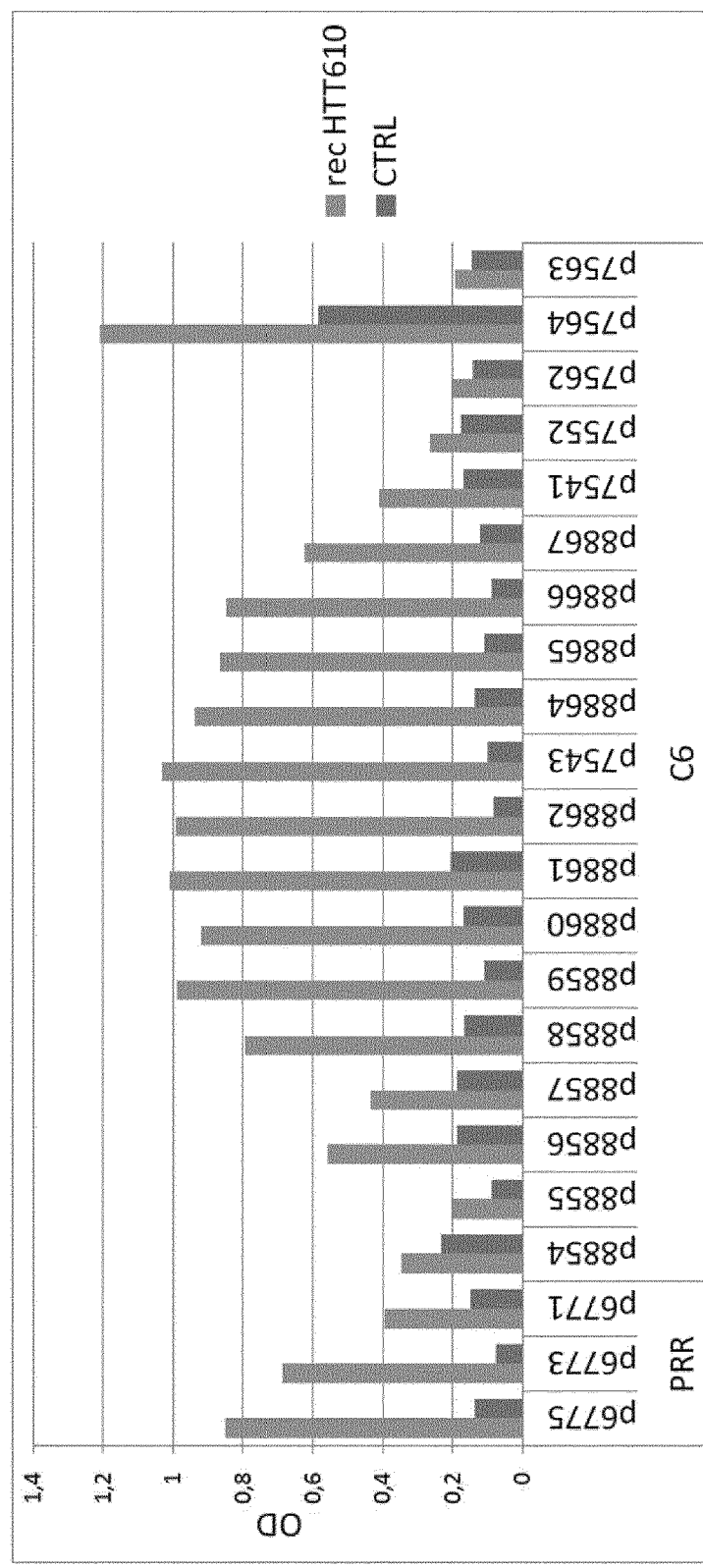
FIG. 2 shows mouse immunsera from candidate peptide vaccines derived from the PRR and caspase region 586 of human Huntingtin were screened by protein capture ELISA against a recombinant 610 amino acids N-terminal Huntingtin fragment captured from extracts of transiently transfected HEK cells showing binding and specificity.

FIG. 2: Mouse immunsera from candidate peptide vaccines derived from the PRR and caspase region 586 of human Huntingtin were screened by protein capture ELISA against a recombinant 610 aminoacids N-terminal Huntingtin fragment captured from extracts of transiently transfected HEK cells. Anti-Huntingtin ("recHTT610") and background signals ("CTRL") differ between different peptides despite a homogenous anti-peptide signal distribution as seen in peptide ELISA (shown in FIG. 1). Bars represent signals from 5 pooled immunsera each, tested either against recombinant Huntingtin (OD[recHTT610 extract]; light grey bars) or control extracts (OD[mock transfected ctrl extract]; dark grey bars), respectively at serum dilutions of 1:100.

FIG. 3: 5 Individual immunsera raised against immunization peptide p6776 provide comparable anti-peptide ELISA titers against the immunization peptide (indicated as log EC50).

FIG. 4: In contrast to anti-peptide titers (shown in FIG. 3), the same immunsera show differences in anti recombinant Huntingtin signals as measured by protein capture ELISA (OD; anti recHTT610) thereby demonstrating individual variation of the immune response with respect to the target protein but not to the peptide. This emphasizes that for therapeutic vaccine peptide selection, anti recombinant HTT signals are more relevant than anti peptide titers.

Example 2

—Peptide Immunization of Transgenic R6/1 Mice Over-Expressing the First Exon of Mutant Human Huntingtin Provides Beneficial Changes Reflected by Neuropathological Markers in Basal Ganglia R6/1 mice expressing exon 1 of human mutant Huntingtin under a relatively strong promoter (see Bard et al. 2014 and citations therein) were subjected to vaccine injections at week 8, 10, 14 and 24 formulated as in Example 1. For monitoring titers, plasma was collected at 8, 16, 28 and 32 weeks.

Immunohistochemistry

Analysis by immunohistochemistry was essentially performed as described in Mandler et al. 2014 [PMID: 24525765] using antibodies EM48, SY38, GFAP and NeuN for marker protein detection basal ganglia (Millipore, CatNr. MAB5374, MAB5258, AB5804 and MAB377, respectively).

Results:

Immunohistochemical analysis of basal ganglia of peptide vaccine-immunized 6 months old transgenic R6/1 mice, overexpressing the first exon of mutant human Huntingtin. The effect of peptide vaccination was compared by histopathological comparison of peptide p6771 and p6773-immunized with control groups (KLH, PBS). A clear neuroprotective and Huntingtin-reducing effect in synapses was observed upon vaccination with PRR-derived vaccines.

FIG. 5: No changes of Huntingtin signals (EM48) in peptide vaccine (p6771, p6773) treated R6/1 mice when comparing to KLH-carrier or PBS treated R6/1 mice or KLH-carrier-treated wild type mice (numbers indicate Corrected Optical Density [COD] using Huntingtin-specific mAB EM48; error bars=standard deviations; n=10).

FIG. 6: In contrast, the number of Synaptophysin-marked synapses (using mAB SY38) containing mutated human HTT (marked by EM48) is significantly reduced (p=0.001) in peptide vaccine-treated R6/1 mice (p6771, p6773) when compared to KLH treated R6/1 mice (Student's ttest; n=10 animals per treatment group). Numbers indicate the ratio (in %) of SY38-positive synapses co-localizing with EM48 signals (error bars=standard deviations; COD=Corrected Optical Density).

FIG. 7: Using neuron-specific marker NeuN, R6/1 mice display a significant neuroprotective effect in basal ganglia in the peptide vaccine-treated groups (p6771, p6773) when compared to control groups treated with KLH or PBS (p=0.002 and p=0.01, resp. Student's ttest; n=10).Wt KLH=wild type controls; numbers indicate Corrected Optical Density (COD); error bars=standard deviations.

FIG. 8: GFAP staining of basal ganglia shows nonsignificant reduction of astroglial activation in peptide vaccine-treated R6/1 animals (p6771, p6773) when compared to KLH and PBS controls, respectively (COD=Corrected Optical Density; wt KLH=wild type controls; error bars=standard deviations).

Example 3

Combinatorial Vaccine Treatment Leads to Reduced Plasma Huntingtin Levels in YAC128 Transgenic Mice Combined with Motoric Improvement as Measured by Rotarod Test in 4-12 Months Old Animals YAC128 Mouse Immunizations Five cohorts of full length mutant human Huntingtin expressing YAC128 mice (see Bard et al. 2014 and citations therein) and WT control littermates were assembled consisting of 150 total YAC128 and 25 total WT. WT mice were treated with KLH control. YAC128 mice were divided into 6 treatment groups including 5 experimental peptide treatments and a KLH control group. Mice received treatments by s.c. injection at 1, 2, 3, 6 and 9 months of age as in Example 1. For combination vaccines, the total peptide amount of 30 µg per dose was kept by combining two peptides at 15 µg+15 µg each per 200 µl volume dose.

Determination of Plasma Huntingtin Levels in Vaccine Treated YAC128 Mice

Plasma Huntingtin levels were determined by FRET (Förster resonance energy transfer)-based detection assay yielding the ratio between the two detection antibodies as previously described by Weiss et al. 2009 [PMID: 19664996].

Rotarod Test

Two-month-old YAC128 mice were trained over 3 consecutive days on the rotarod (Ugo Basille) at a fixed speed of 18 revolutions per minute (RPM). Mice received 3×120 s training trials per day with a 1 h inter-trial interval (ITI). Mice that fell from the rod were immediately replaced for the duration of the trial. The latency to the first fall and number of falls for each training trial were recorded. The average of the 3 trials for each mouse was scored. For longitudinal rotarod testing at 2 month intervals from 2 to 12 months of age, an accelerating program from 5 RPM to 40 RPM over 300 s was used. Mice received 3 trials with a 1 h ITI and the latency to the first fall was recorded. The average of the 3 testing trials was scored.

Results:

FIG. 9: Plasma Huntingtin determination by FRET analysis in wt and YAC128 transgenic animals, respectively, at 12 months after single vaccine, combinatorial vaccine or carrier control (KLH) treatment. Peptide vaccines from the PRR and caspase region 586 regions were used (p6771 and p7564&p7543, respectively). Significant reduction of plasma Huntingtin can be achieved by combinatorial treatment using peptide combinations p7543+p7564 or p7543+p6771, when comparing plasma Huntingtin levels to carrier control treatment (KLH) (p<0.001 and p<0.01, respectively; Student's ttest; n=25 animals per treatment group). Numbers indicate relative units (FRET); error bars indicate standard deviations.

FIG. 10: Rotarod test in treated and control YAC128 mice measuring latency to fall (indicated as mean value in seconds; n=25 animals per group) performed at 4, 6, 8, 10 and 12 months (indicated as "mean M4"-"mean M12") in transgenic YAC128 mice treated with various single and combinatorial peptide vaccines as indicated. Notably, the combinatorial vaccine groups "p7543+7564" and "p7543+p6771" showed overall better performance in this test when compared to single peptide treated groups p7543, p6771 and 7564, respectively. Motoric improvement was significantly improved at M4-M10 in combination vaccine group p7543+7564 when compared to carrier control groups (p<0.03, 0.02, 0.01, resp.; Student's ttest, n=25). This finding parallels plasma Huntingtin reduction as described in FIG. 9.

Example 4

Epitope Mapping of Monoclonal and Polyclonal Antibodies Obtained by Immunisation with Peptides p6773, p7564 and p7543

Determination of Core Epitopes

Peptide epitope mapping was performed using alanine substitution scanning by determination of titer values (OD [EC50]) by ELISA as explained in Example 1 or alternatively by applying peptide microarrays as described by Stadler et al. 2008 or single amino acid substitution scanning with peptide microarrays. In brief, peptides containing single alanine-substitutions each position of the peptide were spotted on the arrays, and the loss of signal due to substitutions at single positions was determined by fluorescence labelled secondary antibodies in combination with a Odyssey Imaging System by LI-COR Biosciences. This allowed for an evaluation of the contribution of each individual amino acid of the peptide to the epitope. Using this method, the original immunization peptide to be mapped plus single alanine-substituted variants for each individual position or the peptide were spotted onto microarrays and hybridized by the respective monoclonal antibodies or immune sera to be tested. When the resulting signal from an alanine-substituted peptide was reduced to less than 70% of the signal from the original immunization peptide, the respective alanine-substituted amino acid position was defined as part of the core epitope. Resulting core epitope sequences are provided below from individual sera or mAB's.

Results:

Polyclonal, affinity purified antibodies and monoclonal antibodies were derived from individual mice immunized with PRR-region derived peptides (including p6771 and p6773) and caspase region 586-derived peptides (including p7543 and p6776). Epitopes were mapped using alanine scanning. In brief, epitopes of individual sera and monoclonal antibodies were determined by testing antibodies against peptides with single amino acid substitutions for each position using either peptide microarrays or conventional peptide ELISA (as exemplified in FIG. 11)

Peptide and epitope alignments for PRR region-derived peptides p6771 and p6773 as determined by single amino acid substitution scanning:

```
                         (SEQ ID Nos. 1, 4 and 77-81)
LPQPPPQAQPLLPC......immunization peptide p6771

LPQPPPQAQPLLPQPQPC..immunization peptide p6773

..........LLPQP.....epitope mapped for mAB PRR13

....PPQAQPL.........epitope mapped for polyclonal
p6773 serum 1

....PPQAQP..........epitope mapped for polyclonal
p6773 serum 2

........QPLL........epitope mapped for polyclonal
p6773 serum 3

.....PQAQPLL........epitope mapped for polyclonal
p6773 serum 4
```

Peptide and epitope alignment of p7543 vaccine induced polyclonal immunsera and mAB C6-17 as determined by single amino acid substitution scanning:

```
                           (SEQ ID Nos. 3 and 82-86)
GTDNQYLGLQIGC    immunization peptide p7543

QYLGLQIG    epitope mapped for monoclonal
                AB C6-17

YLGLQIG    epitope mapped for polyclonal
                p7543 serum 1

DNQYLGLQIG   epitope mapped for polyclonal
                p7543 serum 2

DNQYLGL    epitope mapped for polyclonal
                p7543 serum 3

YLGLQIG    epitope mapped for polyclonal
                p7543 serum 4
```

Peptide and epitope alignments for caspase region 586 derived peptides spanning aspartic acid 586:

FIG. 11: The core epitope of 5 p6776 vaccine-induced immunsera was determined by alanine substitution scanning by peptide ELISA using indicated peptides containing single amino acid alanine substitutions. The 5 sera (represented by dark to bright bars) were hybridized to alanine substituted peptides as indicated (for peptide sequences see table 1). As a result, 2 out of 5 animals showed signal reduction upon alanine substituted peptides p7754, p7756, p7757 and p7758, respectively, thereby delineating a core epitope with the amino acid sequence IVLD for polyclonal antisera. Numbers indicate the ratio of titer OD (log $EC_{50}$) [Ala-substituted peptide: wt-peptide].

Epitope mapping of p7564 induced antisera and mAB M1D1 is provided in Example 5, FIG. 17.

FIG. 12: mAB M1D1 specifically recognizes recombinant Huntingtin fragment with free aspartic acid 586 at the C-terminus stronger than uncleaned recHTT610. Protein ELISA (performed as in Example 1) using recombinant Huntingtin with 610 and 586 amino acids length (HTT610 and HTT586, respectively). Values indicate the ratio of the mAB M1D1 signal (OD; protein capture ELISA as explained in Example 1) to the mAB 2166 control antibody signal. Values were normalized to reference mAB 2166 recognizing an internal epitope present in both fragments as protein loading control.

Example 5

Generation and Characterisation of Monoclonal Antibodies PRR13, C6-17 and M1D1

Monoclonal Antibodies

For the production and isolation of monoclonal antibodies, the ClonaCell-HY Hybridoma Cloning Kit (STEMCELL technologies, CatNr. 28411) was used according to the instructions of the manufacturer. In brief, hybridoma fusions were performed with myeloma cell line SP2-0 under HAT selection and supernatants were initially screened by peptide ELISA using the immunization peptide, respectively, and an irrelevant control peptide for background determination. In the case of M1D1, ELISA against peptide p6776 containing free C-terminal aspartic acid was used in order to determine specificity to cleaved peptide with free C-terminal aspartic acid as indicated in Example 5. Candidate mABs were affinity purified as described and tested against recHTT610 by protein ELISA as indicated in Example 1. The number of screened fusion clones was typically 500 for each fusion, respectively. For VL and VH region sequencing, mRNA from fusion clones was extracted, reverse transcribed using Oligo(dT) primers and PCR amplified using variable domain primers to amplify both the VH and VL regions. VH and VL products were cloned using standard PCR cloning procedures (Invitrogen, CatNr. K4560-01), transformed into TOP10 cells and screened by PCR for positive transformants. Selected colonies were picked and analyzed by DNA sequencing on an ABI3130xl Genetic Analyzer.

Affinity Purification of Antibodies mABs and polyclonal antibodies were isolated from hybridoma supernatant (SN) and plasma, respectively using BcMag™ Iodoacetyl activated magnetic beads (Bioclone, FG-102) to which cysteine containing peptides were linked according to the manufacture's protocol. After plasma/SN incubation for 2 h at RT, beads were washed with high salt buffer (PBS, 0.2% Triton X-100, supplemented with NaCl to a final concentration of 350 mM) and the bound antibodies eluted 4 times with acidic elution buffer (Thermo, CatNr. 21004). After neutralization in HEPES pH8 (75 mM end concentration), eluted antibodies were concentrated and buffer was exchanged to PBS to a volume 100 µl using Spin-X UF500 tubes (Corning, CLS431478). Antibody concentrations were determined with the Qubit system (Invitrogen, CatNr.Q32866) according to the manufacturer's protocol.

Results:

Antibody PRR13 was generated by hybridoma technique using peptide p6773 as immunogen. Peptide p6773 is one of the vaccine candidates that shows beneficial neuroprotective effects in actine immunization of R6/1 transgenic animals as shown in Example 2 and overlaps with p6771. PRR13 was selected from 9 preselected candidate mABs recognizing a PRR-derived peptide as shown in FIG. 11. Out of the candidate mABs listed in FIG. 13, PRR13 was selected based on its favorable signal/noise ratio when hybridized to recombinant HTT610 as shown in FIG. 12.

FIG. 13: Supernatants from hybridoma derived from mice immunized with peptide p6773 provide strong recognition of the immunization peptide in 7 out of 9 pre-screened candidate clones when tested by peptide ELISA.

FIG. 14: In contrast to specific anti peptide signals (FIG. 11), only 2 out of 9 mAB candidates, namely PRR13 and PRR18, specifically recognize recombinant Huntingtin when tested by recHTT610 capture ELISA (as explained in Example 1). These two candidates provided an outstanding signal to noise ratio (i.e. >=4; calculated reHTT610-specific signal: HEK ctrl extracts), and PRR13 was selected for epitope characterization (see Example 4) and variable chain sequencing (see below). PRR13 was determined as IgG subtype mouse IgG2a.

>PRR13 VH Consensus Amino Acid Sequence
(SEQ ID No. 62):
MGWSWVMLFLLSGTGGVLSEVQLQQSAPELVKPGASVKMSCKASGYSFTD

FYMKWVKQSH-

GKGLEWIGDIDPKNGDTFYNQKFKGRATLTVDKSSSTAYMQLNSLTTEDS

AVYY-

CATYYGYTMDYWGQGTSVTVSSAKTTAPSVYPLAPVCGDTTGSSVTLGCL

VKGYF

>PRR13 VL Consensus Amino Acid Sequence
(SEQ ID No. 63):
MDFQVQIFSFLLISASVIMSRGQIVLTQSPAIMSASLGERVTMTCTASSS

V-

TSSYLHWYQQKPGSSPKLWIYSTSNLASGVPARFSGSGSGTSYSLTISS-

MEAEDAATYYCHQYRRPPRTFGGGTKLEIKRADAAPTVSIFPPSSEQLTS

G-

GASVVCFLNNFYPR

Antibody C6-17 was generated by hybridoma technique using peptide p7543 as immunogen. Peptide p7543 showed beneficial therapeutic effects in YAC128 transgenic animals as demonstrated in Example 3. Although anti recHTT610 signals were comparable between 4 preselected mABs from this screen as shown in FIG. 13, the signal to noise ratios differed significantly amongst these candidates as shown in FIG. 14 showing a recHTT610 capture ELISA (performed as in Example 1). Based on its specificity and IgG subtype (determined as mouse IgG2a), C6-17 was selected for epitope characterization (see Example 4) and variable chain sequencing:

FIG. 15: Specificity analysis of 4 preselected anti Huntingtin mAB's derived from peptide p7543 immunized mice. Values for 4 mAB candidates represent signal to noise ratios of recombinant Huntingtin-specific OD-signal against control extract (determined by protein capture ELISA as explained in Example 1). mAB C6-17 provides the best signal to noise ratio.

>C6-17 VH Consensus Amino Acid Sequence
(SEQ ID No. 60):
MGWSCIMLFLLSGTAGVLSEVQLQQSGPELVKPGASVKISCKTSGYTFTE

YTMHWVKQSH-

GKSLEWIGGINPNNGGTRYNQKFKGKATLTVDRSSSTAYMELRSLTSEDS

AVYYCASLD-

GRDYWGQGTTLTVSSAKTTAPSVFPLA

>C6-17 VL Consensus Amino Acid Sequence
(SEQ ID No. 61):
MVLMLLLLWVSGTCGDIVMSQSPSSLAVSAGEKVTMSCKSSQSLLNSRTR

KNYL-

AWYQQKPGQSPKLLIYWASTRESGVPDRFTGSGSGTDFTLTISSVQAED-

LAVYSCKQSYNLLTFGAGTKLELKRADAAPTVSIFPPSSEQLTSGGASVV

CFLNNFYPK

Antibody M1D1 was generated by hybridoma technique using peptide p7564 as immunogen. Peptide p7564 is part of the vaccine candidates that show beneficial therapeutic effects in YAC128 transgenic animals as demonstrated in Example 3. Monoclonal antibody M1D1 was selected by differential screening of binding to peptides containing a free aspartic acid at the C-terminus against a peptide containing this Aspartic Acid residue embedded within the sequence such as e.g. p6776, as shown in Example 1, FIG. 3. Based on its specificity for the "cleaved" sequence, monoclonal antibody M1D1 was selected for further epitope characterization and variable chain sequencing. It was typed as mouse IgM and it binds to the neo-epitope of a human Huntingtin fragment that is generated upon cleavage of the protein or a corresponding peptide sequence by caspase 6 or any other protease cleaving at amino acid position D586.

FIG. 16: Screening of preselected mABs by determination of specificity against "cleaved" peptide p7564 by peptide ELISA (as explained in Example 1). In contrast to e.g. M1-C2, mAB M1D1 shows the most favorable p7564 to p6776 OD signal ratio. M1D1 is therefore specific to the neo-epitope generated by proteolytic cleavage at position 586. The C-terminal aspartic acid of p7564 corresponds to the C-terminal cleavage point generated by caspase 6 and possibly other caspases. It thereby provides the means for specific cleavage detection at this site in analogy to polyclonal antisera generated with therapeutically beneficial peptide p7564 as shown in Example 3.

FIG. 17: mAB M1D1 recognizes Huntingtin peptides from the caspase 6 cleavage region of at least 7AA length containing free C-terminal Aspartic Acid. In contrast, shorter peptides or peptides without free C-terminal Aspartic Acid are not or only weakly recognized by M1D1 thereby demonstrating specificity of this monoclonal antibody for the cleaved sequence with free COOH-terminal aspartic acid such as the free amino acid position 586 of cleaved human Huntingtin protein (Bars represent OD from peptide ELISA at a mAB concentration of 1 ng/µl; peptide designations from left to right are as follows: p7564, p7562, p7552, p7541, p7567, p7568, p7605, p6777).

>M1D1 VH Consensus Amino Acid Sequence
(SEQ ID No. 64):
MDFGLSWVFFVVFYQGVHCEVQLVESGGGLVQPKGSLKLSCAASGFTFNT

YAMNWVR-

QAPGKGLEWVARIRSKSNNYATYYADSVKDRFTISRDDSQSMLYLQMNNL

KTEDTAMYYCVRH-

GEYGNPWFAYWGQGTLVTVSAESQSFPNVFPL

>M1D1 VL Consensus Amino Acid Sequence
(SEQ ID No. 65):
MKLPVRLLVLMFWIPASSSDVVMTQTPLSLPVSLGDQASISCRSSQSLVH

SNGNTYLHW-

YLQKPGQSPKLLIYKVSNRFSGVPDRFSGSGSGTDFTLKISRVE-

AEDLGVYFCSQSTHVPYTFGGGTKLEIKRADAAPTVSIFPPSSEQLTSGG

ASVVCFLNNFYPK

Example 6

—Caspase Cleavage Site Inhibitors

In Vitro Caspase Cleavage Inhibition Assay

Caspase 6 inhibition assays were performed using Maxisorb ELISA plates (Thermo; 439454) whereby 50 µl of 20 nM BSA-coupled peptide (as indicated in FIG. 18) was coated for 1 hour at RT followed by a one hour treatment with 150 µl blocking buffer (PBS, 1% BSA, 0.1% Tween 20), incubation for 1 hour at RT with affinity purified polyclonal sera (3 ng/µl) or affinity purified mABs (10 ng/µl) as indicated, respectively. After several washes with washing buffer (PBS, 0.1% BSA, 0.1% Tween 20), 5 U Caspase 6 enzyme (Enzo; BML SE170-5000) diluted in 1× Caspase 6 Buffer (BioVision; 1068-80) was added to each well and incubated for 30 min at 37° C. Quantification of the newly exposed epitope generated by caspase 6 peptide cleavage that reflected the extent of caspase accessibility was performed by ELISA as described in Example 1 using peptide p7564-induced antibodies for detection of the free C-terminal aspartic acid-containing epitope.

Results:

Polyclonal antisera targeting caspase region 586 of human Huntingtin were generated by peptide vaccines comprising peptides shown in FIG. 19. Even though all candidate peptides derived from the caspase region 586 induce comparable anti peptide titers (as exemplified in Example 1), relative caspase 6 inhibition varies in a peptide sequence and epitope-dependent manner thereby demonstrating differences in epitope accessibility and binding properties between peptide induced antibodies from this region. In particular, peptides spanning the caspase cleavage site 586, in particular p6776 and p6777 (as shown in FIG. 18) and peptides mapping C-terminally of the caspase cleavage site 586 such as for example p8855, p8862&p7543 and p8869 (as shown in FIG. 19), respectively, provide effective caspase 6 inhibitors such as determined by the caspase cleavage inhibition assay. When comparing the inhibitory effect of antibodies induced by peptides p8868, p8869, p8870 and p8871 with peptides p7543, p8864, p8865 and p8866, respectively, it can be demonstrated that the inhibitory activity of resulting antibodies is not substantially influenced by the N- or C-terminal position of the cysteine thereby suggesting flexibility with respect to the immobilization linker position. Based on these in vitro functional activities combined with the in vivo effects demonstrated in Example 3 and the in vitro phagocytic-activity demonstrated in Example 11, these peptides delineate a functionally relevant targeting domain for the antibody-based strategies presented in this patent application including active or passive immunization, plasma apheresis and competitive cleavage inhibitors binding to this region.

FIG. 18: In vitro caspase 6 cleavage inhibition assay for the purpose of screening Huntingtin sequence-specific protease inhibitors spanning caspase region 586. A plate-immobilized target peptide spanning caspase region 586 was incubated either with affinity purified polyclonal antibodies p6776, p6777, and p7565 as negative control (each at a concentration of 3 ng/µl) or with monoclonal antibody C6-17 derived from peptide immunization with p7543. mAB C6-17 was used as prototypic reference inhibitor at a concentration of 10 ng/µl. The antibody-protected target peptide was incubated with caspase 6 enzyme followed by detection of proteolytic cleavage efficiency of the target peptide. Cleaved peptide was detected using mAB M1D1 as probe capable of distinguishing a cleaved from non-cleaved Huntingtin sequence such as described in Example 5, FIG. 18. Numbers on the left indicate % cleavage indicating that no protection cleaves at 100% whereas mAB C6-17 and polyclonal antibodies p6776 and p6777 reduce cleavage as indicated by protecting the target peptide from caspase accession.

FIG. 19: In vitro caspase 6 cleavage inhibition assay of 18 polyclonal sera and mAB C6-17 as reference for the purpose of screening for the most efficient caspase site inhibitors. The assay was performed exactly as indicated in FIG. 18 whereas relative caspase cleavage activity was put in relation to target binding signal of each individual antibody tested. The values therefore indicate the ratio of relative caspase site inhibition (% cleavage as in FIG. 10) to target peptide binding determined by peptide ELISA (OD; as described in FIG. 1). This screening identified several peptides that are able to generate polyclonal antibodies capable of inhibiting caspase site 586 cleavage irrespective of the position of the terminal cysteine as demonstrated by peptides p8868, p8869, p8870 and p8871 which are different from peptides p7543, p8864, p8865 and p8866, respectively only with respect to their cysteine position but equally active and immunogenic. Despite relatively homogenous binding of antibodies to the peptide substrate (as shown in Example 1, FIG. 1), cleavage inhibition differed amongst induced antibodies in a peptide immunogen-dependent manner.

Example 7

—In Vitro Phagocytosis Assay Showing In Vitro Phagocytic Activity for mABs PRR13 and C6-17, Respectively Corroborating the In Vivo Mechanism of Action of Vaccine-Induced Antibodies Specifically Directed Against Immunogenic Peptides Derived from Human HTT Such as Tested in Example 2 (FIG. 6) and 3 (FIG. 9), Respectively In Vitro Phagocytosis Assay:

Isolation and in vitro differentiation of macrophages was essentially performed as described e.g. in Zhang et al. 2008 [PMID: 19016445]. In brief, tibia- and femur-derived bone marrow cells from 8 to 12 weeks old BALB/c mice were divided onto 2-3 10 cm-cell culture dishes at a density of 20-30×10⁶ cells per dish, differentiated 4 days in RPMI/10% FCS+P/S in the presence of 20 ng/ml M-CSF (RD-Systems, Cat-No: 416-ML-010), redistributed at day 5 into 24-well tissue culture plates at a density of 150.000 cells/well until day 9. 24 hrs before phagocytosis, cells were starved in 500 µl RPMI-media+10% FCS+P/S in absence of M-CSF. Phagocytosis was performed using streptavidin-coated paramagnetic microspheres (Bang Laboratories, Cat-No: CP01F), coated according to the instructions of the manufacturer with C-terminally biotinylated peptides p9304 and p9305 (p9304 (C6): b-GGGDYKDDDDKGAVTPSDS-SEIVLDGTDNQYLGLQIGQPQDG (SEQ ID No. 52); p9305 (PRR): b-GGGDYKDDDDKGPPPQLPQPPPQAQ-PLLPQPQPG (SEQ ID No. 53)), respectively and incubated with 10 ng/µl antibody in dilution buffer for 1 hr at RT followed by washing with PBS supplemented with NaCl to a final salt concentration of 350 mM, washing with PBS and by final resuspension in RPMI medium. Antibody-coated fluorescent peptide-beads were subsequently added to differentiated macrophages for 1 hr at 37° C. (in a volume of 200 ul containing 0.5 ug beads/well) allowing for in vitro uptake by phagocytosis. After washing and scraping the cells in ice cold PBS, cells were washed in FACS-Buffer (1×PBS+1% BSA) and analysed for fluorescence signal by standard FACS procedure. Cell differentiation efficacy was monitored in parallel using anti F4/80 (Biolegend, Cat-No: B123109) and anti CD11b (Biolegend, Cat-No: B101219) marker antibodies based on the protocol suggested by the manufacturer.

Results:

FIG. 20: In vitro phagocytosis assay showing phagocytic activity of PRR- and caspase cleavage 586 region derived monoclonal antibodies PRR13 and C6-17, respectively, recognizing human Huntingtin. Peptides p9304 (derived from the caspase cleavage 586 region; right panel) and p9305 (derived from the PRR region; left panel) were immobilized on fluorescent streptavidin beads, incubated with 5 ng/µl antibodies and transferred to in vitro MCSF-differentiated bone marrow derived primary mouse macrophages (for 7 days) as indicated in Methods. After 1 hr incubation with the beads, cells were measured for specific bead uptake by FACS analysis. mAB PRR13 (left panel) and C6-17 (right panel) show increased phagocytosis of beads when compared to isotype control antibody (i.e. mouse IgG2a).

Table 1: Preferred peptide uses (peptide name/peptide region/peptide sequence (C is for coupling to carrier protein; can be provided at N- or C-terminus of the peptide), except for p7564, p7541, p7552, p7562, p7563, p7567 or p7568, where a free C-terminal aspartic acid is required for the epitope); peptide list indicating name designations, mapping to protein region (region: Nter=N-terminus, polyQ=polyglutamine stretch, PRR=poly proline rich region, Ex1=mapping to exon 1, C6=caspase cleavage 586 region) and amino acid sequences (single letter code; Nter>Cter; a=beta-alanine; b=biotin)

Example 8

—Modified Variations of the Peptides According to the Present Invention

The following examples provide evidence that structural or chemical modifications of peptides can improve solubility of peptides thereby facilitating synthesis, purification, coupling or analytics necessary for vaccine preparation and quality control without negatively influencing immunogenicity, epitope properties or the quality of the immune response for vaccine applications.

As an example, C- or N-terminal Lysines were added to prototypic candidate peptide p7543 which improved solubility. As described here, the addition of one or several terminal lysines e.g. in peptides p9394 (KTDNQYLGLQI-GKC), p9395 (GTDNQYLGLQIGKKC), p9396 (KTDN-QYLGLQIKKGC) or p9397 (KDNQYLGLQIKKGC) provides improved water solubility. Peptide solubility was classified by inspection into "insoluble", "intermediate" (i.e. visible pellet after 5 min centrifugation at 14 krpm at RT) and "clear" (i.e. no visible pellet after centrifugation). While peptide p7543 had intermediate water solubility, peptides p9394, p9395, p9396 and p9397 were clear and showed good water solubility. Similar solubility improvements can be achieved using other peptide modifications commonly used for improving water solubility such as e.g. the addition of other charged amino acids (e.g. Arginines) or the addition of PEG modifications to the peptide without affecting the peptide epitope and immunogenicity.

The present example shows a characterization of lysine-modified variants of the peptides according to the present invention. Experimentally determined lysine variants with improved solubility include e.g. p9394 (KTDNQYLGLQI-GKC), p9395 (GTDNQYLGLQIGKKC), p9396 (KTDN-QYLGLQIKKGC) or p9397 (KDNQYLGLQIKKGC) containing one or more N- or C-terminally added Lysines in order to improve water solubility.

Figure 21:
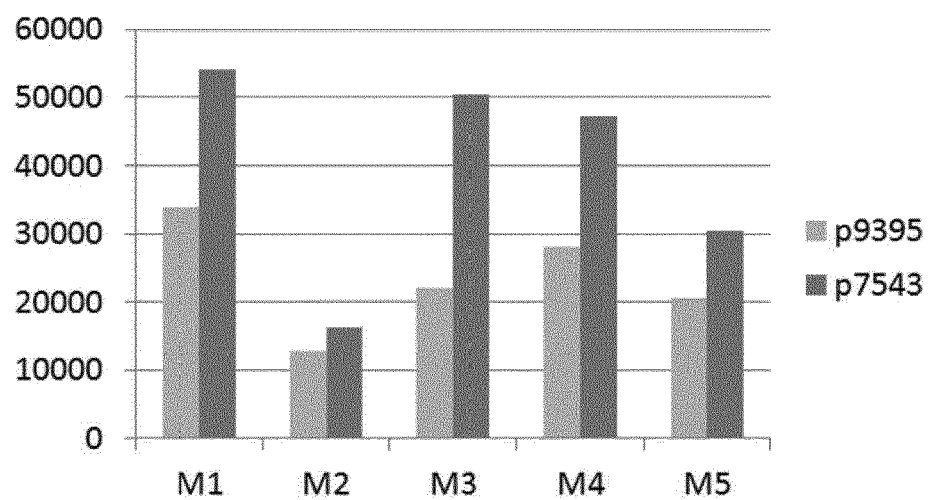

FIG. 21: a): Immunesera from 5 animals (M1-M5) that were immunized with C-terminally-modified peptide p9395 (as an example) show even stronger binding to the original wt sequence peptide (p7543) when compared to their binding to the immunization peptide (p9395). The results are depicted in FIG. 21. The Y-axis shows EC50 values for peptide ELISA as performed in Example 1.

Figure 22:
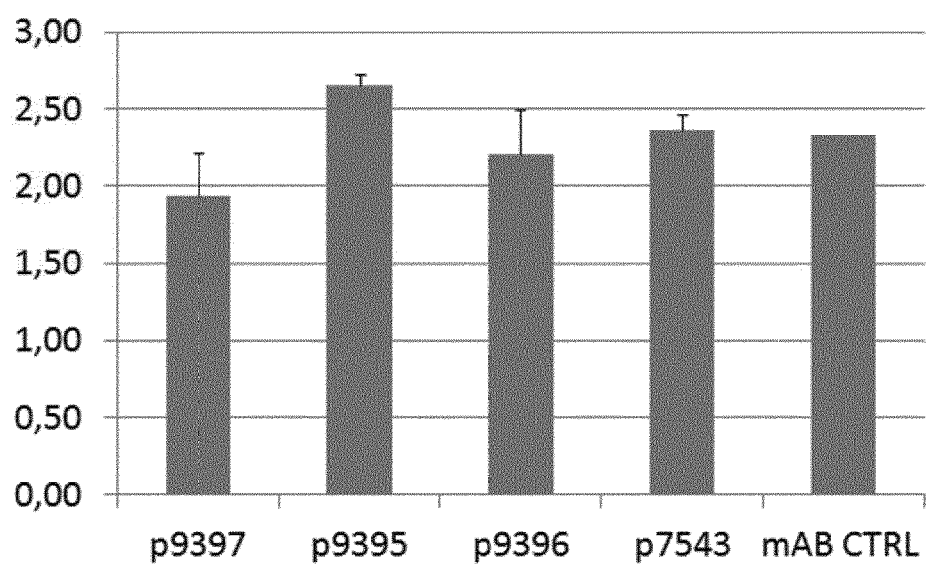

FIG. 22: b): Immunesera generated by various terminally modified peptide vaccines (such as e.g. p9397, p9395, p9396) recognize recombinant HTT protein with the same signal intensity than p7543 immuneserum or control mAB 2166 (1:2000) as indicated. The results are depicted in FIG. 22. Y-axis shows antibody signals (OD) against recHTT610 protein by ELISA analysis as in Example 1.

Figure 23:
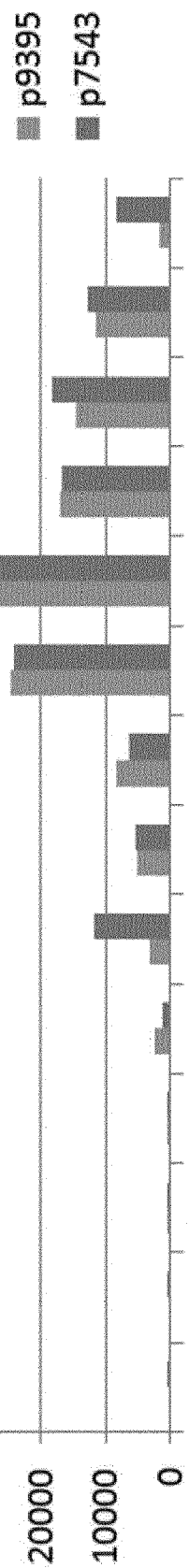

FIG. 23: c): Epitope analysis of immunesera from p7543 and p9395 immunized mice using a 12mer single step peptide walk by peptide ELISA (peptide sequences indicated on x-axis; peptide ELISA as above) confirm epitope consistency between peptide p7543 and its lysine-containing variant p9395, respectively. The results are depicted in FIG. 23. The y-axis displays EC50 values obtained from standard peptide ELISA.

Figure 24:
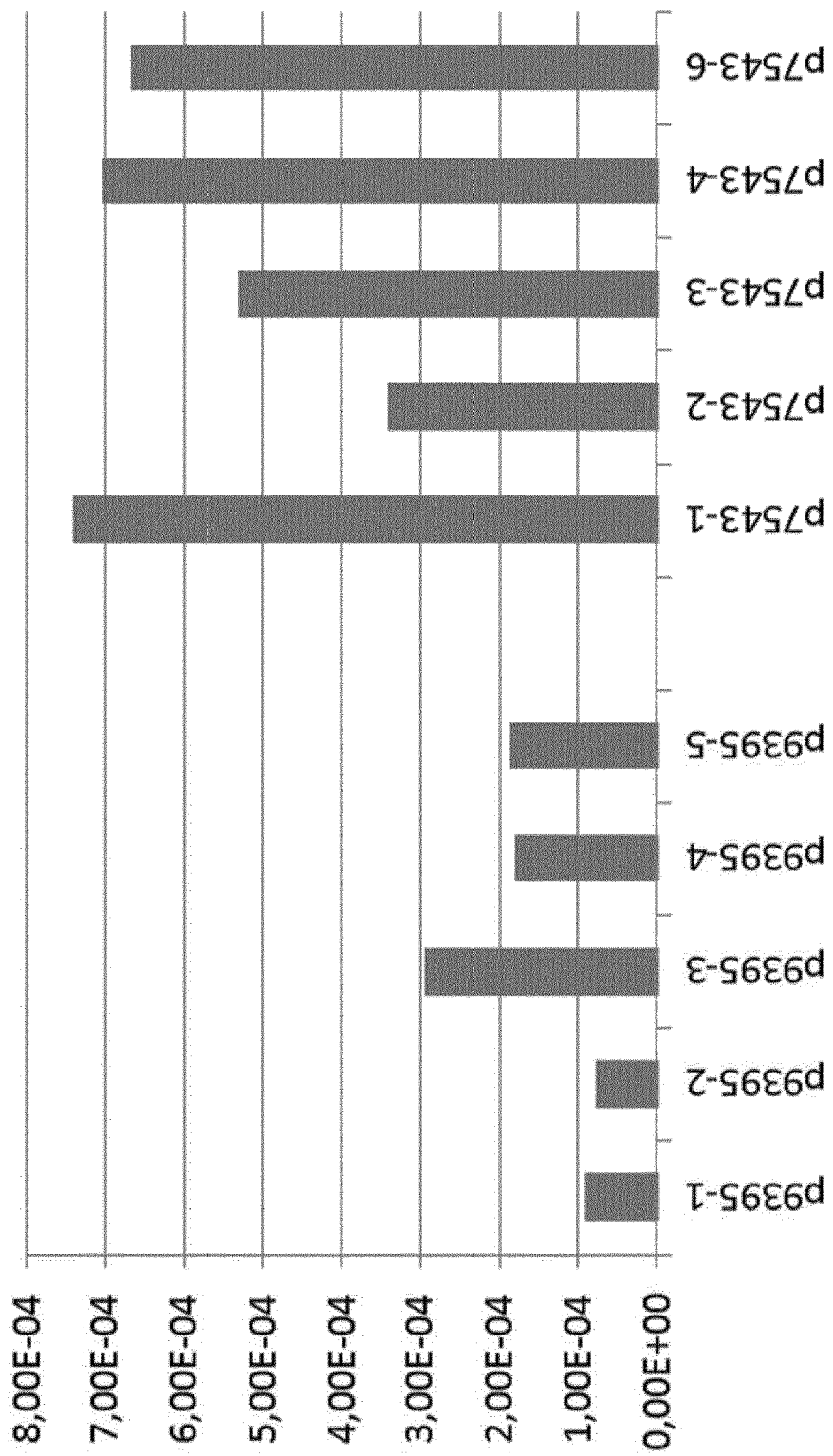

FIG. 24: d): Comparison of Off-rates against biotin/streptavidin-immobilized recombinant Htt protein (recHtt610 as in protein ELISA) of sera derived from immunizations with p7543 and its variant p9395 (x-axis indicates off-rates as determined by label-free surface plasmon resonance [SPR] according to standard procedures [see below]; 5 animals each, designated −1 to −5, respectively, as indicated). The results are depicted in FIG. 24. In conclusion, peptide p9353-derived immunesera show a slower off-rate (average 1.66E−04) than p7543-derived immunesera (average 5.97E−04). The y-axis indicates calculated off-rate values.

Method (for FIG. 24): SPR was performed using a BiaCore 2000 device. C-terminally biotin-tagged peptides were immobilized according to recommended procedures; to avoid unspecific binding on the chip surface, 2×100 µl of 1 µM free D-biotin was injected for blocking. Analyte injections were carried out using a flow of 30 µl/min at 25° C. analysis temperature using HBS-Buffer pH 7.4 as running buffer. 80 µl of each hu AB-SN sample was injected undilute and sterile filtered (0.22 µm); murine control mABs was injected at a concentration of 2 µg/ml, the dissociation time was 500 s. The chip-surface was regenerated using injections of 15 µl of 10 mM Glycin pH 2.1 followed by neutralization. Sensorgrams were reference subtracted in that signals from reference-flow cell 1 were subtracted from signals of peptide immobilized-flow cells. The curve from empty SN was used for background subtraction. The Langmuir 1:1 dissociation model of the BiaEvaluation software was used for Off-rate determination.

Figure 25:
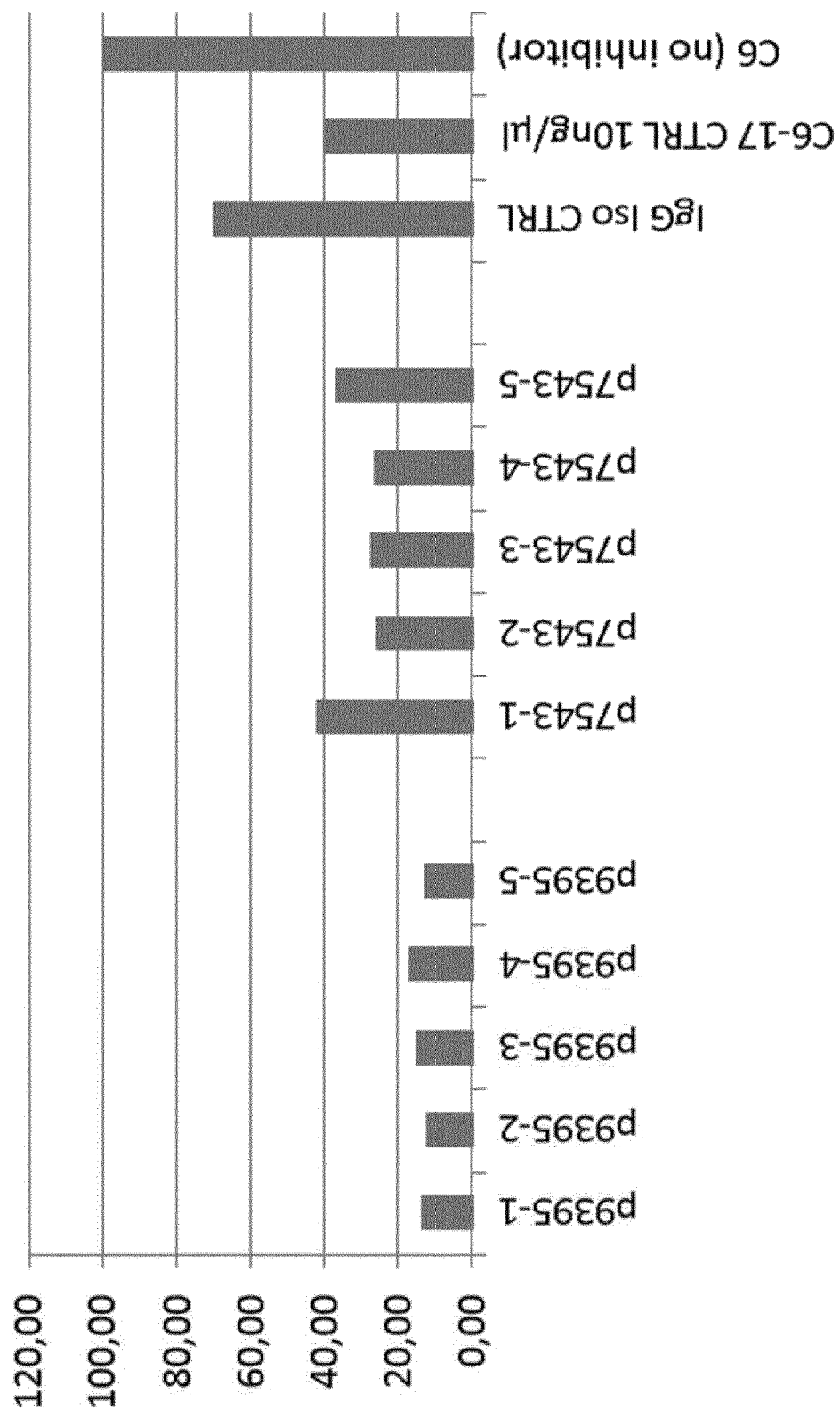

FIG. 25: e): Comparison of in vitro functionality of a modified peptide immuneserum (p9395) with p7543 immuneserum using an in vitro caspase 6 inhibition assay as explained in Example 7. IgG isotype control determines background inhibition activity; mAB C6-17 was used as positive control. The results are depicted in FIG. 25. In conclusion, p9395 immunesera inhibit more efficiently (average 14.2% inhibition by immunesera from 5 animals, displayed on the y-axis) than p7543 sera (average 31.8% from 5 animals). These in vitro inhibition activities are consistent with the above Off-rate as determined by SPR and recombinant HTT protein binding data as determined by ELISA.

Figure 26:
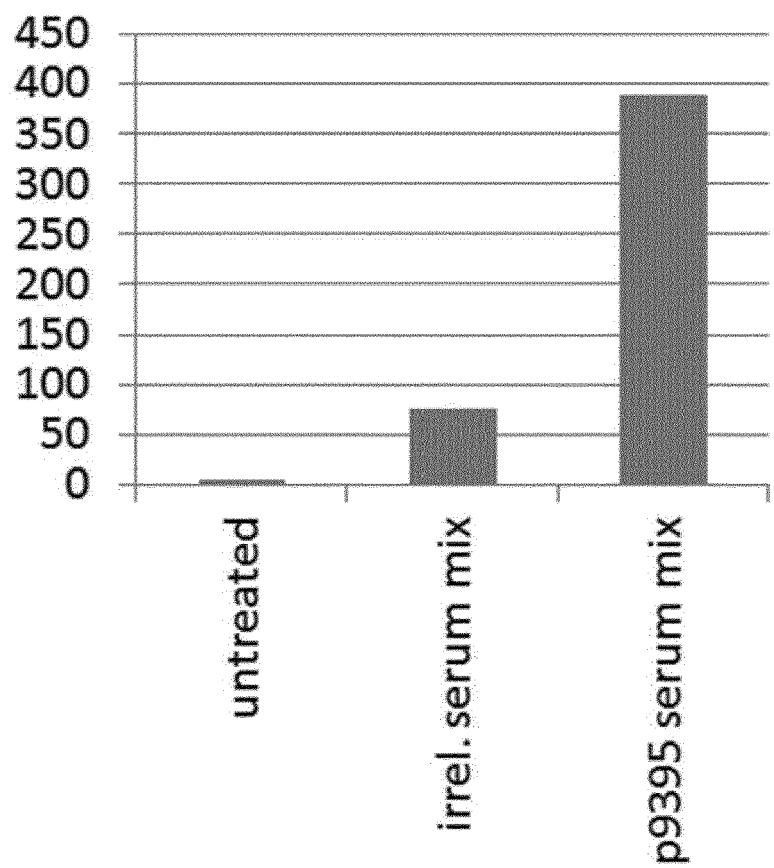

FIG. 26: f): Comparison of in vitro functionality of a modified peptide immunesera (p9395) with p7543 immunesera using an in vitro phagocytosis assay as described below. The results are depicted in FIG. 26. A mixture of 5 sera from p9395 immunized animals shows phagocytotic activity (expressed as MFI; displayed on the y-axis) when compared to a mixture of sera derived from 5 nonspecifically immunized animals confirming phagocytic activity of immunesera generated by terminally modified peptides.

Example 9

—Antibody Humanization a): Antibody humanization of original antibodies PRR13 and hC6-17, respectively was preferred as follows: Prototypic frameworks for heavy and light chain variable regions were used for the generation of series hPRR13-1 to -16 and hC6-17-1 to -16,respectively. Series included prototypic variants containing modifications at one or several amino acid positions in the heavy (designated Framework H) and/or light chain (designated Framework L) as indicated in FIG. 27. Numbers reflect amino acid positions within the framework regions indicated for the humanized antibodies below.

hPRR13 series light chain variable region
(SEQ ID NO: 95)
[EIVLTQSPSSLSASVGDRVTITCTASSSVTSSYLHWYQQKPGKAPKLLI

YSTSNLAS-

GVPSRFSGSGSGTDFTFTISSLQPEDIATYYCHQYRRPPRTFGGGTKLEI

KR];

hPRR13 heavy chain variable region
(SEQ ID NO: 96)
[EVQLVESGPEVKKPGATVKISCKVSGYTFTDFYMKWVQQAPGRGLEWMG

DIDPKNG-

DTFYNQKFKGRVTMTADTSTGTAYMQLSSLTSEDTAVYFCASYYGYTMDY

WGQGTTVTVAS];

hC6-17 light chain variable region
(SEQ ID NO: 97)
[DIVMTQSPDSLAVSLGERATINCKSSQSLLNSRTRKNYLAWYQQKPGQP

PKLLI-

YWASTRESGVPDRFSGSGSGTDFTLTISSLQAEDVAVYYCKQSYNLLTFG

GGTKLEIK];

hC6-17 heavy chain variable region
(SEQ ID NO: 98)
[QVQLVQSGAEVKKPGASVKVSCKASGYTFTEYTMHWVRQAPGRGLEWMG

GINPN-

NGGTRYNQKFKGRVTMTRDTSIRTAYVELSRLTSDDTAVYYCASLDGRDY

WGQGTLVTVSS]

Methods: Human vLC and vHC sequences were synthesized and cloned into the expression vector pFUSE2ss CLg-hk (EcoRI/NheI) and pFUSEss CHIg-hG1 (EcoRI/BsiWI). Cloning procedures were performed according to standard molecular biology procedures essentially as indicated by manufacturers including restriction digestions and ligation reactions (NEB Quick ligase kit; CatNr. M2200L), bacterial transformation followed by clone selection and analysis. DNA fragment preparations from agarose gels were performed using standard DNA purification kits (Quiagen; CatNr. 27106). HEK293 freestyle cells (Invitrogen; CatNr. R790-07) were grown in medium as indicated by the manufacturer and transiently co-transfected with different combinations of hu AB heavy and light chain vectors as indicated in the table. Cell culture SNs were collected 24-48 h after transfection and concentrated 1:30 followed by buffer exchange (PBS) using Spin-X UF500 tubes (Corning, CLS431478). Concentrated human antibody-SNs were tested by in vitro peptide and protein binding using ELISA (as in Example 1). Further characterization was performed as indicated throughout this Example 9.

FIG. 28: b): As an example, recognition of recHTT610 protein by humanized mAB PRR13 derivatives hPRR13-10, hPRR13-12 and hPRR13-14 containing framework mutations indicated can be demonstrated by protein ELISA (performed as in Example 1; see FIG. 28. Y-axis reflects rec Htt610 binding activity[OD]).

FIG. 29 c): As an example, a humanized antibody from the hC6-17 series modified as proposed in a), maintains in vitro phagocytic activity. The in vitro phagocytic assay was performed as above and shows (see FIG. 29) that in contrast to non-incubated beads (no AB) or irrelevant isotype control beads (IgG), mAB hC6-17-6-incubated beads are efficiently phagocytosed in vitro thereby providing an example of maintaining anti HTT-specific functionality based on HTT recognition by the antibody.

```
p6773   PRR   LPQPPPQAQPLLPQPQPC           ++ active vacc.mAB generation
              (SEQ ID NO: 1)

p7564   C6    CPSDSSEIVLD                  ++ active vacc.mAB generation
              (SEQ ID NO: 2)

p7543   C6    GTDNQYLGLQIGC                ++ active vacc.mAB generation   C6 inhibition
              (SEQ ID NO: 3)

p6771   PRR   LPQPPPQAQPLLPC               ++ active vacc.mAB generation
              (SEQ ID NO: 4)

p8346   Ex1   CGPAVAEEPLHRP                ++ active vacc.mAB generation
              (SEQ ID NO: 5)

p8855   C6    SDSSEIVLDGTDC                ++ active vacc.               C6 inhibition
              (SEQ ID NO: 6)

p8858   C6    EIVLDGTDNQYLC                ++ active vacc.               C6 inhibition
              (SEQ ID NO: 7)

p8859   C6    IVLDGTDNQYLGC                ++ active vacc.               C6 inhibition
              (SEQ ID NO: 8)

p8860   C6    VLDGTDNQYLGLC                ++ active vacc.               C6 inhibition
              (SEQ ID NO: 9)

p8861   C6    LDGTDNQYLGLQC                ++ active vacc.               C6 inhibition
              (SEQ ID NO: 10)

p8862   C6    DGTDNQYLGLQIGC               ++ active vacc.               C6 inhibition
              (SEQ ID NO: 11)

p8869   C6    CTDNQYLGLQIGQ                ++ active vacc.               C6 inhibition
              (SEQ ID NO: 12)

p8868   C6    CGTDNQYLGLQIG                +  active vacc.               C6 inhibition
              (SEQ ID NO: 13)

p8870   C6    CDNQYLGLQIGQP                +  active vacc.               C6 inhibition
              (SEQ ID NO: 14)

p8871   C6    CNQYLGLQIGQPQ                +  active vacc.               C6 inhibition
              (SEQ ID NO: 15)

p6772   PRR   CPQLPQPPPQAQPLLP             +  active vacc.               C6 inhibition
              (SEQ ID NO: 16)

p8864   C6    TDNQYLGLQIGQC                ++ active vacc.
              (SEQ ID NO: 17)

p8865   C6    DNQYLGLQIGQPC                ++ active vacc.
              (SEQ ID NO: 18)

p6775   PRR   PPPQLPQPPPQAQPLLPQPQPaC      ++ active vacc.
              (SEQ ID NO: 19)

p8854   C6    PSDSSEIVLDGTC                +  active vacc.
              (SEQ ID NO: 20)

p8856   C6    DSSEIVLDGTDNC                +  active vacc.
              (SEQ ID NO: 21)

p8857   C6    SEIVLDGTDNQYC                +  active vacc.
              (SEQ ID NO: 22)

p8866   C6    NQYLGLQIGQPQC                +  active vacc.
              (SEQ ID NO: 23)

p8867   C6    QYLGLQIGQPQDC                +  active vacc.
              (SEQ ID NO: 24)
```

| | | | | |
|---|---|---|---|---|
| p6763 | Nter Ca | MATLEKLMKAFESLKSFQ (SEQ ID NO: 25) | | |
| p6764 | Nter Ca | KLMKAFESLKSFQ (SEQ ID NO: 26) | | |
| p6765 | polyQ | CEEQQRQQQQQQQ (SEQ ID NO: 27) | | |
| p6768 | polyQ | QQQQQQQPPPPPPPPaKKKC (SEQ ID NO: 28) | | |
| p7541 | C6 | CSEIVLD (SEQ ID NO: 29) | | |
| p7552 | C6 | CSSEIVLD (SEQ ID NO: 30) | | |
| p7562 | C6 | CDSSEIVLD (SEQ ID NO: 31) | | |
| p7563 | C6 | CSDSSEIVLD (SEQ ID NO: 32) | | |
| p7565 | C6 | CSEIVLDGT (SEQ ID NO: 99) | | |
| p7567 | C6 | CEIVLD (SEQ ID NO: 33) | | |
| p7568 | C6 | CIVLD (SEQ ID NO: 34) | | |
| p7605 | C6 | CSEIVL (SEQ ID NO: 35) | | |
| p6776 | C6 | CSEIVLDGIDNQYL (SEQ ID NO: 36) | ++ active vacc. | C6 inhibition |
| p6777 | C6 | CSDSSEIVLDGTDN (SEQ ID NO: 37) | ++ active vacc. | C6 inhibition |
| p6776b | C6 | SEIVLDGTDNQYLC (SEQ ID NO: 38) | | |
| p7752 | C6 | CAEIVLDGTDNQYL (SEQ ID NO: 39) | | |
| p7753 | C6 | CSAIVLDGTDNQYL (SEQ ID NO: 40) | | |
| p7754 | C6 | CSEAVLDGTDNQYL (SEQ ID NO: 41) | | |
| p7755 | C6 | CSEIALDGTDNQYL (SEQ ID NO: 42) | | |
| p7756 | C6 | CSEIVADGTDNQYL (SEQ ID NO: 43) | | |
| p7757 | C6 | CSEIVLAGTDNQYL (SEQ ID NO: 44) | | |
| p7758 | C6 | CSEIVLDATDNQYL (SEQ ID NO: 45) | | |
| p7745 | C6 | CSEIVLDGADNQYL (SEQ ID NO: 46) | | |
| p7746 | C6 | CSEIVLDGTANQYL (SEQ ID NO: 47) | | |
| p7747 | C6 | CSEIVLDGTDAQYL (SEQ ID NO: 48) | | |

-continued

```
p7748  C6    CSEIVLDGTDNAYL
             (SEQ ID NO: 49)

p7749  C6    CSEIVLDGTDNQAL
             (SEQ ID NO: 50)

p7750  C6    CSEIVLDGTDNQYA
             (SEQ ID NO: 51)
```

Especially preferred for active vaccination ("++ active vacc.")
Preferred for active vaccination ("+ active vacc.")
Preferred for mAB generation ("mAB generation")
Preferred for C6 cleavage inhibition ("C6 inhibition")

Literature

Bard et al., 2014, Journal of Biomolecular Screening, Volume 19(2), 191-204
Butler et al., 2012, Progress in Neurobiology, Volume 97(2): 190-204
Davidson, 2012, Molecular Therapy, Volume 20(10): 1838
Ellrichmann et al., 2013, Clin Dev Immunol., 2013; 2013: 541259
Graham et al., 2010, J Neurosci., Volume 30(45):15019-29
Ko et al., 2001, Brain Research Bulletin, Volume 56(3/4): 319-329
Liu, 2007, Journal of the American Society for Mass Spectrometry. Volume 18(7):1249-64 Mandler et al.; Acta Neuropathologica 127 (2014): 861-879
Messer & Joshi, 2013, Neurotherapeutics, Volume 10: 447-458
Modregger et al., 2002, Human Molecular Genetics, Volume 11(21):2547-58
Novak & Tabrizi, 2011, International Review of Neurobiology, Volume 98: 297-323
O'Hagan & Valiante, 2003, Nature Reviews Drug Discovery, Volume 2(9): 727-35
Singh & O'Hagan, 1999, Nature Biotechnology, Volume 17(11): 1075-81
Southwell et al., 2011, PloS ONE, Volume 6(1): e16676
Stadler et al.; Angewandte Chemie International Edition England 2008; Vol 47(37):7132-5Tezel et al., 2012, Investigative Ophthalmology & Visual Science Volume 53(13): 8222-31
Träger et al., 2014, Brain, Volume 137(3):819-33
Warby et al., 2008, Human Molecular Genetics, Volume 17(15): 2390-2404
Weiss et al., Analytical Biochemistry 2009; Vol 395(1):8-15
Weiss et al., 2012, The Journal of Clinical Investigation, Volume 122(10): 3731-3736
Weiss et al. 2014, 9th Annual Huntington's Disease Therapeutics Conference (CHDI); Palm Springs USA, Abstract.
Wong et al. 2014; 9th Annual Huntington's Disease Therapeutics Conference (CHDI); Palm Springs USA, Abstract.
Yu et al., 2014, Trends in Pharmacological Sciences, Volume 35(2): 53-62
Zhang et al.; Current Protocols in Immunology 2008; Chapter: Unit-14.1
Zheng & Diamond, 2012, Progress in Molecular Biology and Translational Science, Volume 107: 189-214

Accordingly, the following embodiments can be defined as preferred embodiments of the present invention:

1. Immunogenic peptide of the HTT protein, preferably selected from the group consisting of p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94); p7543b (TDNQYLGLQIC; SEQ ID No. 89), p7543c (TDNQYLGLQIGC; SEQ ID No. 90), p6771 (LPQPPPQAQPLLPC, SEQ ID No. 4), p8346 (CGPAVAEEPLHRP, SEQ ID No. 5), p8855 (SDSSEIVLDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869 (CTDNQYLGLQIGQ, SEQ ID No. 12), p8868 (CGTDNQYLGLQIG, SEQ ID No. 13), p8870 (CDNQYLGLQIGQP, SEQ ID No. 14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PP-PQLPQPPPQAQPLLPQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), p8867 (QYLGLQIGQPQDC, SEQ ID No. 24), p6763 (CaMATLEKLMKAFESLKSFQ, SEQ ID No. 25), p6764 (CaKLMKAFESLKSFQ, SEQ ID No. 26), p6765 (CEEQQRQQQQQQQ, SEQ ID No. 27), p6768 (QQQQQQP-PPPPPPaKKKC, SEQ ID No. 28), p7541 (CSEIVLD, SEQ ID No. 29), p7552 (CSSEIVLD, SEQ ID No. 30), p7562 (CDSSEIVLD, SEQ ID No. 31), p7563 (CSDSSEIVLD, SEQ ID No. 32), p7567 (CEIVLD, SEQ ID No. 33), p7568 (CIVLD, SEQ ID No. 34), p7605 (CSEIVL, SEQ ID No. 35), p6776 (CSEIVLDGTDNQYL, SEQ ID No. 36), p6777 (CSDSSEIVLDGTDN, SEQ ID No. 37), p6776b (SEIVLDGTDNQYLC, SEQ ID No. 38), p7752 (CAEIVLDGTDNQYL, SEQ ID No. 39), p7753 (CSAIVLDGTDNQYL, SEQ ID No. 40), p7754 (CSEAVLDGTDNQYL, SEQ ID No. 41), p7755 (CSEIALDGTDNQYL, SEQ ID No. 42), p7756 (CSEIVADGTDNQYL, SEQ ID No. 43), p7757 (CSEIVLAGTDNQYL, SEQ ID No. 44), p7758 (CSEIVLDATDNQYL, SEQ ID No. 45), p7745 (CSEIVLDGADNQYL, SEQ ID No. 46), p7746 (CSEIVLDGTANQYL, SEQ ID No. 47), p7747 (CSEIVLDGTDAQYL, SEQ ID No. 48), p7748 (CSEIVLDGTDNAYL, SEQ ID No. 49), p7749 (CSEIVLDGTDNQAL, SEQ ID No. 50), and p7750 (CSEIVLDGTDNQYA, SEQ ID No. 51), more preferred p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p6771 (LPQPPPQAQPLLPC, SEQ ID No. 4), p8346 (CGPAVAEEPLHRP, SEQ ID No. 5), p8855 (SDSSEIVLDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869

(CTDNQYLGLQIGQ, SEQ ID No. 12), p8868 (CGTDN-QYLGLQIG, SEQ ID No. 13), p8870 (CDNQYLGLQI-GQP, SEQ ID No. 14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PP-PQLPQPPPQAQPLLPQPQPaC, SEQ ID No. 19), p6776 (CSEIVLDGTDNQYL, SEQ ID No. 36), p6777 (CSDS-SEIVLDGTDN, SEQ ID No. 37), p8854 (PSDSSEIV-LDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), and p8867 (QYLGLQIGQPQDC, SEQ ID No. 24), especially p6773 (LPQPPPQAQPLLPQPQPC, SEQ ID No. 1), p7564 (CPSDSSEIVLD, SEQ ID No. 2), p7543 (GTDNQYL-GLQIGC, SEQ ID No. 3), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), and p8346 (CGPAVAEEPLHRP, SEQ ID No. 5); wherein the N- or C-terminal cysteine residue (C) may be present or not or provided alternatively at the C- or N-terminus; or peptides comprising at least one of these peptides with SEQ ID NOs 1 to 51, preferably in a total length of maximally 50 amino acid residues, more preferred of maximally 30 amino acid residues, further preferred of maximally amino acid residues, especially of maximally 16 amino acid residues.

2. Peptide-based vaccine for use in the treatment and/or prevention of Huntington's disease, comprising at least one immunogenic peptide of the Huntingtin (HTT) protein, preferably at least one peptide selected from the peptides of embodiment 1, and optionally also one or more adjuvants.

3. Peptide-based vaccine for use according to embodiment 2, characterised in that the at least one immunogenic peptide is coupled to a pharmaceutically acceptable carrier, preferably KLH.

4. Peptide-based vaccine for use according to embodiment 2 or 3, characterised in that the vaccine is formulated for intravenous, subcutaneous, intradermal or intramuscular administration.

5. Peptide-based vaccine for use according to any one of embodiments 2 to 4, characterised in that the vaccine is formulated with an adjuvant, preferably aluminium hydroxide.

6. Peptide-based vaccine according to any one of embodiments 2 to 5, characterised in that the at least one peptide is contained in the vaccine in an amount from 0.1 ng to 10 mg, preferably 10 ng to 1 mg, in particular 100 ng to 100 μg.

7. Peptide-based vaccine for use according to embodiment 2 or 6, wherein said at least one immunogenic peptide of the HTT proteins is selected from the group according to embodiment 1, preferably wherein the combination is p7543 (GTDNQYLGLQIGC, SEQ ID No. 3) (or p7543a (DN-QYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTD-NQYLGLQIKKGC; SEQ ID No. 93), p9397 (KDNQYL-GLQIKKGC; SEQ ID No. 94); p7543b (TDNQYLGLQIC; SEQ ID No. 89), p7543c (TDNQYLGLQIGC; SEQ ID No. 90)) with at least one peptide, selected from SEQ ID NOs 1, 2, 4 and 5, especially wherein the combination comprises or consists of p7543 (GTDNQYLGLQIGC, SEQ ID No. 3) and p6771 (LPQPPPQAQPLLPC, SEQ ID No. 4) or p7543 (GTDNQYLGLQIGC, SEQ ID No. 3) and p7564 (CPSDS-SEIVLD, SEQ ID No. 2), wherein the N- or C-terminal cysteine residue (C) may be present or not or provided alternatively at the C- or N-terminus.

8. Peptide-based vaccine according to any one of embodiments 2 to 7, characterised in that it comprises at least one peptide from the "C6" region of HTT and at least one peptide from the "PRR" region of HTT, preferably wherein the at least one peptide is each selected from the group according to table 2.

9. Pharmaceutical preparation comprising an immunogenic peptide according to embodiment 1 or an immunogenic peptide comprising or consisting of a core epitope selected from the group consisting of LLPQP (SEQ ID No. 77), PPQAQPL (SEQ ID No. 78), PPQAQP (SEQ ID No. 79), QPLL (SEQ ID No. 80) and PQAQPLL (SEQ ID No. 81), especially LLPQP, and QYLGLQIG (SEQ ID No. 82), YLGLQIG (SEQ ID No. 83), DNQYLGLQIG (SEQ ID No. 84), DNQYLGL (SEQ ID No. 85) and YLGLQIG (SEQ ID No. 86), especially QYLGLQIG; preferably with a maximum length of 30, preferably 20, more preferred 16 amino acid residues, especially with a length of 6 to 10 amino acids.

10. Pharmaceutical preparation according to embodiment 9, characterised in that it is for use to elicit an immune response in an individual, especially an individual having Huntington's disease.

11. Pharmaceutical preparation according to embodiment 9 or 10, characterised in that it comprises a peptide-based vaccine according to any one of embodiments 2 to 8.

12. Pharmaceutical preparation according to any one of embodiments 9 to 11, characterised in that it is for use to elicit anti HTT antibodies in an individual, especially an individual having Huntington's disease.

13. Pharmaceutical preparation according to any one of embodiments 9 to 12, characterised in that it is combined with a pharmaceutical preparation of an anti HTT antibody and preferably administered to an individual in separate administration procedures.

14. Pharmacological composition comprising a polyclonal antibody specifically recognising at least one immunogenic peptide of the HTT protein for use as a vaccine in the treatment and/or prevention of Huntington's disease.

16. Monoclonal antibody having a binding domain capable of binding to a peptide of the HTT protein having the sequence of p6773 (SEQ ID No. 1), especially to the core epitope LLPQP (SEQ ID No. 77).

17. Monoclonal antibody according to embodiment 16, characterised in that the said monoclonal antibody comprises a heavy chain variable region CDR1 comprising GYSFTDFY (SEQ ID No. 54), a heavy chain variable region CDR2 comprising IDPKNGDT (SEQ ID No. 55), a heavy chain variable region CDR3 comprising ATYYGYT-MDY (SEQ ID No. 56), a light chain variable region CDR1 comprising SSVTSSY (SEQ ID No. 57), a light chain variable region CDR2 comprising STS (SEQ ID No. 58) a light chain variable region comprising HQYRRPPRT (SEQ ID No. 59), said antibody being preferably the monoclonal antibody PRR13.

18. Monoclonal antibody according to embodiment 16 or 17, wherein said monoclonal antibody is a human, humanized, bispecific or chimeric monoclonal antibody.

19. Monoclonal antibody according to any one of embodiments 16 to 18 for use in a pharmaceutical composition used in the prevention and/or treatment of Huntington's disease.

20. Monoclonal antibody for use according to embodiment 19, characterised in that said composition additionally contains a pharmaceutically acceptable carrier or excipient.

21. Monoclonal antibody for use according to embodiment 19 or 20, characterised in that said composition further contains at least one additional therapeutic agent.

22. Monoclonal antibody for use according to any one of embodiments 19 to 21, characterised in that said composition is formulated for intravenous, subcutaneous, intradermal or intramuscular administration.

23. Monoclonal antibody for use according to any one of embodiments 19 to 22, characterised in that the monoclonal antibody is coupled to a molecule which enhances phagocytic properties.

24. Monoclonal antibody for use according to any one of embodiments 19 to 23, characterised in that the monoclonal antibody is contained in said composition in an amount from 1 mg to 10 g, preferably 50 mg to 2 g, in particular 100 mg to 1 g.

25. Monoclonal antibody having a binding domain capable of binding to a peptide of the HTT protein having the sequence of p7543 (SEQ ID No. 3).

26. Monoclonal antibody according to embodiment 25, characterised in that said monoclonal antibody comprises a heavy chain variable region CDR1 comprising GYTFTEYT (SEQ ID No. 66), a heavy chain variable region CDR2 comprising INPNNGGT (SEQ ID No. 67), a heavy chain variable region CDR3 comprising ASLDGRDY (SEQ ID No. 68), a light chain variable region CDR1 comprising QSLLNSRTRKNY SEQ ID No. 69), a light chain variable region CDR2 comprising WAS (SEQ ID No. 70) and a light chain variable region comprising KQSYNLLT (SEQ ID No. 71), said antibody being preferably the monoclonal antibody C6-17.

27. Monoclonal antibody according to embodiment 25 or 26, wherein said monoclonal antibody is a human, humanized, bispecific or chimeric monoclonal antibody, preferably a bispecific antibody with a specificity to the PRR region of HTT, especially containing an antibody according to embodiments 16 to 24.

28. Monoclonal antibody according to any one of embodiments 25 to 27 for use in a pharmaceutical composition used in the prevention and/or treatment of Huntington's disease.

29. Monoclonal antibody for use according to embodiment 28, characterised in that said composition additionally contains a pharmaceutically acceptable carrier or excipient.

30. Monoclonal antibody for use according to embodiment 28 to 29, characterised in that said composition further contains at least one additional therapeutic agent.

31. Monoclonal antibody for use according to embodiment 28 to 30, characterised in that said composition is formulated for intravenous, subcutaneous, intradermal or intramuscular administration.

32. Monoclonal antibody for use according to embodiment 28 to 31, characterised in that the monoclonal antibody is coupled to a molecule which enhances phagocytic properties.

33. Monoclonal antibody for use according to embodiment 28 to 32, characterised in that the monoclonal antibody is contained in said composition in an amount from 1 mg to 10 g, preferably 50 mg to 2 g, in particular 100 mg to 1 g.

34. Monoclonal antibody having a binding domain capable of binding to a peptide of the HTT protein having the sequence of p7564 (SEQ ID No. 2), preferably for use for the treatment of Huntington' disease.

35. Monoclonal antibody according to embodiment 34, characterised in that said monoclonal antibody comprises a heavy chain variable region CDR1 comprising GFTFNTYA (SEQ ID No. 72), a heavy chain variable region CDR2 comprising IRSKSNNYAT (SEQ ID No. 73), a heavy chain variable region CDR3 comprising VRHGEYGNPWFAY (SEQ ID No. 74), a light chain variable region CDR1 comprising QSLVHSNGNTY (SEQ ID No. 75), a light chain variable region CDR2 comprising KVS (SEQ ID No. 76) and a light chain variable region comprising SQSTHVPYT (SEQ ID No. 77), said antibody being preferably the monoclonal antibody M1D1.

36. Monoclonal antibody according to embodiment 34 or 35, wherein said monoclonal antibody is a human, humanized, bispecific or chimeric monoclonal antibody.

37. Monoclonal antibody according to any one of embodiments 34 to 36 for use in a pharmaceutical composition used in the prevention and/or treatment of Huntington's disease.

38. Monoclonal antibody for use according to embodiment 37, characterised in that said composition additionally contains a pharmaceutically acceptable carrier or excipient.

39. Monoclonal antibody for use according to embodiment 37 or 38, characterised in that said composition further contains at least one additional therapeutic agent.

40. Monoclonal antibody for use according to any one of embodiments 37 to 39, characterised in that said composition is formulated for intravenous, subcutaneous, intradermal or intramuscular administration.

41. Monoclonal antibody for use according to embodiment 37 to 40, characterised in that the monoclonal antibody is coupled to a molecule which enhances phagocytic properties.

42. Monoclonal antibody for use according to any one of embodiments 37 to 41, characterised in that the monoclonal antibody is contained in said composition in an amount from 1 mg to 10 g.

43. Monoclonal antibody for use according to embodiment 42, wherein the monoclonal antibody is contained in said composition in an amount from 50 mg to 2 g, in particular 100 mg to 1 g 44. Monoclonal antibody for use according to embodiment 42, wherein the monoclonal antibody is contained in said composition in an amount from 100 mg to 1 g.

45. Monoclonal antibody for use according to embodiment 42, wherein the monoclonal antibody is a polyclonal antibody.

46. Monoclonal antibody for use according to embodiment 42, wherein the monoclonal antibody is a monoclonal antibody.

47. Monoclonal antibody for use according to embodiment 42, wherein the monoclonal antibody is a human monoclonal antibody.

48. Monoclonal antibody for use according to embodiment 42, wherein the monoclonal antibody is a humanized monoclonal antibody.

49. Monoclonal antibody for use according to embodiment 42, wherein the monoclonal antibody is a bispecific monoclonal antibody.

50. Monoclonal antibody for use according to embodiment 42, wherein the monoclonal antibody is a bispecific monoclonal antibody with two specificities against HTT.

51. Monoclonal antibody for use according to embodiment 50, wherein the monoclonal antibody is a bispecific monoclonal antibody with a binding region to PRR or to C6.

52. Monoclonal antibody for use according to embodiment 50, wherein the monoclonal antibody is a bispecific monoclonal antibody with a binding region to PRR and C6.

53. Monoclonal antibody M1D1 for use as a probe in drug screening.

54. Monoclonal antibody M1D1 for use according to embodiment 53 wherein molecules are screened that inhibit the accession of proteases to caspase cleaving region amino acid position 586 of HTT 55. Method for diagnosing in vitro Huntington's disease in a mammal, comprising the steps of:

determining the level of wild type or mutated Huntingtin or fragments thereof in a sample of a mammal using antibodies PRR13, M1D1 or C6-17 alone or in combination;

diagnosing Huntington's disease if the level of wt or mutated Huntingtin in said sample is changed in comparison to a reference sample of healthy individuals, who are genetically unaffected by Huntington's disease;

and, optionally, monitoring the effect of Huntingtin-lowering therapeutic strategies in pre-manifest or manifest Huntington's disease patient samples, wherein the therapeutic strategies are preferably selected from active or passive vaccination, especially in the course of a Huntingtin lowering therapy.

56. Method according to embodiment 55, wherein the determination of the level of wild type or mutated Huntingtin or fragments thereof in a sample involves immunoprecipitation- or capture-based assays, preferably enzyme-linked Immunosorbent Assay (ELISA), enzyme-linked immunoassay (EIA), Fluorescence Resonance Energy Transfer (FRET) based assays, Western blot or immune-histochemistry and immunofluorescence analysis or imaging methods, preferably PET or SPECT and Flow cytometry.

57. Method according to embodiment 55 to 56, wherein said sample is cerebrospinal fluid (CSF), blood, plasma, serum, urine, saliva, sweat, or lacrimal fluid or tissue- and cell extract.

58. Method according to embodiment 55 to 57, wherein said mammal is a human.

59. Method for determining in vitro the stage of Huntington's disease in a mammal, comprising the steps of:
determining the level of wild type or mutated Huntingtin or fragments thereof in a sample of a mammal using the antibodies PRR13, M1D1 or C6-17 alone or in combination and
determining the stage of Huntington's disease.
determining the impact on HTT levels of a Huntingtin lowering therapy.

60. Method according to embodiment 59, wherein the determination of the level of wild type or mutated Huntingtin or fragments thereof in a sample involves immunoprecipitation- or capture-based assays, preferably enzyme-linked Immunosorbent Assay (ELISA), enzyme-linked immunoassay (EIA), Fluorescence Resonance Energy Transfer (FRET) based assays, Western blot or immune-histochemistry and immunofluorescence analysis or imaging methods, preferably PET or SPECT, and Flow cytometry.

61. Method according to embodiment 59 to 60, wherein said sample is cerebrospinal fluid (CSF), blood, plasma, serum, urine, saliva, sweat, or lacrimal fluid or tissue- or cell extracts.

62. Method according to embodiment 59 to 61, wherein said mammal is a human.

63. Method to monitor the progress of Huntington's disease or to monitor the effectiveness of treatment of Huntington's disease in a mammal, comprising the steps of:
determining the level of mutated HTT in a sample of a mammal using the antibody PRR13, M1D1 and C6-17 alone or in combination and
determining the progress of Huntington's disease or the effectiveness of treatment of Huntington's disease by comparing the obtained level of mutated Huntingtin or fragments thereof with the levels obtained in the first measurement of mutated Huntingtin or fragments thereof, preferably in a measurement at the time of diagnosis of the disease associated symptoms, wherein a lowering of the HTT level is indicative of a successful therapy.

64. Method according to embodiment 63, wherein the determination of the level of mutated HTT in a sample involves immunoprecipitation- or capture-based assays, preferably enzyme-linked Immunosorbent Assay (ELISA), enzyme-linked immunoassay (EIA), Fluorescence Resonance Energy Transfer (FRET) based assays, Western blot or immune-histochemistry and immunofluorescence analysis or imaging methods, preferably: PET or SPECT, and Flow cytometry.

65. Method according to embodiment 63 to 64, wherein said sample is cerebrospinal fluid (CSF), blood, plasma, serum, saliva, sweat, or lacrimal fluid or brain or tissue extracts.

66. Method according to embodiment 63 to 65, wherein said mammal is a human.

67. Use of at least one immunogenic peptide selected from the group consisting of p6773 (LPQPPPQAQPLL-PQPQPC, SEQ ID No. 1), p7564 (CPSDSSEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94); p7543b (TDN-QYLGLQIC; SEQ ID No. 89), p7543c (TDNQYL-GLQIGC; SEQ ID No. 90), p6771 (LPQPPPQAQPLLPC, SEQ ID No. 4), p8346 (CGPAVAEEPLHRP, SEQ ID No. 5), p8855 (SDSSEIVLDGTDC, SEQ ID No. 6), p8858 (EIV-LDGTDNQYLC, SEQ ID No. 7), p8859 (IVLDGTDN-QYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869 (CTDNQYLGLQIGQ, SEQ ID No. 12), p8868 (CGTDN-QYLGLQIG, SEQ ID No. 13), p8870 (CDNQYLGLQI-GQP, SEQ ID No. 14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PP-PQLPQPPPQAQPLLPQPQPaC, SEQ ID No. 19), p8854 (PSDSSEIVLDGTC, SEQ ID No. 20), p8856 (DSSEIV-LDGTDNC, SEQ ID No. 21), p8857 (SEIVLDGTDNQYC, SEQ ID No. 22), p8866 (NQYLGLQIGQPQC, SEQ ID No. 23), p8867 (QYLGLQIGQPQDC, SEQ ID No. 24), p6763 (CaMATLEKLMKAFESLKSFQ, SEQ ID No. 25), p6764 (CaKLMKAFESLKSFQ, SEQ ID No. 26), p6765 (CE-EQQRQQQQQQQ, SEQ ID No. 27), p6768 (QQQQQQP-PPPPPPPaKKKC, SEQ ID No. 28), p7541 (CSEIVLD, SEQ ID No. 29), p7552 (CSSEIVLD, SEQ ID No. 30), p7562 (CDSSEIVLD, SEQ ID No. 31), p7563 (CSDS-SEIVLD, SEQ ID No. 32), p7567 (CEIVLD, SEQ ID No. 33), p7568 (CIVLD, SEQ ID No. 34), p7605 (CSEIVL, SEQ ID No. 35), p6776 (CSEIVLDGTDNQYL, SEQ ID No. 36), p6777 (CSDSSEIVLDGTDN, SEQ ID No. 37), p6776b (SEIVLDGTDNQYLC, SEQ ID No. 38), p7752 (CAEIV-LDGTDNQYL, SEQ ID No. 39), p7753 (CSAIVLDGTD-NQYL, SEQ ID No. 40), p7754 (CSEAVLDGTDNQYL, SEQ ID No. 41), p7755 (CSEIALDGTDNQYL, SEQ ID No. 42), p7756 (CSEIVADGTDNQYL, SEQ ID No. 43), p7757 (CSEIVLAGTDNQYL, SEQ ID No. 44), p7758 (CSEIVLDATDNQYL, SEQ ID No. 45), p7745 (CSEIV-LDGADNQYL, SEQ ID No. 46), p7746 (CSEIVLDGTAN-QYL, SEQ ID No. 47), p7747 (CSEIVLDGTDAQYL, SEQ ID No. 48), p7748 (CSEIVLDGTDNAYL, SEQ ID No. 49), p7749 (CSEIVLDGTDNQAL, SEQ ID No. 50), and p7750

(CSEIVLDGTDNQYA, SEQ ID No. 51), preferably p6773 (LPQPPPQAQPLLPQPQPC, SEQ ID No. 1), p7564 (CPSDSSEIVLD, SEQ ID No. 2), p7543 (GTDNQYL-GLQIGC, SEQ ID No. 3), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), p8346 (CGPAVAEEPLHRP, SEQ ID No. 5), p8855 (SDSSEIV-LDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDN-QYLGLQIGC, SEQ ID No. 11), p8869 (CTDNQYL-GLQIGQ, SEQ ID No. 12), p8868 (CGTDNQYLGLQIG, SEQ ID No. 13), p8870 (CDNQYLGLQIGQP, SEQ ID No. 14), p8871 (CNQYLGLQIGQPQ, SEQ ID No. 15), p6772 (CPQLPQPPPQAQPLLP, SEQ ID No. 16), p8864 (TDN-QYLGLQIGQC, SEQ ID No. 17), p8865 (DNQYLGLQI-GQPC, SEQ ID No. 18), p6775 (PPPQLPQPPPQAQPLL-PQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), and p8867 (QYL-GLQIGQPQDC, SEQ ID No. 24), especially p6773 (LPQP-PPQAQPLLPQPQPC, SEQ ID No. 1), p7564 (CPSDS-SEIVLD, SEQ ID No. 2), p7543 (GTDNQYLGLQIGC, SEQ ID No. 3), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), and p8346 (CGPA-VAEEPLHRP, SEQ ID No. 5), wherein the N- or C-terminal cysteine residue (C) may be present or not or provided alternatively at the C- or N-terminus; for the manufacture of a medicament for the prevention or treatment of Hunting-ton's disease.

68. Peptide-based vaccine for use in the prevention and/or treatment of Huntington's disease comprising at least one immunogenic peptide of the HTT protein according to embodiment 67.

69. Peptide-based vaccine for use according to embodiment 68, characterised in that the at least one immunogenic peptide is coupled to a pharmaceutically acceptable carrier, preferably KLH.

70. Peptide-based vaccine for use according to embodiment 68 to 69, characterised in that the vaccine is formulated for intravenous, subcutaneous, intradermal or intramuscular administration.

71. Peptide-based vaccine for use according to embodiment 68 to 70, characterised in that the vaccine is formulated with an adjuvant, preferably aluminium hydroxide.

72. Peptide-based vaccine for use according to any one of embodiments 68 to 70, characterised in that the at least one peptide is contained in the vaccine in an amount from 0.1 ng to 10 mg, preferably 10 ng to 1 mg, in particular 100 ng to 100 µg.

73. Immunogenic peptides according to embodiment 67, wherein said peptides are used for the generation or identification of specific Huntingtin C6-cleavage inhibitors.

74. Immunogenic peptides according to embodiment 73, wherein said specific Huntingtin C6-cleavage inhibitors are defined as monoclonal antibodies, polyclonal antisera, monoclonal antibody-derived fragments such as Fv's, scFv's, F(ab), F(ab)2.

75. Antibody or antigen-binding molecule targeting the caspase region 586 C6 region of HTT generated by immu-nisation with peptide-based vaccines according to embodi-ment 68, especially peptides selected from the group con-sisting of p7564
(CPSDSSEIVLD), p7543 (GTDNQYLGLQIGC), p8855 (SDSSEIVLDGTDC), p8858 (EIVLDGTDNQYLC), p8859 (IVLDGTDNQYLGC), p8860
(VLDGTDNQYLGLC), p8861 (LDGTDNQYLGLQC), p8862 (DGTDNQYLGLQIGC), p8869 (CTDNQYL-GLQIGQ), p8868 (CGTDNQYLGLQIG), p8870
(CDNQYLGLQIGQP), p8871 (CNQYLGLQIGQPQ), p8864 (TDNQYLGLQIGQC), p8865 (DNQYLGLQI-GQPC), p8854 (PSDSSEIVLDGTC), p8856 (DSSEIV-LDGTDNC), p8857 (SEIVLDGTDNQYC), p8866
(NQYLGLQIGQPQC), and p8867 (QYLGLQI-GQPQDC), wherein the N- or C-terminal cysteine residue (C) may be present or not or provided alternatively at the C- or N-terminus.

76. Antibody according to embodiment 75, wherein said antibody is a polyclonal antibody.

77. Antibody according to embodiment 75, wherein said antibody is a monoclonal antibody.

78. Antibody or antigen-binding molecule according to embodiment 75 or 77, characterised in that the antibody is coupled to a molecule which enhances phagocytic proper-ties.

79. Antibody or antigen-binding molecule according to any one of embodiments 75 to 78 for use in a pharmaco-logical composition used in the prevention and/or treatment of Huntington's disease.

80. Antibody or antigen-binding molecule for use accord-ing to embodiment 79, characterised in that the composition additionally contains a pharmaceutically acceptable carrier or excipient.

81. Antibody or antigen-binding molecule for use accord-ing to embodiment 79 or 80, characterised in that the composition further contains at least one additional thera-peutic agent.

82. Antibody or antigen-binding molecule for use accord-ing to any one of embodiments 79 to 81, characterised in that the vaccine is formulated for intravenous, subcutaneous, intradermal or intramuscular administration.

83. Antibody or antigen-binding molecule for use accord-ing to any one of embodiments 79 to 82, characterised in that the polyclonal antibodies are contained in the vaccine in an amount from 0.1 mg to 100 mg, preferably 0.5 mg to 20 mg, in particular 1 mg to 10 mg.

The invention claimed is:

1. A method of treating Huntington's disease or delaying the onset of its clinical symptoms, comprising vaccinating a subject in need thereof with a composition comprising an immunogenic peptide of an HTT protein that comprises GTDNQYLGLQIGKKC (SEQ ID NO: 92).

2. The method of claim 1, wherein the immunogenic peptide is coupled to a pharmaceutically acceptable carrier.

3. The method of claim 1, wherein the composition is formulated for intravenous, subcutaneous, intradermal or intramuscular administration.

4. The method of claim 1, wherein the immunogenic peptide is present in the composition in an amount from 0.1 ng to 10 mg.

5. The method of claim 1, wherein the composition further comprises an adjuvant.

6. The method of claim 5, wherein the adjuvant comprises aluminum hydroxide.

* * * * *